US011845953B2

(12) United States Patent
Nishida et al.

(10) Patent No.: US 11,845,953 B2
(45) Date of Patent: Dec. 19, 2023

(54) METHOD FOR CONVERTING NUCLEIC ACID SEQUENCE OF CELL SPECIFICALLY CONVERTING NUCLEIC ACID BASE OF TARGETED DNA USING CELL ENDOGENOUS DNA MODIFYING ENZYME, AND MOLECULAR COMPLEX USED THEREIN

(71) Applicant: NATIONAL UNIVERSITY CORPORATION KOBE UNIVERSITY, Kobe (JP)

(72) Inventors: Keiji Nishida, Kobe (JP); Akihiko Kondo, Kobe (JP); Takayuki Arazoe, Kobe (JP); Shin Yoshioka, Kobe (JP)

(73) Assignee: NATIONAL UNIVERSITY CORPORATION KOBE UNIVERSITY, Kobe (JP)

( * ) Notice: Subject to any disclaimer, the term of this patent is extended or adjusted under 35 U.S.C. 154(b) by 762 days.

(21) Appl. No.: 16/496,311

(22) PCT Filed: Mar. 20, 2018

(86) PCT No.: PCT/JP2018/011198
§ 371 (c)(1),
(2) Date: Sep. 20, 2019

(87) PCT Pub. No.: WO2018/174097
PCT Pub. Date: Sep. 27, 2018

(65) Prior Publication Data
US 2020/0010856 A1  Jan. 9, 2020

(30) Foreign Application Priority Data

Mar. 22, 2017 (JP) ................................. 2017-056727

(51) Int. Cl.
| | | |
|---|---|---|
| *C12N 15/00* | (2006.01) | |
| *C12N 15/01* | (2006.01) | |
| *C12N 9/78* | (2006.01) | |
| *C12N 9/22* | (2006.01) | |
| *C12N 15/90* | (2006.01) | |
| *C12N 15/11* | (2006.01) | |
| *C12N 15/85* | (2006.01) | |

(52) U.S. Cl.
CPC ............. *C12N 15/907* (2013.01); *C12N 9/22* (2013.01); *C12N 15/11* (2013.01); *C12N 15/85* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 2005/0208489 A1 | 9/2005 | Carroll et al. | |
| 2010/0055731 A1* | 3/2010 | Wang ..................... | C07K 14/37 |
| | | | 435/207 |
| 2011/0002889 A1 | 1/2011 | Barrangou et al. | |
| 2011/0104787 A1* | 5/2011 | Church .................. | C12N 15/63 |
| | | | 435/375 |
| 2017/0073670 A1 | 3/2017 | Nishida et al. | |
| 2017/0247710 A1* | 8/2017 | Nagaraju ............. | C12N 15/102 |
| 2017/0260242 A1 | 9/2017 | Nakamura et al. | |
| 2017/0321210 A1 | 11/2017 | Nishida et al. | |
| 2018/0051266 A1 | 2/2018 | Voytas et al. | |
| 2018/0092889 A1 | 4/2018 | Baysal et al. | |
| 2019/0309288 A1* | 10/2019 | Hess ....................... | C12N 9/22 |
| 2020/0248174 A1 | 8/2020 | Nishida et al. | |

FOREIGN PATENT DOCUMENTS

| | | | |
|---|---|---|---|
| CA | 2992580 A1 | 1/2017 | |
| CN | 106459957 A | 2/2017 | |
| EP | 3115457 A1 | 1/2017 | |
| JP | 2010-519929 A | 6/2010 | |
| JP | 4968498 B2 | 7/2012 | |
| JP | 2013-513389 A | 4/2013 | |
| JP | 2013-128413 A | 7/2013 | |
| WO | WO-2006053021 A2 * | 5/2006 | .............. C12P 21/02 |
| WO | WO 2015/133554 A1 | 9/2015 | |
| WO | WO 2016/070129 A1 | 5/2016 | |
| WO | WO 2016/072399 A1 | 5/2016 | |
| WO | WO 2016/164889 A1 | 10/2016 | |

OTHER PUBLICATIONS

Deng et al., Cancer Lett. 343:161-171, 2014, 29 pages (Year: 2014).*
Greeve et al., Blood 101:3574-580, 2003 (Year: 2003).*
Saini et al., PLoS Genet. 17(1):e1009302, 2021, 23 pages (Year: 2021).*
Cadima-Couto et al., "HIV-1 Vif Interaction with APOBEC3 Deaminases and its Characterization by a New Sensitive Assay," *J. Neuroimmune Pharmacol.*, 6(2): 296-307 (2011).
Esvelt et al., "Genome-scale engineering for systems and synthetic biology," *Mol. Syst. Biol.*, 9: 641 (2012).
Komor et al., "Programmable editing of a target base in genomic DNA without double-stranded DNA cleavage," *Nature*, 533(7603): 420-424, Methods, Extended Data Figures 1-9, and Extended Data Table 1 (2016).

(Continued)

*Primary Examiner* — David Steadman
(74) *Attorney, Agent, or Firm* — Leydig, Voit & Mayer, Ltd.

(57) ABSTRACT

Provided is a method for altering a targeted site of a DNA in a cell, including a step of stimulating the cell with a factor inducing a DNA modifying enzyme endogenous to the cell, and bringing a complex of a nucleic acid sequence-recognizing module specifically binding to a target nucleotide sequence in a given DNA and a DNA modifying enzyme-binding module bonded to each other into contact with the DNA to convert one or more nucleotides in the targeted site to other one or more nucleotides or delete one or more nucleotides, or insert one or more nucleotides into the targeted site.

8 Claims, 3 Drawing Sheets

Specification includes a Sequence Listing.

(56) References Cited

OTHER PUBLICATIONS

Nishida et al., "Targeted nucleotide editing using hybrid prokaryotic and vertebrate adaptive immune systems," *Science*, 353(6305): aaf8729 (2016).
Seeger et al., "Complete Spectrum of CRISPR/Cas9-induced Mutations on HBV cccDNA," *Mol. Ther.*, 24(7): 1258-1266 (2016).
Zetsche et al., "Cpf1 Is a Single RNA-Guided Endonuclease of a Class 2 CRISPR-Cas System," *Cell*, 163: 759-771 (2015).
Japanese Patent Office, International Search Report in International Patent Application No. PCT/JP2018/011198 (dated Jun. 19, 2018).
Canadian Patent Office, Examiner's Report in Canadian Patent Application No. 3,057,432 (dated Jul. 5, 2021).
Intellectual Property Office of Singapore, Written Opinion in Singaporean Patent Application No. 11201908782X (dated Aug. 6, 2021).
Canadian Intellectual Property Office, Examiner's Report in Canadian Patent Application No. 3057432 (dated Apr. 21, 2022).
China National Intellectual Property Administration, Office Action in Chinese Patent Application No. 201880020115.3 (dated Oct. 28, 2022).

\* cited by examiner transfection plasmids for HEK293 cell and HepG2 cell 1923-2 (UGI-nCas9-dVif)

1924-2 (dVif-nCas9-UGI)

1931 (TopBv2-nCas9)

1932 (nCas9-IQGAP2-ZNF335)

ial nuclease wherein a PPR protein constituted to recognize a particular nucleotide sequence by a continuation of PPR motifs each consisting of 35 amino acids and recognizing one nucleic acid base, and nuclease are linked (patent document 4) has also been reported.

METHOD FOR CONVERTING NUCLEIC ACID SEQUENCE OF CELL SPECIFICALLY CONVERTING NUCLEIC ACID BASE OF TARGETED DNA USING CELL ENDOGENOUS DNA MODIFYING ENZYME, AND MOLECULAR COMPLEX USED THEREIN

CROSS-REFERENCE TO RELATED APPLICATIONS

This patent application is the U.S. national phase of International Patent Application No. PCT/JP2018/011198, filed Mar. 20, 2018, which claims the benefit of Japanese Patent Application No. 2017-056727, filed Mar. 22, 2017, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 135,904 bytes ASCII (Text) file named "745963SequenceListing.txt," created Sep. 20, 2019.

TECHNICAL FIELD

The present invention relates to a method for altering a nucleic acid sequence, which enables alteration of a nucleic acid base in a particular region of intracellular target DNA, without introducing an exogenous DNA modifying enzyme or a nucleic acid encoding same into the cell, and a complex of a nucleic acid sequence-recognizing module and a DNA modifying enzyme-binding module to be used therefor.

BACKGROUND ART

In recent years, genome editing is attracting attention as a technique for altering the object gene and genome region in various species. Conventionally, as a method of genome editing, a method utilizing an artificial nuclease comprising a molecule having a sequence-independent DNA cleavage ability and a molecule having a sequence recognition ability in combination has been proposed (non-patent document 1).

For example, a method of performing recombination at a target gene locus in DNA in a plant cell or insect cell as a host, by using a zinc finger nuclease (ZFN) wherein a zinc finger DNA binding domain and a non-specific DNA cleavage domain are linked (patent document 1), a method of cleaving or modifying a target gene in a particular nucleotide sequence or a site adjacent thereto by using TALEN wherein a transcription activator-like (TAL) effector which is a DNA binding module that the plant pathogenic bacteria *Xanthomonas* has, and a DNA endonuclease are linked (patent document 2), a method utilizing CRISPR-Cas9 system wherein DNA sequence CRISPR (Clustered Regularly interspaced short palindromic repeats) that functions in an acquired immune system possessed by eubacterium and archaebacterium, and nuclease Cas (CRISPR-associated) protein family having an important function along with CRISPR are combined (patent document 3) and the like have been reported. Recently, Cpf1 was reported as a new endonuclease for a CRISPR-Cas system (non-patent document 2). Furthermore, a method of cleaving a target gene in the vicinity of a particular sequence, by using artificial nuclease wherein a PPR protein constituted to recognize a particular nucleotide sequence by a continuation of PPR motifs each consisting of 35 amino acids and recognizing one nucleic acid base, and nuclease are linked (patent document 4) has also been reported.

Recently, moreover, the present inventors reported that a genome sequence was successfully altered, without DSB, by nucleic acid base conversion in a region containing a particular DNA sequence in various biological species including yeast and *Escherichia coli*, by using deaminase that catalyzes a deamination reaction and by introducing a complex of the deaminase linked to a molecule having a DNA sequence recognition ability into the host cell (patent document 5, non-patent document 3).

DOCUMENT LIST

Patent Documents patent document 1: JP-B-4968498
patent document 2: National Publication of International Patent Application No. 2013-513389
patent document 3: National Publication of International Patent Application No. 2010-519929
patent document 4: JP-A-2013-128413
patent document 5: WO 2015/133554

Non-Patent Document non-patent document 1: Kelvin M Esvelt, Harris H Wang (2013) Genome-scale engineering for systems and synthetic biology, Molecular Systems Biology 9: 641
non-patent document 2: Bernd Zetsche et al. (2015) Cpf1 Is a Single RNA-Guided Endonuclease of a Class 2 CRISPR-Cas System, Cell 163: 759-771
non-patent document 3: Nishida Keiji et al. (2016) Targeted nucleotide editing using hybrid prokaryotic and vertebrate adaptive immune systems, Science 6: 353(6305)

SUMMARY OF THE INVENTION

Problems to be Solved by the Invention

While the above-mentioned genome editing techniques proposed so far presuppose introduction of an exogenous DNA modifying enzyme into the cell, they are associated with problems of side effects such as cytotoxicity and the like and delivery of the DNA modifying enzyme into the cell or target DNA site, which are caused by the use of the DNA modifying enzyme. It is therefore an object of the present invention to provide a method of novel DNA editing, particularly, genome editing, capable of increasing safety by utilizing a cell-endogenous DNA modifying enzyme and avoiding restriction of delivery, and a complex therefor of a nucleic acid sequence-recognizing module and a DNA modifying enzyme-binding module.

Means of Solving the Problems

The present inventors produced a complex in which a nucleic acid sequence-recognizing module targeting the object DNA sequence is imparted with a function to bind to a cell-endogenous DNA modifying enzyme, introduced the complex into the cell, and cultured the cell in the presence of a factor inducing the DNA modifying enzyme. As a result, they successfully introduced a mutation into the target nucleotide sequence of the object gene and the vicinity thereof without using an exogenous DNA modifying enzyme.

The present inventors have conducted further studies based on these findings and completed the present invention. Therefore, the present invention is as described below.

[1] A method for altering a targeted site of a DNA in a cell, comprising a step of stimulating the cell with a factor inducing a DNA modifying enzyme endogenous to the cell, and bringing a complex of a nucleic acid sequence-recognizing module specifically binding to a target nucleotide sequence in a given DNA and a DNA modifying enzyme-binding module bonded to each other into contact with the DNA to convert one or more nucleotides in the targeted site to other one or more nucleotides or delete one or more nucleotides, or insert one or more nucleotides into said targeted site.

[2] The method of [1], wherein the aforementioned targeted site is altered without cleaving at least one of the strands of the aforementioned DNA.

[3] The method of [1] or [2], wherein the aforementioned nucleic acid sequence-recognizing module is selected from the group consisting of a CRISPR-Cas system wherein at least one DNA cleavage ability of Cas is inactivated, a zinc finger motif, a TAL effector and a PPR motif.

[4] The method of any of [1] to [3], wherein the aforementioned nucleic acid sequence-recognizing module is a CRISPR-Cas system wherein at least one DNA cleavage ability of Cas is inactivated.

[5] The method of any of [1] to [4], wherein the aforementioned DNA modifying enzyme-binding module is selected from the group consisting of an antibody against the DNA modifying enzyme, a peptide aptamer against the DNA modifying enzyme and a nucleic acid aptamer against the DNA modifying enzyme.

[6] The method of any of [1] to [4], wherein the aforementioned DNA modifying enzyme-binding module is at least one kind selected from the group consisting of Vif, Bet protein, TopoIIβ, IQGAP2 and ZNF335 and fragments thereof.

[7] The method of any of [1] to [6], wherein a target enzyme of the aforementioned DNA modifying enzyme-binding module is deaminase.

[8] The method of [7], wherein the aforementioned deaminase is a protein belonging to the APOBEC family.

[9] The method of [7] or [8], wherein the complex of the nucleic acid sequence-recognizing module bonded to the DNA modifying enzyme-binding module further comprises a base excision repair inhibitor bonded thereto.

[10] The method of any of [1] to [9], wherein the aforementioned factor inducing the DNA modifying enzyme includes one or more selected from the group consisting of interferon, an inhibitor of succinic acid dehydrogenase and hypoxic condition.

[11] The method of any of [1] to [10], wherein the aforementioned DNA and the aforementioned complex are contacted by introducing a nucleic acid encoding the complex into the aforementioned cell and culturing the cell to cause expression of the complex in the cell.

[12] The method of any of [1] to [11], wherein the cell is stimulated by the factor inducing the DNA modifying enzyme by incubating the cell in the presence of the factor.

[13] The method of any of [1] to [12], wherein the aforementioned cell is a vertebrate cell.

[14] The method of [13], wherein the aforementioned vertebrata cell is a mammalian cell.

[15] The method of any of [1] to [14], wherein the aforementioned DNA is a double stranded DNA.

[16] A complex of a nucleic acid sequence-recognizing module specifically binding to a target nucleotide sequence in a DNA and a DNA modifying enzyme-binding module bonded to each other, wherein the nucleic acid sequence-recognizing module is a CRISPR-Cas system wherein at least one DNA cleavage ability of Cas is inactivated, wherein the complex converts one or more nucleotides in the targeted site to other one or more nucleotides or deletes one or more nucleotides, or inserts one or more nucleotides into said targeted site.

[17] A nucleic acid encoding the complex of [16].

[18] An agent for altering a targeted site of a DNA comprising the complex of [16] or the nucleic acid of [17].

[19] A method for altering a targeted site of a double stranded DNA in a cell, comprising a step of stimulating the cell with a factor inducing a DNA modifying enzyme endogenous to the cell, and bringing a nucleic acid sequence-recognizing module specifically binding to a target nucleotide sequence in a given double stranded DNA into contact with the double stranded DNA to convert one or more nucleotides in the targeted site to other one or more nucleotides or delete one or more nucleotides, or insert one or more nucleotides into said targeted site.

Effect of the Invention

According to the DNA editing of the present invention, the risk of side effects is reduced since an exogenous factor is not used in the DNA modification reaction. In addition, delivery efficiency can be improved since the construct used for DNA editing can be miniaturized. Utilizing a cell-endogenous DNA modifying enzyme, moreover, the activity can be controlled by a transient action and the risk of off-target action can be reduced.

BRIEF DESCRIPTION OF THE DRAWINGS

In FIG. 1, IFN is interferon (factor inducing, as antivirus factor, particular defense gene expression), IFN-inducible endogenous deaminase is an antiviral deaminase group (Apobec etc.) showing IFN-induced expression, and dVif (Vif variant) is an adapter protein bonded to endogenous deaminase.

DESCRIPTION OF EMBODIMENTS

Figure 1:
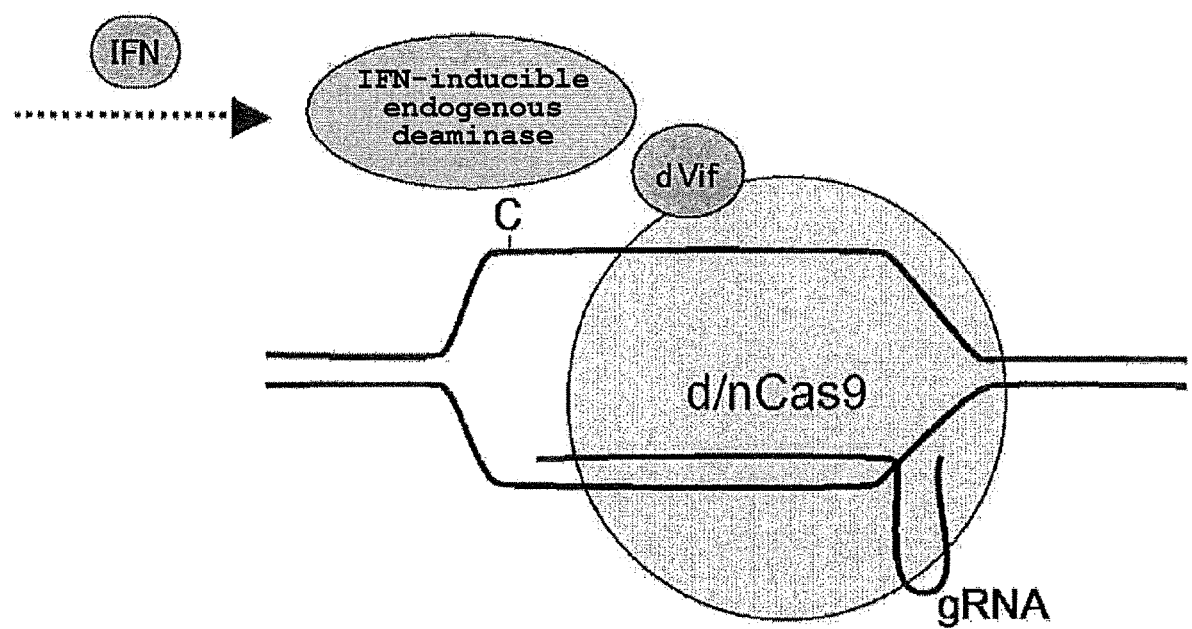
FIG. 1 is a schematic showing of the mechanism of the alteration method of the targeted site of DNA used in the Examples of the present invention.

The present invention provides a method for altering a targeted site in the DNA in a cell by utilizing a DNA modifying enzyme endogenous to the cell (to be also referred to as "cell-endogenous" in the present specification) to convert the target nucleotide sequence and nucleotides in the vicinity thereof in the DNA in the cell to other nucleotides (hereinafter to be also referred to as "the method of the present invention"). As used herein, "endogenous to cell", "cell-endogenous" mean native presence in the cell.

The method of the present invention is characterized by a step in which the cell is stimulated with a factor inducing a cell-endogenous DNA modifying enzyme (hereinafter to be also referred to as "DNA modifying enzyme inducer") and a complex in which a nucleic acid sequence-recognizing module that specifically binds to the target nucleotide sequence in the DNA and a DNA modifying enzyme-binding module are bonded to each other (hereinafter to be also referred to as "the complex of the present invention") is contacted with the DNA in the cell to convert the targeted site, i.e., the target nucleotide sequence and nucleotides in the vicinity thereof, to other nucleotides.

In the present invention, the "alteration" of a DNA means that a nucleotide (e.g., dC) on a DNA strand is converted to other nucleotide (e.g., dT, dA, dG or dU), or deleted, or a nucleotide or a nucleotide sequence is inserted between certain nucleotides on a DNA strand. The DNA to be altered is not particularly limited as long as it is a DNA that the cell has (or present in the cell). It may be a cell-endogenous DNA (e.g., chromosome DNA, mitochondria DNA, chloroplast DNA; hereinafter these are also to be comprehensively referred to as "genomic DNA") or an exogenous DNA (e.g., DNA derived from virus infected with cell). The aforementioned DNA may be a single strand DNA or a double stranded DNA, preferably a double stranded DNA. As the double stranded DNA, preferred is genomic DNA. The "targeted site" of a DNA means the whole or partial "target nucleotide sequence", which a nucleic acid sequence-recognizing module specifically recognizes and binds to, or the vicinity of the target nucleotide sequence (one or both of 5' upstream and 3' downstream). The "target nucleotide sequence" means a sequence to which a nucleic acid sequence-recognizing module in the DNA binds.

In the present invention, the "DNA modifying enzyme" means a cell-endogenous enzyme capable of modifying DNA, and the modification directly or indirectly causes alteration of DNA. Examples of such DNA modification reaction include a reaction to cleave single strand or double strand of DNA (hereinafter to be also referred to as "DNA strand cleavage reaction"), a reaction to convert a substituent on the purine or pyrimidine ring of a nucleic acid base to other group or atom, which is a reaction not directly involving cleavage of DNA strand (hereinafter to be also referred to as "nucleic acid base conversion reaction") (e.g., deamination reaction of base), a reaction to hydrolyze N-glycoside linkage of DNA (hereinafter to be also referred to as "base excision reaction") and the like.

In the present invention, the "DNA modifying enzyme inducer" means a molecule that can directly or indirectly increase the expression of cell-endogenous DNA modifying enzyme and/or a factor that can activate the DNA modifying enzyme (including molecule, physicochemical stimulation such as oxygen concentration, light, UV, temperature, acid, alkali and the like, and the like). The DNA modifying enzyme inducer to be used in the method of the present invention is not particularly limited as long as it has such function. Examples thereof include protein (including peptide, hereinafter the same) (e.g., transcription factor, interferon (IFN), interleukin, Mitogen etc.), low-molecular-weight compound and the like. The DNA modifying enzyme inducer used may be commercially available or one produced by a well known method.

Interferon (IFN) is a protein secreted by cells in response to the invasion of foreign substances such as pathogen (particularly virus), tumor cell and the like, and stimulation of cells with IFN induces expression of antiviral proteins (e.g., proteins belonging to APOBEC (apolipoprotein B mRNA-editing enzyme catalytic polypeptide-like) family and the like). The interferon to be used in the present invention is not particularly limited and TYPE I interferon (e.g., IFN-α, IFN-β, IFN-ω, IFN-ε, IFN-κ), TYPE II interferon (e.g., IFN-γ), TYPE III interferon (e.g., IFN-λ) and the like can be mentioned. Particularly, TYPE I interferon is preferable, and IFN-α and IFN-β are preferable. Interferon may be a natural type or a gene recombinant type, or a pegylated interferon in which a macromolecular form such as polyethylene glycol (PEG) or the like is bonded. When interferon is used, the host cell and the organism from which the interferon is derived are preferably the same (e.g., when human cell is used, human interferon is preferably used). An IFN production-inducing factor may also be used. Examples of such factor include (quasi)infection with virus and the like, vaccine, exogenous DNA or RNA, double stranded RNA analogue [poly(I:C)] (e.g., Trapp S1, et al., (2009) J. Virol, 83(2):884-895), interferon gene stimulator, TANK-binding kinase 1 and the like.

Examples of the interleukin to be used in the present invention include IL-2, IL-7, IL-15, IL-27 and the like known to be able to induce proteins belonging to the APOBEC family (hereinafter to be abbreviated as "APOBEC") (particularly, proteins belonging to the APOBEC3 family (hereinafter to be abbreviated as "APOBEC3")), namely, to increase the expression and/or activity of the proteins.

Examples of the mitogen to be used in the present invention include phorbol ester (e.g., phorbol myristate acetate (PMA), phytohemagglutinin (PHA) etc.) known to be able to induce APOBEC (particularly, APOBEC3) (e.g., Stopak S. Kim, et al., (2007) J. Biol Chem., 282(6): 3539-3546; Rose KM1, et al., (2004) J. Biol Chem., 279(40): 41744-41749) and the like.

Examples of the low-molecular-weight compound to be used in the present invention include the compounds described in JP-A-2011-231053, inhibitors of succinic acid dehydrogenase described in WO 2016-164889 (e.g., Atpenin A5, malonate, diazoxide (DZX), malate and oxaloacetate, 3-nitropropionic acid, nitroxyl, carboxin, TTFA etc.) and the like known to be able to induce APOBEC (particularly, APOBEC3).

The DNA modifying enzyme inducer is not limited to these and those of ordinary skill in the art can appropriately use known proteins and compounds, physicochemical stimulation and the like according to the kind of the target DNA modifying enzyme. Only one kind of the DNA modifying enzyme inducer may be used or two or more kinds thereof may be used (e.g., combined use of interferon and inhibitor of succinic acid dehydrogenase, combined use of interferon and hypoxic condition and the like).

The method for stimulating a cell with a DNA modifying enzyme inducer is not particularly limited. For example, a method including incubating the cell in the presence of a DNA modifying enzyme inducer can be mentioned. Specifically, it can be performed by adding a DNA modifying enzyme inducer to a medium or buffer for incubating the cells or, when the factor is a physicochemical stimulation such as hypoxia or the like, by incubating the cells under a condition with the presence of the stimulation. In addition, a method including introduction of a nucleic acid encoding a DNA modifying enzyme inducer (preferably DNA) into the cell and expression of the factor in the cell can be mentioned.

Also, the timing to start stimulation of the cell with a DNA modifying enzyme inducer is not particularly limited. For example, when the intracellular target DNA and the complex of the present invention are contacted by introducing a nucleic acid encoding the complex into the cell, it may be either before, after or simultaneously with the introduction step. In the method of the present invention, the period of DNA modification reaction can be adjusted by adjusting the period of stimulation of the cells with a DNA modifying enzyme inducer. Therefore, editing of the target sequence can be realized efficiently while avoiding the risk of off-target action in the host genome by stimulating the cells with the DNA modifying enzyme inducer for the period of time necessary for DNA modification reaction to occur and alteration of the targeted site to be fixed. From the aspect of easy adjustment of the period for cell stimulation, a method for incubating the cells in the presence of a DNA modifying enzyme inducer (for example, when the DNA modifying enzyme inducer is a protein, a low-molecular-weight compound or the like, a method for adding the factor to a medium or buffer) is preferable. The period for addition to the medium or buffer varies depending on the type of host cell, incubation conditions, the type of DNA modifying enzyme to be targeted, and the like. When the DNA to be modified is endogenous to the cell, about 2-3 days are considered to be necessary since at least several generations of cell division are generally necessary. On the other hand, when the DNA to be modified is exogenous DNA, the period can be shortened as compared with the intracellular DNA since cell division is not generally necessary. Those of ordinary skill in the art can appropriately determine a preferable expression induction period based on the culture conditions and the like to be used.

The content of the DNA modifying enzyme inducer to be added to the medium is not particularly limited as long as the target DNA is altered. When interferon is used as a DNA modifying enzyme inducer, it is added to the medium at preferably 10-100000 IU (international unit), more preferably 100-20000 IU, further preferably 500-5000 IU. When Aptenin A5 is used as a DNA modifying enzyme inducer, it is added to the medium at preferably 0.5 μM-10 μM, more preferably 1 μM-3 μM. Those of ordinary skill in the art can appropriately determine a preferable content, titer, and the like based on the DNA modifying enzyme inducer to be used, cell type, culture conditions and the like.

When a DNA modifying enzyme inducer is a physicochemical stimulation, one preferable embodiment is a hypoxic condition. For example, it has been reported that proteins belonging to the APOBEC family can be activated when exposed to hypoxic conditions (e.g., WO 2016-164889). Examples of the method for exposing cells to hypoxic conditions include a method for incubating cells in a hypoxic state atmosphere and the like. Here, the "hypoxic state" means that the oxygen concentration is lower than the oxygen concentration in the atmosphere. Examples of such oxygen concentration include not more than 15%, preferably not more than 10%, more preferably not more than 5%, further preferably not more than 1%, and preferably not less than 0.1%.

Alternatively, when a nucleic acid (preferably DNA) encoding a DNA modifying enzyme inducer is introduced into a cell and the factor is expressed in the cell, it can be introduced into a cell in the same manner as a nucleic acid encoding the below-mentioned nucleic acid sequence-recognizing module and/or DNA modifying enzyme-binding module. When a DNA encoding a DNA modifying enzyme inducer is used, the DNA is placed under the control of an inducible regulatory region, substances capable of activating the regulatory region is added to and/or removed from the medium or buffer in which the cells are incubated to adjust the expression period of the DNA modifying enzyme inducer in the cell, whereby the period during which the DNA modification reaction occurs can be adjusted. As the "inducible regulatory region", the regulatory region described later for regulation of the expression of the nucleic acid encoding the complex of the present invention can be used similarly.

In the present invention, the "nucleic acid sequence-recognizing module" means a molecule or molecule complex having an ability to specifically recognize and bind to a particular nucleotide sequence (i.e., target nucleotide sequence) on a DNA strand. Binding of the nucleic acid sequence-recognizing module to a target nucleotide sequence enables cell-endogenous DNA modifying enzyme to specifically act on a targeted site of a DNA via DNA modifying enzyme-binding module linked to said module.

In the present invention, the "DNA modifying enzyme-binding module" means a molecule or molecule complex having the ability to bind to a DNA modifying enzyme.

The complex of the present invention is a molecular complex containing a complex in which the above-mentioned nucleic acid sequence-recognizing module and DNA modifying enzyme-binding module are linked, and provided with specific nucleotide sequence recognition ability and a cell-endogenous DNA modifying enzyme. The "complex" here encompasses not only one constituted of multiple molecules, but also one having a nucleic acid sequence-recognizing module and DNA modifying enzyme-binding module in a single molecule, like a fusion protein.

In the present invention, the cell-endogenous DNA modifying enzyme as a binding target of a DNA modifying enzyme-binding module (hereinafter to be also referred to as "target enzyme") is not particularly limited. Examples thereof include nuclease (e.g., endonuclease, exonuclease etc.), recombinase, DNA gyrase, DNA polymerase, DNA topoisomerase, telomerase, transposase, deaminase, DNA glycosylase and the like. From the viewpoint of reduced cytotoxicity, alteration of DNA is preferably performed not by a cleavage reaction of strand of double stranded DNA, but by a reaction that does not cleave at least one strand of double stranded DNA (e.g., nucleic acid base conversion reaction and base excision reaction on DNA). Examples of the DNA modifying enzyme that catalyzes nucleic acid base conversion reaction and base excision reaction include deaminase belonging to the nucleic acid/nucleotide deaminase superfamily that catalyzes a deamination reaction to convert an amino group to a carbonyl group, DNA glycosylase that catalyzes hydrolysis of N-glycoside linkage of DNA (e.g., thymine DNA glycosylase, oxoguanine glycosylase, alkyladenine DNA glycosylase (e.g., yeast 3-methyladenine-DNA glycosylase (MAGI)) and the like) and the like. Preferable examples of deaminase include cytidine deaminase capable of converting cytosine or 5-methylcytosine to uracil or thymine, respectively, adenosine deaminase capable of converting adenine to hypoxanthine, guanosine deaminase capable of converting guanine to xanthine and the like. As cytidine deaminase, more preferred is APOBEC. In human, APOBEC includes APOBEC1, APOBEC2, APOBEC3 (e.g., APOBEC3A, APOBEC3B, APOBEC3C, APOBEC3D(APOBEC3E), APOBEC3F, APOBEC3G, APOBEC3H), APOBEC4, activation-induced cytidine deaminase (AID) which is an enzyme that introduces a mutation into an immunoglobulin gene in the acquired immunity of vertebrate and the like.

The DNA modifying enzyme-binding module used in the method of the present invention is not particularly limited as long as it can bind to the cell-endogenous DNA modifying enzyme mentioned above. Examples thereof include antibody, peptide aptamer, nucleic acid aptamer against the target DNA modifying enzyme, proteins that bind to other DNA modifying enzymes and the like. The DNA modifying enzyme-binding module can be appropriately selected according to the type of target DNA modifying enzyme. As these DNA modifying enzyme-binding modules, those known to bind to the target DNA modifying enzyme may be used, or molecules produced by the method described below may be used. The DNA encoding the DNA modifying enzyme-binding module can be appropriately produced based on the information of the amino acid sequence, nucleic acid sequence of the object DNA modifying enzyme-binding module.

The antibody used in the method of the present invention may be either a polyclonal antibody or a monoclonal antibody, and the antibody also encompasses antibody fragments (e.g., F(ab')$_2$, Fab', Fab, Fv, scFv etc.). The antibody can be produced by a well-known immunological method. Peptide aptamer is an aptamer composed of an amino acid and is a peptide molecule that can bind to a specific target molecule, similar to antibodies. The peptide aptamer can be screened for or produced based on a phage display method and a cell surface layer display method (e.g., Whaley, S. R., et al., (2000), Nature, 405, 665-668). The nucleic acid aptamer is an aptamer constituted of RNA, DNA, modified nucleotide or a mixture thereof. The aptamer can be screened for or produced according to well-known methods (e.g., Ellington et al., (1990), Nature, 346,818-822; Tuerk et al., (1990) Science, 249, 505-510).

Examples of the protein that binds to a DNA modifying enzyme include, but are not limited to, Vif (Virion Infectivity Factor) of human immunodeficiency virus (HIV) and monkey immunodeficiency virus (SIVmac) known to bind to APOBEC (particularly, APOBEC3), Bet (Bromodomain and extra-terminal) protein of foamy virus, TopoIIβ (Topoisomerase 2-beta), IQGAP2, ZNF335 (aka: NIF1), CD81, MLL, C-terminal (196th-384th amino acid residues) of APOBEC3G (e.g., Schumacher, April Jean, Ph.D., UNIVERSITY OF MINNESOTA, (2008) 199, pages; 3313466), fragments of these (in the following, unless otherwise specified, protein encompasses fragments thereof) and the like. These proteins may be altered (altered protein is sometimes referred to as a "variant" of protein). For example, when Vif is used, since Vif is known to bind to an E3 ubiquitin ligase complex and promote proteolysis of APOBEC3 (e.g., Stanley et al. (2008) Journal of virology, 8656-8663; Guo et al. (2014) Nature, 55, 229-233), it is preferable to apply alteration that causes lack of bindability to proteins other than APOBEC3. Examples of such alteration include deletion of several (e.g., 11, 10, 9, 8, 7 etc.) amino acids in the N terminal of Vif protein (refseq No.: AAF20197) and substitution of the 145th leucine residue with other amino acid residue (e.g., alanine residue) and the like, but they are not limited to these alterations. Even when a protein other than Vif is used, it can be appropriately modified based on the function of the protein, binding site with the target molecule, three-dimensional structure, and the like. The above-mentioned protein fragment is not particularly limited as long as it has a binding region to the DNA modifying enzyme. For example, a fragment excluding a region other than the binding region to the DNA modifying enzyme (e.g., region having protein catalytic activity) can be mentioned. Specific examples of such fragment include a peptide composed of the 452nd-591st amino acid residues of TopoIIβ (refseq No.: NP_001059), a peptide composed of the 466th-547th amino acid residues of IQGAP2 (refseq No.: NP_006624), a peptide composed of the 745th-893rd amino acid residues of ZNF335 (refseq No.: NP_071378) and the like. These are mere examples, and those skilled in the art can appropriately design fragments. As shown in the below-mentioned Examples, the targeted site is also altered when IQGAP2 and ZNF335 are combined (Table 2). Accordingly, proteins that bind to the aforementioned DNA modifying enzyme can also be used in combination.

In the present invention, the "base excision repair" is one of the DNA repair mechanisms of living organisms, and means a mechanism for repairing damages of bases by cutting off damaged parts of the bases by enzymes and rejoining them. Excision of damaged bases is performed by DNA glycosylase, which is an enzyme that hydrolyzes the N-glycoside linkage of DNA. An abasic site (apurinic/apyrimidic (AP) site) resulting from the abasic reaction by the enzyme is treated by an enzyme at the downstream of the base excision repair (BER) pathway such as AP endonuclease, DNA polymerase, DNA ligase and the like. Examples of such gene or protein involved in the BER pathway include, but are not limited to, UNG (NM 003362), SMUG1 (NM_014311), MBD4 (NM_003925), TDG (NM_003211), OGG1 (NM_002542), MYH (NM_012222), NTHL1 (NM_002528), MPG (NM_002434), NEIL1 (NM_024608), NEIL2 (NM_145043), NEIL3 (NM_018248), APE1 (NM_001641), APE2 (NM_014481), LIG3 (NM_013975), XRCC1 (NM_006297), ADPRT (PARP1) (NM_0016718), ADPRTL2 (PARP2) (NM_005484) and the like (parentheses indicate refseq number in which the base sequence information of each gene (cDNA) is registered).

In the present invention, the "base excision repair inhibitor" means a substance that inhibits any stage of the above-mentioned BER pathway, or a substance that eventually inhibits BER by inhibiting the expression of molecules mobilized in the BER pathway. While the base excision repair inhibitor to be used in the present invention is not particularly limited as long as it consequently inhibits BER, from the aspect of efficiency, an inhibitor of DNA glycosylase located at the upstream of the BER pathway is preferable. Examples of the inhibitor of DNA glycosylase to be used in the present invention include, but are not limited to, a thymine DNA glycosylase inhibitor, an uracil DNA glycosylase inhibitor, an oxoguanine DNA glycosylase inhibitor, an alkylguanine DNA glycosylase inhibitor and the like. For example, when the target enzyme of a DNA modifying enzyme-binding module is cytidine deaminase, it is suitable to use a uracil DNA glycosylase inhibitor to inhibit repair of U:G or G:U mismatch of DNA generated by mutation.

Examples of such uracil DNA glycosylase inhibitor include, but are not limited to, a uracil DNA glycosylase inhibitor (Ugi) derived from *Bacillus subtilis* bacteriophage, PBS1, and a uracil DNA glycosylase inhibitor (Ugi) derived from *Bacillus subtilis* bacteriophage, PBS2 (Wang, Z., and Mosbaugh, D. W. (1988) J. Bacteriol. 170, 1082-1091). The above-mentioned inhibitor of the repair of DNA mismatch can be used in the present invention. Particularly, Ugi derived from PBS2 is also known to have an effect of making it difficult to cause mutation, cleavage and recombination other than T from C on DNA, and thus the use of Ugi derived from PBS2 is suitable.

As mentioned above, in the base excision repair (BER) mechanism, when a base is excised by DNA glycosylase, AP endonuclease puts a nick in the abasic site (AP site), and exonuclease completely excises the AP site. When the AP site is excised, DNA polymerase produces a new base by using the base of the opposing strand as a template, and DNA ligase finally seals the nick to complete the repair. Mutant AP endonuclease that has lost the enzyme activity but maintains the binding capacity to the AP site is known to competitively inhibit BER. Therefore, these mutation AP endonucleases can also be used as the base excision repair inhibitor in the present invention. While the derivation of the mutant AP endonuclease is not particularly limited, for example, AP endonucleases derived from *Escherichia coli*, yeast, mammal (e.g., human, mouse, swine, bovine, horse, monkey etc.) and the like can be used. For example, UniprotKB No. P27695 can be referred to for the amino acid sequence of human Ape1. Examples of the mutant AP endonuclease that has lost the enzyme activity but maintains the binding capacity to the AP site include proteins having mutated activity site and mutated Mg (cofactor)-binding site. For example, E96Q, Y171A, Y171F, Y171H, D210N, D210A, N212A and the like can be mentioned for human Ape1.

A target nucleotide sequence in a DNA to be recognized by the nucleic acid sequence-recognizing module in the complex of the present invention is not particularly limited as long as the module specifically binds to, and may be any sequence in the DNA. The length of the target nucleotide sequence only needs to be sufficient for specific binding of the nucleic acid sequence-recognizing module. For example, it is not less than 12 nucleotides, preferably not less than 15 nucleotides, more preferably not less than 18 nucleotides, according to the size of the target DNA. While the upper limit of the length is not particularly limited, it is preferably not more than 25 nucleotides, more preferably not more than 22 nucleotides.

As the nucleic acid sequence-recognizing module in the complex of the present invention, CRISPR-Cas system wherein at least one DNA cleavage ability of Cas is inactivated (hereinafter to be also referred to as "CRISPR-mutant Cas"), zinc finger motif, TAL effector and PPR motif and the like, as well as a fragment containing a DNA binding domain of a protein that specifically binds to DNA, such as restriction enzyme, transcription factor, RNA polymerase and the like, and free of a DNA double strand cleavage ability and the like can be used, but the module is not limited thereto. Preferably, CRISPR-mutant Cas, zinc finger motif, TAL effector, PPR motif and the like can be mentioned.

A zinc finger motif is constituted by linkage of 3-6 different Cys2His2 type zinc finger units (1 finger recognizes about 3 bases), and can recognize a target nucleotide sequence of 9-18 bases. A zinc finger motif can be produced by a known method such as Modular assembly method (Nat Biotechnol (2002) 20: 135-141), OPEN method (Mol Cell (2008) 31: 294-301), CoDA method (Nat Methods (2011) 8: 67-69), *Escherichia coli* one-hybrid method (Nat Biotechnol (2008) 26:695-701) and the like. The above-mentioned patent document 1 can be referred to as for the detail of the zinc finger motif production.

A TAL effector has a module repeat structure with about 34 amino acids as a unit, and the 12th and 13th amino acid residues (called RVD) of one module determine the binding stability and base specificity. Since each module is highly independent, TAL effector specific to a target nucleotide sequence can be produced by simply connecting the module. For TAL effector, a production method utilizing an open resource (REAL method (Curr Protoc Mol Biol (2012) Chapter 12: Unit 12.15), FLASH method (Nat Biotechnol (2012) 30: 460-465), and Golden Gate method (Nucleic Acids Res (2011) 39: e82) etc.) have been established, and a TAL effector for a target nucleotide sequence can be designed comparatively conveniently. The above-mentioned patent document 2 can be referred to as for the detail of the production of TAL effector.

PPR motif is constituted such that a particular nucleotide sequence is recognized by a continuation of PPR motifs each consisting of 35 amino acids and recognizing one nucleic acid base, and recognizes a target base only by 1, 4 and ii(-2) amino acids of each motif. Motif constituent has no dependency, and is free of interference of motifs on both sides. Therefore, like TAL effector, a PPR protein specific to the target nucleotide sequence can be produced by simply connecting PPR motifs. The above-mentioned patent document 4 can be referred to as for the detail of the production of PPR motif.

When a fragment of restriction enzyme, transcription factor, RNA polymerase and the like is used, since the DNA binding domains of these proteins are well known, a fragment containing the domain and free of a DNA double strand cleavage ability can be easily designed and constructed.

Any of the above-mentioned nucleic acid sequence-recognizing modules can be provided as a fusion protein with the above-mentioned DNA modifying enzyme-binding module when it is a protein, or a protein binding domain such as SH3 domain, PDZ domain, GK domain, GB domain and the like and a binding partner thereof may be fused with a nucleic acid sequence-recognizing module and a DNA modifying enzyme-binding module, respectively, and provided as a protein complex via an interaction of the domain and a binding partner thereof. Alternatively, a nucleic acid sequence-recognizing module and a DNA modifying enzyme-binding module may be each fused with intein, and they can be linked by ligation after protein synthesis.

The complex of the present invention containing a complex (including fusion protein) wherein a nucleic acid sequence-recognizing module and DNA modifying enzyme-binding module are bonded is desirably contacted with a DNA (e.g., genomic DNA) by introducing a nucleic acid encoding the complex into a cell having the object DNA.

Therefore, the nucleic acid sequence-recognizing module and the DNA modifying enzyme-binding module are preferably prepared as a nucleic acid encoding a fusion protein thereof, or in a form capable of forming a complex in a host cell after translation into a protein by utilizing a binding domain, intein and the like, or as a nucleic acid encoding each of them. The nucleic acid here may be a DNA or an RNA, preferably DNA. When it is a DNA, it is preferably a double-stranded DNA, and provided in the form of an expression vector disposed under regulation of a functional promoter in a host cell.

The complex of the present invention wherein a nucleic acid sequence-recognizing module and a DNA modifying enzyme-binding module are bonded permits DNA editing with low toxicity is possible, and the genetic alteration method of the present invention can be applied to a wide range of biological materials. Therefore, the cells to be introduced with nucleic acid encoding nucleic acid sequence-recognizing module and/or DNA modifying enzyme-binding module can encompass cells of any species, from bacterium of *Escherichia coli* and the like which are prokaryotes, cells of microorganism such as yeast and the like which are lower eucaryotes, to cells of vertebrate including mammals such as human and the like, and cells of higher eukaryote such as insect, plant and the like.

A DNA encoding a nucleic acid sequence-recognizing module such as zinc finger motif, TAL effector, PPR motif and the like can be obtained by any method mentioned above for each module. A DNA encoding a sequence-recognizing module of restriction enzyme, transcription factor, RNA polymerase and the like can be cloned by, for example, synthesizing an oligoDNA primer covering a region encoding a desired part of the protein (i.e., part containing DNA binding domain) based on the cDNA sequence information thereof, and amplifying by the RT-PCR method using, as a template, the total RNA or mRNA fraction prepared from the protein-producing cells.

A DNA encoding DNA modifying enzyme-binding module, DNA modifying enzyme inducer or base excision repair inhibitor can also be cloned similarly by synthesizing an oligoDNA primer based on the cDNA sequence information of the protein and the like to be used, and amplifying by the RT-PCR method using, as a template, the total RNA or mRNA fraction prepared from the protein and the like. For example, when Vif of HIV is used as a DNA modifying enzyme-binding module, a DNA encoding the protein can be cloned by designing suitable primers for the upstream and downstream of CDS based on the cDNA sequence (accession No. AF200477) registered in the NCBI database, and performing cloning according to the RT-PCR method from RNA extracted from a cell infected with HIV.

The cloned DNA may be directly, or after digestion with a restriction enzyme when desired, or after addition of a suitable linker and/or a nuclear localization signal (each organelle localization signal when the object DNA is mitochondria or chloroplast DNA), ligated with a DNA encoding a nucleic acid sequence-recognizing module to prepare a DNA encoding a fusion protein. When a nucleic acid sequence-recognizing module and a DNA modifying enzyme-binding module are expressed as a fusion protein, for example, a nuclear localization signal can be added to the both terminals of the fusion protein, or between the nucleic acid sequence-recognizing module and the DNA modifying enzyme-binding module. The nuclear localization signal is not particularly limited and, for example, SV40-derived nuclear localization signal (e.g., SEQ ID NO: 7, SEQ ID NO: 9) can be mentioned.

Alternatively, a DNA encoding a nucleic acid sequence-recognizing module, and a DNA encoding a DNA modifying enzyme-binding module may be each fused with a DNA encoding a binding domain or a binding partner thereof, or respective DNAs may be fused with a DNA encoding a separation intein, whereby the nucleic acid sequence-recognizing module and the DNA modifying enzyme-binding module are translated in a host cell to form a complex. In these cases, a linker and/or a nuclear localization signal can be linked to a suitable position of respective DNAs when desired.

A DNA encoding nucleic acid sequence-recognizing module and a DNA encoding DNA modifying enzyme-binding module (and a DNA encoding DNA modifying enzyme inducer when cells are stimulated by introducing and expressing DNA encoding the inducer in the cell; hereinafter the same when indicated in parentheses) can be obtained by chemically synthesizing the DNA strand, or by connecting synthesized partly overlapping oligoDNA short strands by utilizing the PCR method and the Gibson Assembly method to construct a DNA encoding the full length thereof. The advantage of constructing a full-length DNA by chemical synthesis or a combination of PCR method or Gibson Assembly method is that the codon to be used can be designed in CDS full-length according to the host into which the DNA is introduced. In the expression of a heterologous DNA, the protein expression level is expected to increase by converting the DNA sequence thereof to a codon highly frequently used in the host organism. As the data of codon use frequency in host to be used, for example, the genetic code use frequency database (http://www.kazusa.or.jp/codon/index.html) disclosed in the home page of Kazusa DNA Research Institute can be used, or documents showing the codon use frequency in each host may be referred to. By reference to the obtained data and the DNA sequence to be introduced, codons showing low use frequency in the host from among those used for the DNA sequence may be converted to a codon coding the same amino acid and showing high use frequency. For example, when the host cell is a human cell, a nucleic acid sequence-recognizing module and/or a sequence encoding a DNA modifying enzyme-binding module which are/is optimized for use of human codon can be used. A DNA encoding a base excision repair inhibitor can also be constructed similarly.

An expression vector containing a DNA encoding nucleic acid sequence-recognizing module and/or a DNA encoding DNA modifying enzyme-binding module (and/or a DNA encoding a DNA modifying enzyme inducer) can be produced, for example, by linking the DNA to the downstream of a promoter in a suitable expression vector. Furthermore, the aforementioned expression vector can also be produced including a DNA encoding a base excision repair inhibitor.

As the expression vector, *Escherichia coli*-derived plasmids (e.g., pBR322, pBR325, pUC12, pUC13); *Bacillus subtilis*-derived plasmids (e.g., pUB110, pTP5, pC194); yeast-derived plasmids (e.g., pSH19, pSH15); insect cell expression plasmids (e.g., pFast-Bac); animal cell expression plasmids (e.g., pA1-11, pXT1, pRc/CMV, pRc/RSV, pcDNAI/Neo); bacteriophages such as λphage and the like; insect virus vectors such as baculovirus and the like (e.g., BmNPV, AcNPV); animal virus vectors such as retrovirus, vaccinia virus, adenovirus and the like, and the like are used.

As the promoter, any promoter appropriate for a host to be used for gene expression can be used. In a conventional method accompanying DSB, since the survival rate of the host cell sometimes decreases markedly due to the toxicity, it is desirable to increase the number of cells by the start of the induction by using an inductive promoter. When an enzyme unaccompanied by DSB is induced as a cell-endogenous DNA modifying enzyme, since sufficient cell proliferation can also be expected by expressing the complex of the present invention, a constituent promoter can also be used without limitation.

For example, when the host is an animal cell, SRα promoter, SV40 promoter, LTR promoter, CMV (cytomegalovirus) promoter, RSV (Rous sarcoma virus) promoter, MoMuLV (Moloney mouse leukemia virus) LTR, HSV-TK (simple herpes virus thymidine kinase) promoter and the like are used. Of these, CMV promoter, SRα promoter and the like are preferable.

When the host is *Escherichia coli*, trp promoter, lac promoter, recA promoter, λ$P_L$ promoter, lpp promoter, T7 promoter and the like are preferable.

When the host is genus *Bacillus*, SPO1 promoter, SPO2 promoter, penP promoter and the like are preferable.

When the host is a yeast, Gall/10 promoter, PHO5 promoter, PGK promoter, GAP promoter, ADH promoter and the like are preferable.

When the host is an insect cell, polyhedrin promoter, P10 promoter and the like are preferable.

When the host is a plant cell, CaMV35S promoter, CaMV19S promoter, NOS promoter and the like are preferable.

When desired, the expression vector can contain a terminator (e.g., NOS terminator, *Pisum sativum* rbcS3A terminator, heat shock protein (HSP)17.3 terminator etc.), a translation enhancer (e.g., rice derived from alcoholdehydrogenase 5' untranslated region (Os ADH-5'UTR), CaMV or tobacco mosaic virus (TMV)-derived Ω sequence etc.), a 3' regulatory region (e.g., rice derived from actin gene (Act1)3'UTR etc.), poly A added signal, a selection marker of a drug resistance gene (e.g., G418 resistance gene (nPtII), hygromycin resistance gene (hpt) etc.) and the like.

An RNA encoding a nucleic acid sequence-recognizing module and/or an RNA encoding a DNA modifying enzyme-binding module (and/or an RNA encoding DNA modifying enzyme inducer) can be prepared by, for example, transcription to mRNA in vitro transcription system known per se by using the above-mentioned expression vector containing a DNA encoding nucleic acid sequence-recognizing module and/or a DNA encoding DNA modifying enzyme-binding module (and/or a DNA encoding DNA modifying enzyme inducer) as a template. RNA encoding a base excision repair inhibitor can be prepared similarly.

A complex of a nucleic acid sequence-recognizing module and a DNA modifying enzyme-binding module can be intracellularly expressed by introducing an expression vector containing a DNA encoding a nucleic acid sequence-recognizing module and/or a DNA modifying enzyme-binding module into a host cell, and culturing the host cell.

As the host, genus *Escherichia*, genus *Bacillus*, yeast, insect cell, insect, animal cell and the like are used.

As the genus *Escherichia, Escherichia coli* K12.DH1 [Proc. Natl. Acad. Sci. USA, 60, 160 (1968)], *Escherichia coli* JM103 [Nucleic Acids Research, 9, 309 (1981)], *Escherichia coli* JA221 [Journal of Molecular Biology, 120, 517 (1978)], *Escherichia coli* HB101 [Journal of Molecular Biology, 41, 459 (1969)], *Escherichia coli* C600 [Genetics, 39, 440 (1954)] and the like are used.

As the genus *Bacillus, Bacillus subtilis* M1114 [Gene, 24, 255 (1983)], *Bacillus subtilis* 207-21 [Journal of Biochemistry, 95, 87 (1984)] and the like are used.

As the yeast, *Saccharomyces cerevisiae* AH22, AH22R⁻, NA87-11A, DKD-5D, 20B-12, *Schizosaccharomyces pombe* NCYC1913, NCYC2036, *Pichia pastoris* KM71 and the like are used.

As the insect cell when the virus is AcNPV, cells of cabbage armyworm larva-derived established line (*Spodoptera frugiperda* cell; Sf cell), MG1 cells derived from the mid-intestine of *Trichoplusia ni*, High Five™ cells derived from an egg of *Trichoplusia ni, Mamestra brassicae*-derived cells, *Estigmena acrea*-derived cells and the like are used. When the virus is BmNPV, cells of *Bombyx mori*-derived established line (*Bombyx mori* N cell; BmN cell) and the like are used as insecT cells. As the Sf cell, for example, Sf9 cell (ATCC CRL1711), Sf21 cell [all above, In Vivo, 13, 213-217 (1977)] and the like are used.

As the insect, for example, larva of *Bombyx mori, Drosophila*, cricket and the like are used [Nature, 315, 592 (1985)].

As the animal cell, cell lines such as monkey COS-7 cell, monkey Vero cell, Chinese hamster ovary (CHO) cell, dhfr gene-deficient CHO cell, mouse L cell, mouse AtT-20 cell, mouse myeloma cell, rat GH3 cell, human fetal kidney-derived cells (e.g., HEK293 cell), cell derived from human liver cancer (e.g., HepG2), human FL cell and the like, pluripotent stem cells such as iPS cell, ES cell and the like of human and other mammals, and primary cultured cells prepared from various tissues are used. Furthermore, zebrafish embryo, *Xenopus* oocyte and the like can also be used.

As the plant cell, suspend cultured cells, callus, protoplast, leaf segment, root segment and the like prepared from various plants (e.g., grain such as rice, wheat, corn and the like, product crops such as tomato, cucumber, egg plant and the like, garden plants such as carnation, *Eustoma russellianum* and the like, experiment plants such as tobacco, *Arabidopsis thaliana* and the like, and the like) are used.

All the above-mentioned host cells may be haploid (monoploid), or polyploid (e.g., diploid, triploid, tetraploid and the like). In the conventional mutation introduction methods, mutation is, in principle, introduced into only one homologous chromosome to produce a hetero gene type. Therefore, desired phenotype is not expressed unless dominant mutation occurs, and homozygousness inconveniently requires labor and time. In contrast, according to the present invention, since mutation may be introduced into any allele on the homologous chromosome in the genome when the target DNA is altered by the method of the present invention using a CRISPR-mutation Cas including nucleic acid sequence-recognizing module, desired phenotype can be expressed in a single generation even in the case of recessive mutation, which can solve the problem of the conventional method.

An expression vector can be introduced by a known method (e.g., lysozyme method, competent method, PEG method, $CaCl_2$ coprecipitation method, electroporation method, the microinjection method, the particle gun method, lipofection method, *Agrobacterium* method and the like) according to the kind of the host.

*Escherichia coli* can be transformed according to the methods described in, for example, Proc. Natl. Acad. Sci. USA, 69, 2110 (1972), Gene, 17, 107 (1982) and the like.

The genus *Bacillus* can be introduced into a vector according to the methods described in, for example, Molecular & General Genetics, 168, 111 (1979) and the like.

A yeast can be introduced into a vector according to the methods described in, for example, Methods in Enzymology, 194, 182-187 (1991), Proc. Natl. Acad. Sci. USA, 75, 1929 (1978) and the like.

An insect cell and an insect can be introduced into a vector according to the methods described in, for example, Bio/Technology, 6, 47-55 (1988) and the like.

An animal cell can be introduced into a vector according to the methods described in, for example, Cell Engineering additional volume 8, New Cell Engineering Experiment Protocol, 263-267 (1995) (published by Shujunsha), and Virology, 52, 456 (1973).

A cell introduced with a vector can be cultured according to a known method according to the kind of the host.

For example, when *Escherichia coli* or genus *Bacillus* is cultured, a liquid medium is preferable as a medium to be used for the culture. The medium preferably contains a carbon source, nitrogen source, inorganic substance and the like necessary for the growth of the transformant. Examples of the carbon source include glucose, dextrin, soluble starch, sucrose and the like; examples of the nitrogen source include inorganic or organic substances such as ammonium salts, nitrate salts, corn steep liquor, peptone, casein, meat extract, soybean cake, potato extract and the like; and examples of the inorganic substance include calcium chloride, sodium dihydrogen phosphate, magnesium chloride and the like. The medium may contain yeast extract, vitamins, growth promoting factor and the like. The pH of the medium is preferably about 5-about 8.

As a medium for culturing *Escherichia coli*, for example, M9 medium containing glucose, casamino acid [Journal of Experiments in Molecular Genetics, 431-433, Cold Spring Harbor Laboratory, New York 1972] is preferable. Where necessary, for example, agents such as 3β-indolylacrylic acid may be added to the medium to ensure an efficient function of a promoter. *Escherichia coli* is cultured at generally about 15-about 43° C. Where necessary, aeration and stirring may be performed.

The genus *Bacillus* is cultured at generally about 30-about 40° C. Where necessary, aeration and stirring may be performed.

Examples of the medium for culturing yeast include Burkholder minimum medium [Proc. Natl. Acad. Sci. USA, 77, 4505 (1980)], SD medium containing 0.5% casamino acid [Proc. Natl. Acad. Sci. USA, 81, 5330 (1984)] and the like. The pH of the medium is preferably about 5-about 8. The culture is performed at generally about 20° C.-about 35° C. Where necessary, aeration and stirring may be performed.

As a medium for culturing an insect cell or insect, for example, Grace's Insect Medium [Nature, 195, 788 (1962)] containing an additive such as inactivated 10% bovine serum and the like as appropriate and the like are used. The pH of the medium is preferably about 6.2-about 6.4. The culture is performed at generally about 27° C. Where necessary, aeration and stirring may be performed.

As a medium for culturing an animal cell, for example, minimum essential medium (MEM) containing about 5-about 20% of fetal bovine serum [Science, 122, 501 (1952)], Dulbecco's modified Eagle medium (DMEM) [Virology, 8, 396 (1959)], RPMI 1640 medium [The Journal of the American Medical Association, 199, 519 (1967)], 199 medium [Proceeding of the Society for the Biological Medicine, 73, 1 (1950)] and the like are used. The pH of the medium is preferably about 6-about 8. The culture is performed at generally about 30°-about 40° C. Where necessary, aeration and stirring may be performed.

As a medium for culturing a plant cell, for example, MS medium, LS medium, B5 medium and the like are used. The pH of the medium is preferably about 5-about 8. The culture is performed at generally about 20° C.-about 30° C. Where necessary, aeration and stirring may be performed.

As mentioned above, a complex of a nucleic acid sequence-recognizing module and a DNA modifying enzyme-binding module, i.e., the complex of the present invention, can be expressed intracellularly.

An RNA encoding a nucleic acid sequence-recognizing module and/or DNA modifying enzyme-binding module can be introduced into a host cell by microinjection method, lipofection method and the like. RNA introduction can be performed once or repeated multiple times (e.g., 2-5 times) at suitable intervals.

When a complex of a nucleic acid sequence-recognizing module and a DNA modifying enzyme-binding module is expressed by an expression vector introduced into the cell, the nucleic acid sequence-recognizing module specifically recognizes and binds to a target nucleotide sequence in the DNA (e.g., genomic DNA) of interest. A DNA modifying enzyme-binding module linked to the nucleic acid sequence-recognizing module binds to a cell-endogenous DNA modifying enzyme induced by stimulation by a DNA modifying enzyme inducer, and DNA strand or base is modified in the targeted site (whole or partial target nucleotide sequence or the vicinity thereof) by the action of the DNA modifying enzyme.

When the target DNA is double stranded, modification of DNA occurs in the sense strand or antisense strand in the targeted site. When the modification of DNA is cleavage of DNA strand, various mutations are introduced during repair by the repair mechanism such as base excision repair (BER), nucleotide excision repair (NER), single strand cleavage repair, non-homologous end-joining (NHEJ), homologous recombination (HR) and the like. When the modification of DNA does not directly accompany cleavage of DNA strand, a mismatch or site free of base is produced in the double stranded DNA (AP moiety) (apurinic/apyrimidic (AP) site), mutations are introduced in the process of repairing same. For example, when a DNA modifying enzyme-binding module capable of binding to cytidine deaminase such as APOBEC and the like is used, cytosine on the sense strand or antisense strand at the targeted site is converted to uracil to cause U:G or G:U mismatch). When the mismatch is not correctly repaired, and when repaired such that a base of the opposite strand forms a pair with a base of the converted strand (T-A or A-T in the above-mentioned example), or when other nucleotide is further substituted (e.g., U-A, G) or when one to several dozen bases are deleted or inserted during repair, various mutations are introduced. For example, when a DNA modifying enzyme-binding module capable of binding to DNA glycosylase is used, base excision reaction occurs in the sense strand or antisense strand of the targeted site, and an abasic site (AP site) is produced in one of the strands of the double stranded DNA. Then, the base excision repair (BER) system in the cell operates, AP endonuclease first recognizes the AP site and cleaves the phosphoric acid bond in one of DNA strand, and exonuclease removes nucleotide subjected to base excision. Then, DNA polymerase inserts a new nucleotide by using the opposing strand DNA as a template and finally DNA ligase repairs the joint. Various mutations are introduced by a repair miss occurring at any stage of this BER.

As for zinc finger motif, production of many actually functionable zinc finger motifs is not easy, since production efficiency of a zinc finger that specifically binds to a target nucleotide sequence is not high and selection of a zinc finger having high binding specificity is complicated. While TAL effector and PPR motif have a high degree of freedom of target nucleic acid sequence recognition as compared to zinc finger motif, a problem remains in the efficiency since a large protein needs to be designed and constructed every time according to the target nucleotide sequence.

In contrast, since the CRISPR-Cas system recognizes the object DNA sequence by a guide RNA complementary to the target nucleotide sequence, any sequence can be targeted by simply synthesizing an oligoDNA capable of specifically forming a hybrid with the target nucleotide sequence.

Therefore, in a more preferable embodiment of the present invention, a CRISPR-Cas system wherein at least one DNA cleavage ability of Cas effector protein is inactivated (CRISPR-mutant Cas) is used as a nucleic acid sequence-recognizing module.

The nucleic acid sequence-recognizing module of the present invention using CRISPR-mutant Cas is provided as a complex of a CRISPR-RNA (crRNA) containing a sequence complementary to the target nucleotide sequence and, where necessary, trans-activating RNA (tracrRNA) necessary for recruiting mutant Cas effector protein (when tracrRNA is necessary, possibly provided as chimeric RNA with crRNA) and mutant Cas effector protein. An RNA molecule consisting of crRNA alone or a chimeric RNA of crRNA and tracrRNA that constitutes a nucleic acid sequence-recognizing module in combination with a mutant Cas effector protein is collectively referred to as "guide RNA". When a nucleic acid aptamer is used as a DNA modifying enzyme-binding module, the nucleic acid aptamer is desirably bonded to the guide RNA. A nucleic acid in which a guide RNA and a nucleic acid aptamer are bonded can be produced by a known method (e.g., Mali et al., (2013), Nat Biotechnol, 31(9), 833-838).

While the Cas effector protein to be used in the present invention is not particularly limited as long as it an effector protein belonging to the class 2 CRISPR system capable of forming a complex with guide RNA and recognizing and binding to the target nucleotide sequence in the object gene and a protospacer adjacent motif (PAM) adjacent thereto, it is preferably Cas9 or Cpf1. Examples of Cas9 include, but are not limited to, Cas9 (SpCas9) derived from *Streptococcus pyogenes*; PAM sequence (5'→3' direction; hereinafter the same) NGG (N is A, G, T or C, hereinafter the same)), Cas9 (StCas9; PAM sequence NNAGAAW) derived from *Streptococcus thermophilus*, Cas9 (MmCas9; PAM sequence NNNNGATT) derived from *Neisseria meningitidis* and the like. Preferred is SpCas9 with less restriction by PAM (substantially 2 bases, and can target theoretically any site on the genome). Examples of the Cpf1 include, but are not limited to, Cpf1 derived from *Francisella novicida* (FnCpf1; PAM sequence TTN), Cpf1 derived from *Acidaminococcus* sp. (AsCpf1; PAM sequence TTTN), Cpf1 derived from Lachnospiraceae bacterium (LbCpf1; PAM sequence TTTN) and the like. As a mutant Cas effector protein (hereinafter sometimes to be abbreviated as "mutation Cas") to be used in the present invention, any of Cas effector protein wherein the cleavage ability of the both strands of the double-stranded DNA is inactivated and one having nickase activity wherein at least one cleavage ability of one strand alone is inactivated can be used. For example, in the case of SpCas9, a D10A mutant in which the 10th Asp residue is converted to an Ala residue and lacking cleavage ability of a strand opposite to the strand forming a complementary strand with a guide RNA (thus having nickase activity for a strand forming complementary strand with guide RNA), or H840A mutant in which the 840th His residue is converted to an Ala residue and lacking cleavage ability of a strand forming a complementary strand to guide RNA (thus having nickase activity for a strand forming complementary strand with guide RNA, or a double mutant thereof (dCas9) can be used. In the case of FnCpf1, a variant in which the 917th Asp residue is converted to Ala residue (D917A) or the 1006th Glu residue is converted to Ala residue (E1006A), and lacking cleavage ability of both strands can be used. As long as at least one of the strands of double stranded DNA lacks cleavage ability, other mutant Cas can also be used similarly.

The DNA modifying enzyme-binding module is provided as a complex with mutant Cas by a method similar to the coupling scheme with the above-mentioned zinc finger and the like. Alternatively, a DNA modifying enzyme-binding module and mutant Cas can also be bound by utilizing RNA aptamers MS2F6, PP7 and the like and RNA scaffold by binding proteins thereto. The targeting sequence in the guide RNA forms a complementary strand with the target nucleotide sequence, mutant Cas is recruited by the tracrRNA attached and mutant Cas recognizes PAM. One or both DNAs cannot be cleaved and, due to the action of the DNA modifying enzyme-binding module linked to the mutant Cas, base conversion occurs in the targeted site (appropriately adjusted within several hundred bases including whole or partial target nucleotide sequence) and a mismatch occurs in the double stranded DNA. When the mismatch is not correctly repaired, and when repaired such that a base of the opposite strand forms a pair with a base of the converted strand, or when other nucleotide is further converted or when one to several dozen bases are deleted or inserted during repair, various mutations are introduced.

When CRISPR-mutant Cas is used as a nucleic acid sequence-recognizing module, similar to when zinc finger and the like are used as a nucleic acid sequence-recognizing module, a nucleic acid sequence-recognizing module and a DNA modifying enzyme-binding module are desirably introduced, in the form of a nucleic acid (preferably DNA) encoding same, into a cell having a DNA of interest.

A DNA encoding Cas effector protein (e.g., Cas9, Cpf1) can be cloned by a method similar to the above-mentioned method for a DNA encoding a DNA modifying enzyme-binding module, from a cell producing the protein. A mutant Cas can be obtained by introducing a mutation to convert an amino acid residue of the part important for the DNA cleavage activity (e.g., 10th Asp residue and 840th His residue for SpCas9, 917th Asp residue, 1006th Glu residue and 1255th Asp residue for FnCpf1 and the like, though not limited thereto) to other amino acid, into a DNA encoding cloned Cas, by a site specific mutation induction method known per se. In addition, by constructing full-length DNA by chemical synthesis or in combination with PCR method or Gibson Assembly method, codons to be used can also be designed over the full-length CDS according to the host into which the DNA is introduced. For example, as SpCas9 DNA introduced with such mutation and using a codon suitable for expression in human cells, a DNA having the nucleotide sequence shown in SEQ ID NO: 4 can be mentioned.

The obtained a DNA encoding a mutant Cas and/or a DNA encoding a DNA modifying enzyme-binding module can be inserted into the downstream of a promoter of an expression vector similar to the one mentioned above, according to the host cell. As mentioned above, the expression vector can contain, when desired, selection markers such as terminator, translation enhancer, 3' regulatory region, polyA addition signal, drug resistance gene and the like, and the like.

On the other hand, a DNA encoding guide RNA can be obtained by designing an oligoDNA sequence linking a coding sequence of crRNA sequence containing a nucleotide sequence complementary to the target nucleotide sequence (to be also referred to as "targeting sequence" in the present specification) (e.g., when FnCpf1 is recruited as Cas effector protein, crRNA containing SEQ ID NO: 10; AAUUUCUA-CUGUUGUAGAU at the 5'-side of the targeting sequence can be used, and underlined sequences form base pairs to take a stem-loop m structure), or a crRNA coding sequence and, as necessary, a known tracrRNA coding sequence (e.g., as tracrRNA coding sequence when Cas is recruited as Cas9 effector protein, gttttagagctagaaatagcaagt-taaaataaggctagtccgttatcaacttgaaaaagtggc accgagtcggtgc; SEQ ID NO: 11) and chemically synthesizing using a DNA/RNA synthesizer. When the target DNA is double stranded, crRNA sequence includes a nucleotide sequence complementary to a "targeted strand" of the target nucleotide sequence.

The "targeted strand" here means a strand forming a hybrid with crRNA of the target nucleotide sequence, and an opposite strand thereof that becomes single-stranded by hybridization to the targeted strand and crRNA is referred to as a "non-targeted strand". Since the DNA modification reaction is generally assumed to frequently occur on a single stranded non-targeted strand, when the target nucleotide sequence is to be expressed by one of the strands (e.g., when PAM sequence is indicated, when positional relationship of target nucleotide sequence and PAM is shown etc.), it is represented by a sequence of the non-targeted strand.

While the length of the targeting sequence is not particularly limited as long as it can specifically bind to a target nucleotide sequence, for example, it is 15-30 nucleotides, preferably 18-25 nucleotides. The selection of the target nucleotide sequence is restricted by the presence of an adjacent PAM on the 3'-side (in the case of Cas9) or 5'-side (in the case of Cpf1) of the sequence. According to the finding in yeast and the like, in a system in which CRISPR-mutated Cas and cytidine deaminase are combined, C at a position within 7 nucleotides from the 5'-end thereof toward 3' direction thereof is easily substituted irrespective of the length of the target nucleotide sequence. Therefore, by appropriately determining the length of the target nucleotide sequence (targeting sequence as a complementary strand thereof), the site of a base into which a mutation can be introduced may be shifted. As a result, restriction by PAM (NGG in SpCas9) may be removed at least partially, and the degree of freedom of mutation introduction is expected to be higher.

When Cas9 is used as a Cas effector protein, a targeting sequence can be designed, for example, using a guide RNA design website open to public (CRISPR Design Tool, CRISPRdirect etc.) by listing up 20 mer sequences having PAM (e.g., NGG in the case of SpCas9) adjacent to the 3'-side from the CDS sequences of the object gene, and selecting a sequence that causes an amino acid change in the protein encoded by the target gene when C within 7 nucleotides from the 5' end thereof toward 3' direction is converted to T. Furthermore, a sequence having C that similarly causes, when the length of the targeting sequence is changed, for example, within the range of 18-25 nucleotides, an amino acid change by base conversion to T within 7 nucleotides from the 5' end thereof toward 3' direction is selected. A candidate sequence having a small number of off-target sites in the genome of the host can be used as a targeting sequence. When the guide RNA design software to be used does not have a function to search off-target sites of the genome of the host, for example, off-target sites can be searched by applying a Blast search to the genome of the host, for example, 8-12 nucleotides on the 3'-side of the candidate sequence (seed sequence with high discrimination ability of target nucleotide sequence).

A DNA encoding guide RNA (e.g., crRNA or crRNA-tracrRNA chimera) can be obtained by designing an oligoDNA sequence linking a sequence complementary to the target strand of the target nucleotide sequence and a known tracrRNA sequence (when Cas9 is recruited) or a direct repeat sequence of crRNA (when Cpf1 is recruited) and chemically synthesizing using a DNA/RNA synthesizer. While a DNA encoding guide RNA can also be inserted into an expression vector similar to the one mentioned above, as the promoter, pol III system promoter (e.g., SNR6, SNR52, SCR1, RPR1, U3, U6, H1 promoter etc.) and terminator (e.g., $T_6$ sequence; tttttt etc.) are preferably used.

DNA encoding mutant Cas, DNA encoding DNA modifying enzyme-binding module, a DNA encoding guide RNA can be introduced into a host cell by a method similar to the above, according to the host.

In genome editing using a complex of deaminase and a nucleic acid sequence-recognizing module (hereinafter sometimes to be referred to as "Target AID") (patent document 5), the present inventors compared the effects of two kinds of mutant Cas having nickase activity of cleaving different strand and reported that mutated sites gathered near the center of the target nucleotide sequence in one of them and various mutations were randomly introduced into region of several hundred bases from the target nucleotide sequence in the other, and thus, similar effects can also be expected in the present invention. Therefore, by selecting a strand to be cleaved by the nickase, a mutation can be introduced into a particular nucleotide or nucleotide region at a pinpoint, or various mutations can be randomly introduced into a comparatively wide range, which can be property adopted according to the object. For example, when the former technique is applied to gene disease iPS cell, an agent for cell transplantation therapy with a reduced risk of rejection by repairing the mutation of the pathogenic gene in iPS cells prepared from the patient's own cells and then differentiating them into the desired somatic cells can be produced.

In Target AID, the present inventors also confirmed using a budding yeast that when sequence-recognizing modules are produced corresponding to the adjacent multiple target nucleotide sequences, and simultaneously used, the mutation introduction efficiency drastically increases than using a single nucleotide sequence as a target, and similar effects can also be expected in the present invention. When the target DNA is a double stranded DNA, it can occur both when the target nucleotide sequences are in the same direction (i.e., targeted strands are on the same strand), and when they are opposed (i.e., both strands of double stranded DNA are targeted strands).

In addition, modification of multiple DNA regions at completely different positions as targets can also be performed. Therefore, in one preferable embodiment of the present invention, two or more kinds of nucleic acid sequence-recognizing modules that specifically bind to different target nucleotide sequences (which, when target DNA is cell-endogenous DNA, may be present in one object gene, or two or more different object genes) can be used. In this case, each one of these nucleic acid sequence-recognizing modules and a DNA modifying enzyme-binding module form a complex. Here, a common DNA modifying enzyme-binding module can be used. For example, when CRISPR-Cas system is used as a nucleic acid sequence-recognizing module, a common complex of Cas effector protein and DNA modifying enzyme-binding module (including fusion protein) is used, and two or more guide RNAs containing two or more crRNAs that respectively form a complementary strand with a different target nucleotide sequence are produced and can be used as guide RNA. On the other hand, when zinc finger motif, TAL effector and the like are used as nucleic acid sequence-recognizing modules, for example, a DNA modifying enzyme-binding module can be fused with a nucleic acid sequence-recognizing module that specifically binds to a different target nucleotide.

To express the complex of the present invention in a host cell, as mentioned above, an expression vector containing a DNA encoding a nucleic acid sequence-recognizing module and a DNA encoding a DNA modifying enzyme-binding module (both DNAs may be on separate vectors or a single vector) or RNAs encoding respective modules are introduced into a host cell. For efficient introduction of mutation, it is desirable to maintain an expression of the complex of the present invention at a given level or above for not less than a given period. From such aspect, it is ensuring to introduce an expression vector (e.g., plasmid etc.) autonomously replicatable in a host cell. However, since the plasmid etc. are foreign DNAs, they are preferably removed rapidly after successful introduction of mutation. Therefore, though subject to change depending on the kind of host cell and the like, for example, the introduced plasmid is desirably removed from the host cell after a lapse of 6 hr-2 days from the introduction of an expression vector by using various plasmid removal methods well known in the art.

Examples of the means for removing foreign DNA incorporated into the host genomic DNA include a method using a Cre-loxP system, a method using transposon and the like.

Alternatively, as long as expression of the complex of the present invention, which is sufficient for the introduction of mutation, is obtained, it is preferable to introduce mutation into the object DNA by transient expression by using an expression vector or RNA without autonomous replicatability in a host cell (e.g., vector etc. lacking replication origin that functions in host cell and/or gene encoding protein necessary for replication).

Alternatively, editing of the host DNA can be realized efficiently while avoiding the risk of off-target action by causing a DNA modification reaction in a desired stage, and transiently expressing the complex of the present invention in a host cell for a period necessary for fixing the alteration of the targeted site. While a period necessary for the DNA modification reaction and fixing the alteration of the targeted site can be appropriately determined similarly to the above-mentioned period for stimulating the cells with a DNA modifying enzyme inducer. The expression induction period of the a nucleic acid encoding the complex of the present invention may be extended beyond the above-mentioned period as long as the host cell is free of unpreferable side effects.

As a means for transiently expressing the complex of the present invention at a desired stage for a desired period, a method including producing a construct (expression vector) containing a DNA encoding the complex [i.e., DNA encoding nucleic acid sequence-recognizing module (DNA encoding a guide RNA and DNA encoding a mutant Cas in the CRISPR-Cas system), and DNA encoding DNA modifying enzyme-binding module (in the CRISPR-Cas system, a DNA encoding a DNA modifying enzyme-binding module can be linked to a DNA encoding a mutant Cas or a DNA encoding a guide RNA, respectively, depending on whether the module is a protein or RNA)] in a form permitting control of the expression period of the complex and introducing same into the host cell can be mentioned. The "form capable of controlling the expression period" is specifically, for example, a DNA encoding the complex of the present invention placed under regulation of an inducible regulatory region. While the "inducible regulatory region" is not particularly limited, it is, for example, an operon of a temperature sensitive (ts) mutation repressor and an operator regulated thereby in microbial cells such as bacterium (e.g., *Escherichia coli*), yeast and the like. Examples of the ts mutation repressor include, but are not limited to, ts mutation of λphage-derived cI repressor. In the case of λphage cI repressor (ts), it is bound to an operator to suppress expression of gene in the downstream at not more than 30° C. (e.g., 28° C.). At a high temperature of not less than 37° C. (e.g., 42° C.), it is dissociated from the operator to allow for induction of gene expression. Therefore, the period when the expression of the target gene is suppressed can be minimized by culturing a host cell introduced with a DNA encoding the complex of the present invention generally at not more than 30° C., raising the temperature to not less than 37° C. at an appropriate stage, performing culture for a given period to cause expression of the complex of the present invention and a DNA modification reaction by a cell-endogenous DNA modifying enzyme recruited by the complex and, after introduction of mutation into the target gene, rapidly lowering the temperature to not more than 30° C. Thus, even when an essential gene for the host cell is targeted, it can be efficiently edited while suppressing the side effects.

When temperature sensitive mutation is utilized, for example, a temperature sensitive mutant of a protein necessary for autonomous replication of a vector is mounted on a vector containing a DNA encoding the complex of the present invention. As a result, autonomous replication cannot occur rapidly after expression of the complex, and the vector naturally falls off along with the cell division. Examples of such temperature sensitive mutant protein include, but are not limited to, a temperature sensitive variant of Rep101 ori necessary for replication of pSC101 ori. At not more than 30° C. (e.g., 28° C.), Rep101 ori (ts) acts on pSC101 ori to enable autonomous replication of plasmid. At not less than 37° C. (e.g., 42° C.), pSC101 ori loses its function and plasmid cannot replicate autonomously. Therefore, a combined use with cI repressor (ts) of the above-mentioned λphage simultaneously enables transient expression of the complex of the present invention, and removal of the plasmid.

When a higher eukaryotic cell such as animal cell, insect cell, plant cell or the like is a host cell, a DNA encoding the complex of the present invention is introduced into the host cell under the control of an induction promoter (e.g., metallothionein promoter (induced by heavy metal ion), heat shock protein promoter (induced by heat shock), Tet-ON/Tet-OFF system promoter (induced by addition or removal of tetracycline or a derivative thereof), steroid-responsive promoter (induced by steroid hormone or a derivative thereof) etc.), an induction substance is added to (or removed from) the medium at an appropriate time to induce expression of the complex, the cells are cultured for a certain period to cause a DNA modification reaction by cell-endogenous DNA modifying enzyme recruited to the complex, and the aforementioned induction substance is removed from the medium after the mutation is introduced into the target gene, whereby a transient expression of the complex of the present invention can be realized.

An induction promoter can be utilized in prokaryotic cells such as *Escherichia coli* and the like. Examples of such induction promoter include, but are not limited to, lac promoter (induced by IPTG), cspA promoter (induced by cold shock), araBAD promoter (induced by arabinose) and the like.

Alternatively, the above-mentioned induction promoter can also be utilized as a vector removal mechanism when a higher eukaryotic cell such as animal cell, insect cell, plant cell or the like is a host cell. That is, a vector is loaded with a replication origin that functions in the host cell and a nucleic acid encoding a protein necessary for the replication (e.g., SV40 ori and large T antigen, oriP and EBNA-1 and the like for animal cells) and the expression of the nucleic acid encoding the protein is controlled by the above-mentioned induction promoter. The vector is autonomously replicatable in the presence of the induction substance, but cannot replicate autonomously when the induction substance is removed, and the vector falls off spontaneously along with cell division (Tet-OFF vector cannot replicate autonomously when tetracycline or doxycycline is added).

According to the studies conducted by the present inventors, once the expression and activity of a cell-endogenous DNA modifying enzyme is sufficiently increased using a DNA modifying enzyme inducer, the target DNA can be modified in some cases without using a DNA modifying enzyme-binding module but using only a nucleic acid sequence-recognizing module. While not wishing to be bound by any theory, a possible mechanism is that a DNA modifying enzyme present in a sufficient amount more frequently contacts the distortion of double helix structure in the target site which is caused by binding of the nucleic acid sequence-recognizing module, acts on the target site and alters the target DNA.

Therefore, in another embodiment of the present invention, a method for altering a targeted site of a DNA in a cell, comprising a step of stimulating the cell with a factor inducing a DNA modifying enzyme endogenous to the cell, and bringing a nucleic acid sequence-recognizing module specifically binding to a target nucleotide sequence in a given double stranded DNA into contact with the double stranded DNA to convert one or more nucleotides in the targeted site to other one or more nucleotides or delete one or more nucleotides, or insert one or more nucleotides into said targeted site is provided.

The present invention is explained in the following by referring to Examples, which are not to be construed as limitative.

Examples

Figure 2:
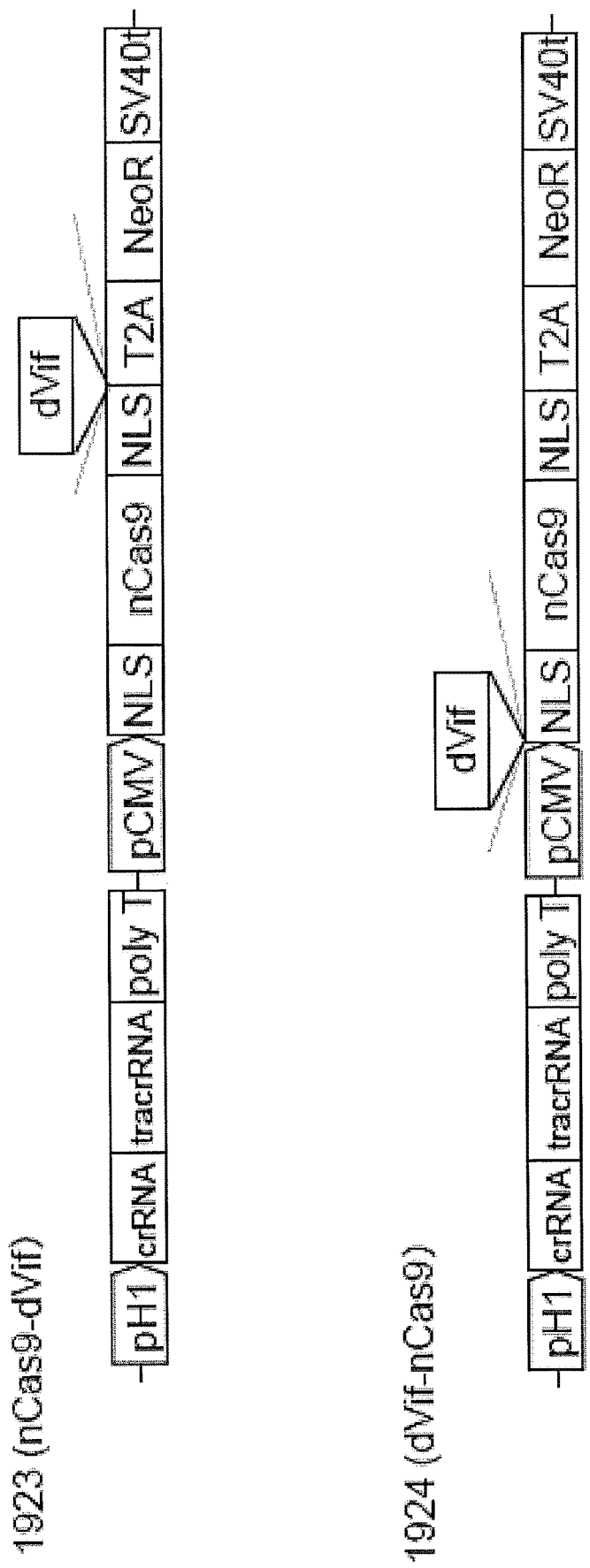
FIG. 2 is a schematic showing of the plasmid for DNA editing used in the Examples.

1. Vector Construction
1-1. Cas9, nCas9, nCas9-dVif, dVif-nCas9 or nCas9-PmCDA1 Expression Vector The outline of the plasmid vector for DNA editing used in the Examples is shown in FIG. 1. Using pNeo vector as a base, a plasmid vector for gene transgene was constructed by transfection into human fetal kidney-derived cells (HEK293T cells). As the plasmid vector, 1907c (Cas9), 1907n (nCas9-PmCDA1), 1907n-cugi (nCas9-PmCDA1-UGI), 1921 (nCas9), 1923 (nCas9-dVif), 1924 (dVif-nCas9) targeting Exon6 of hypoxanthine-guanine phosphoribosyltransferase (HPRT) gene were used and pNeo was used as a control. 1907c (Cas9), 1907n (nCas9-PmCDA1), 1907n-cugi (nCas9-PmCDA1-UGI) and 1921 (nCas9) were constructed based on the vector used in non-patent document 3 and by changing the target sequence of guide RNA to the 24th-43rd sequence (aatgcagactttgctttcct: SEQ ID NO: 12) (site 3) from the start point of exon 6 of HPRT gene. As a DNA encoding nCas9 (D10A), a DNA consisting of the base sequence shown in SEQ ID NO: 4 was used. 1923 (nCas9-dVif) and 1924 (dVif-nCas9) were produced as follows. First, vector 1922 (SEQ ID NO: 13) was constructed by addition of a restriction enzyme site to and removal of unnecessary sequence from 1921 (nCas9). As for dVif fragment of HIV, reference was made to GenBank: AF200477.1 which is a Vif sequence on the database. In 28-576 bases of ORF of the aforementioned sequence, the 433rd-435th bases (CTA) were altered to GCT to synthesize an artificial gene introduced with L145A mutation (base sequence is shown in SEQ ID NO: 1, amino acid sequence is shown in SEQ ID NO: 2. A base sequence in which AvrII recognition site was added to 5'-side and NheI recognition site was added to 3'-side is shown in SEQ ID NO: 3), and the artificial gene was inserted in 1922 by cleavage of restriction enzyme and ligation to produce 1923 (nCas9-dVif) and 1924 (dVif-nCas9). FIG. 2 shows a schematic drawing of vectors 1923 (nCas9-dVif) and 1924 (dVif-nCas9) produced.

The aforementioned vectors were introduced into HEK293T cells and expressed in the cells to form a complex of crRNA-tracrRNA, and Cas9, nCas9, nCas9-dVif, dVif-nCas9 or nCas9-PmCDA1.

Figure 3:
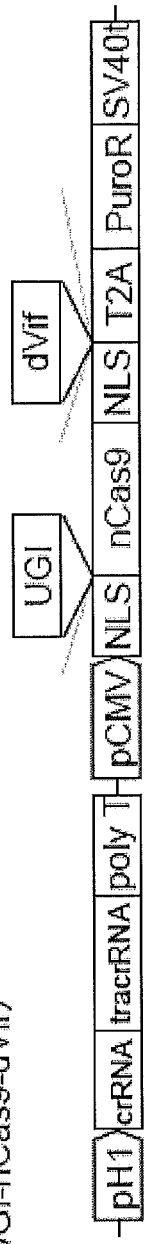
FIG. 3 is a schematic showing of the plasmid for DNA editing used in the Examples.
Figure 3:
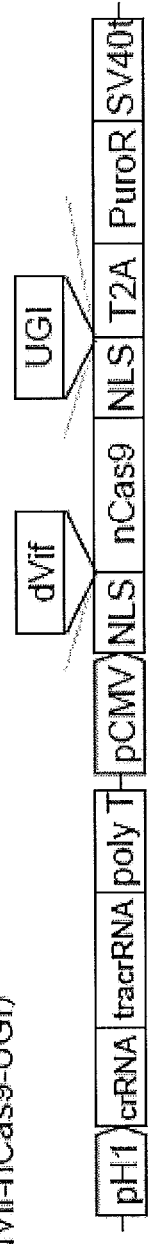
Figure 3:
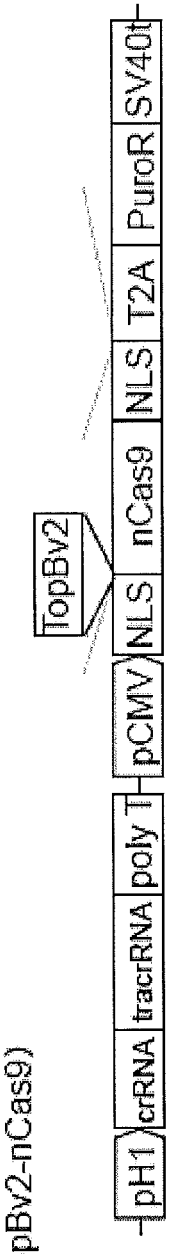
Figure 3:

1-2. UGI-nCas9-dVif, dVif-nCas9-UGI, TopBv2(TopoIIβ Isoform 2)-nCas9, nCas9-IQGAP2$_{466-547}$-ZNF335$_{745-893}$ or nCas9-PmCDA1-UGI Expression Vector Referring to the procedure of 1-1., vector 1923-2 (UGI-nCas9-dVif: SEQ ID NO: 28), vector 1924-2 (dVif-nCas9-UGI: SEQ ID NO: 29), vector 1931 (TopBv2$_{452-591}$-nCas9: SEQ ID NO: 30) and vector 1932 (nCas9-IQGAP2$_{466-547}$-ZNF335$_{745-893}$: SEQ ID NO: 31) were produced each of which targets a particular region of HPRT gene (target sequence (site 1): tcgagatgtgatgaaggaga; SEQ ID NO: 27). In addition, vector 1907 (nCas9-PmCDA1-UGI: SEQ ID NO: 32) was produced for comparative testing. The base sequences encoding the fragments of TopBv2, IQGAP2 and ZNF335 were designed by reference to refseq No: NM_001068, NM_006633 and NM_022095, each of which is a sequence on the database. FIG. 3 shows a schematic drawing of vectors 1923-2, 1924-2, 1931 and 1932 produced. The base sequence encoding UGI and the amino acid sequence of UGI are respectively shown in SEQ ID NO: 19 and 20, the base sequence encoding TopBv2$_{452-591}$ and the amino acid sequence of TopBv2$_{452-591}$ are respectively shown in SEQ ID NO: 21 and 22, the base sequence encoding IQGAP2$_{466-547}$ and the amino acid sequence of IQGAP2$_{466-547}$ are respectively shown in SEQ ID NO: 23 and 24, and the base sequence encoding ZNF335$_{745-893}$ and the amino acid sequence of ZNF335$_{745-893}$ are respectively shown in SEQ ID NO: 25 and 26.

2. Cell Line, Culture, Transformation, Expression Induction
2-1. Introduction System of Vector of 1-1

The experiment using the vector of the above-mentioned 1-1 was performed by the following procedure. Human fetal kidney-derived cells (HEK293T cells) were used. The cells were cultured in a DME-glutamax medium (Thermo Fisher Scientific, USA) added with 100 µg/mL penicillin-streptomycin (Life Technologies, Carlsbad, CA, USA) and 10% fetal bovine serum (FBS) (Biosera, Nuaille, France) under 37° C., 5% CO$_2$ conditions. The cells were recovered using 5% trypsin.

HEK293T cells preserved in a deep freezer were dissolved in a water bath at 37° C. and seeded in a 75 T-flask at 5×10$^6$ cells. After culturing for 1-3 days, the cells were recovered and seeded in each well of a 24 well plate at 0.5×10$^5$ cells/well. After culturing for 1-3 days, about 1 µg of each of the above-mentioned plasmid DNAs was transfected into 60-80% confluent cells in each well by using 3 µl of Lipofectamine 2000 (Life Technologies, Carlsbad, USA). After 5 hours of transfection, the medium was replaced with one containing G418 (0.125 mg/mL) (InvivoGen, USA) and interferon α (IFNα) (2000 IU) (Takara Bio) or interferon γ (2000 IU) (PeproTech, Inc.). As a control, a medium containing G418 alone was used.

2-2. Introduction System of Vector of 1-2

The experiment using the vector of the above-mentioned 1-2 was performed by the following procedure. The cells (HEK293 or HepG2) were seeded in each well of a 24 well plate at 1×10$^5$ cells/well and cultured overnight. Then, transfection (DNA 1 µg/well, FugeneHD 1.5 µl/well) was performed using FugeneHD (Promega) and the medium was replaced 16 hr later. In the case of HEK293, OPTI-MEM was replaced with DMEM+10% FBS+P/S (penicillin-streptomycin)+Puromycin (1 µg/ml)+/−IFNα (10000 U/ml). In the case of HepG2, OPTI-MEM was replaced with DMEM+ 10% FBS+P/S+1% NEAR (non-essential amino acid)+Puromycin (1 µg/ml)+/−IFNα (10000 U/ml). Selection by puromycin was continued for 6 days. In this case, the medium was replaced every 48 hr.

3. Sequence Analysis
3-1. Introduction System of Vector of 1-1

Genomic DNA was extracted by the following procedure from the cells recovered in the above-mentioned 2-1 and the sequence was analyzed. For sequence analysis, each cell was recovered 3 days after culture and genomic DNA was extracted. Using the extracted genomic DNA as a template and forward primer (5'-ATTCCAGAATATCTCCATGTA-GATTTTGGT-3': SEQ ID NO: 14) and reverse primer (5'-AATTCCAGGAGGTCCAGATCTTCAGGGCCC-3': SEQ ID NO: 15) targeting Exon 6 of HPRT gene, the target region was amplified. Using the amplified DNA fragment as a template and forward primer (5'-TCTTTCCCTA-CACGACGCTCTTCCGATCTATTCCAGAATATCTC-CATGTAGATTTTGGT-3': SEQ ID NO: 16) and reverse primer (5'-GTGACTGGAGTTCA-GACGTGTGCTCTTCCGATCTT-TAGGCAAGGAAGTGACTGTAATTATGAG C-3': SEQ ID NO: 17), an about 300 bp amplification fragment added with an adapter for NGS analysis was obtained. An index sequence was added to each sample and deep sequencing with paired-end was performed using MiSeq Reagent Kit v3 and MiSeq sequencing system (Illumina). CLC Genomics Workbench 7.0 (Filgen) was used for the analysis. The results are shown in Table 1. In the Table, indel shows insertion deletion and number shows a nucleotide substitution rate (%). When cells expressing a complex of nCas9 and dVif were cultured in the presence of interferon, insertion deletions and/or base substitution occurred, and the base substitution was mostly substitution from cytosine to thymine. The ratio of insertion deletion and base substitution was of the same level as that in the conventional method (Target-AID) using exogenous deaminase. Many substitutions of bases are observed in the 19th T and 20th C of the nucleic acid bases in the Table. These mutations are considered to be sequence errors because substitution is highly frequently seen also in pNeo.

TABLE 1

| | | HPRT site3 | Indel (%) | A | C | A | A | T | G | C | A | G | A | C | T | T |
|---|---|---|---|---|---|---|---|---|---|---|---|---|---|---|---|---|
| control | | Neo | 0 | | | | | | | | | | | | | |
| | | Cas9 | 2.16 | | | | | A 0.12 | T 0.12 | C 0.16 G 0.12 T 0.2 | C 0.2 T 0.81 | C 0.12 T 0.16 | A 0.15 | G 0.31 | A 0.73 C 0.49 G 0.49 |
| | | nCas9 | 0 | | | | | | | | | | | | | |
| IFN | | nCas9 with αIFN | 0 | | | | | | | | | | | | | |
| | | nCas9 with γIFN | 0 | | | | | | | | | | | | | |
| dVif | | nCas9-dVif | 0 | | | | | | | | | | | | | |
| IFN + dVif | | nCas9-dVif αIFN | 0 | | | | | A 0.15 T 0.15 | T 0.37 | | | | | | |
| | | nCas9-dVif γIFN | 0.23 | | | | | | T 0.22 | | | | | | | |
| | | dVif-nCas9 | 0 | | | | | | | | | | | | | |
| | | dVif-nCas9 αIFN | 0.11 | | | | | | T 0.33 | | | | | | | |
| | | dVif-nCas9 γIFN | 0 | | | | | | | | | | | | | |
| Target-AID | | nCas9-PmCDA1 | 0.11 | | | | | | T 0.36 | | | | | | | |

| | | HPRT site3 | Indel (%) | T | G | C | T | T | T | C | C | T | G | G | T |
|---|---|---|---|---|---|---|---|---|---|---|---|---|---|---|---|
| | control | Neo | 0 | | | | | | | A 0.66 C 0.33 G 0.8 | A 1.73 | | | | |
| | | Cas9 | 2.16 | A 0.12 | A 0.16 | | | | | A 0.64 C 0.28 G 0.65 | A 1.52 G 0.43 T 0.35 | | T 0.12 | T 0.1 | |
| | | nCas9 | 0 | | | | | | | A 0.74 C 0.32 G 0.69 | A 1.66 | | | | |
| IFN | | nCas9 with αIFN | 0 | | | | | | | A 0.71 C 0.28 G 0.76 | A 1.77 | | | | |
| | | nCas9 with γIFN | 0 | | | | | | | A 0.71 G 0.76 | A 1.71 | | | | |
| dVif | | nCas9-dVif | 0 | | | | | | | A 0.71 C 0.37 G 0.74 | A 1.64 | | | | |
| IFN + dVif | | nCas9-dVif αIFN | 0 | | | | | | | A 0.74 C 0.27 G 0.73 | A 1.77 | | | | |
| | | nCas9-dVif γIFN | 0.23 | | | | | | | A 0.63 C 0.34 G 0.74 | A 1.61 G 0.36 | | | | |
| | | dVif-nCas9 | 0 | | | | | | | A 0.65 G 0.67 | A1.72 | | | | |
| | | dVif-nCas9 αIFN | 0.11 | | | | | | | A 0.64 C 0.29 G 0.68 | A 1.7 T 0.38 | | | | |
| | | dVif-nCas9 γIFN | 0 | | | | | | | A 0.69 C 0.31 G 0.74 | A 1.72 G 0.42 | | | | |
| | Target-AID | nCas9-PmCDA1 | 0.11 | | | | | | | A 0.71 C 0.31 G 0.72 | A 1.67 G 0.41 | | | | |

3-2. Introduction System of Vector of 1-2

Genomic DNA was extracted from the cells collected in the above-mentioned 2.2 and the sequence was analyzed. HEK293 cells were collected on day 6, HepG2 cells were collected after recovery culture for 48 hr, and genomic DNA was extracted using NucleoSpin Tissue XS (Takara Bio Inc.). 1st PCR (DNA polymerase: KOD FX NEO (Toyobo), primer set: forward primer (5'-TTTGGTACTTGTTCAGCTTTATTCAAGTGG-3': SEQ ID NO: 33); reverse primer (5'-ACAATAGCTCTTCAGTCTGATAAAATCTAC-3': SEQ ID NO: 34)) was performed, the band was confirmed by electrophoresis, and the PCR product was purified using Exo/Sap (Thermo Fisher Scientific) to give a 1100 bp amplification fragment. Then, using the PCR product after purification as a template, 2nd PCR (DNA polymerase: KOD FX NEO, primer set: forward primer (5'-TCTTTCCC-TACACGACGCTCTTCCGATCT TAGGACT-GAACGTCTTGCTC-3': SEQ ID NO: 35); reverse primer (5'-GTGACTGGAGTTCAGACGTGTGCTCTTCC-GATCT CAGTCATAGGAATGGATCTATCAC-3': SEQ ID NO: 36)) was performed, the band was confirmed by electrophoresis, and the PCR product was purified using Exo/Sap to give a 220 bp amplification fragment. Furthermore, using the PCR product after purification as a template, 3rd PCR (Q5 DNA polymerase (New England Biolabs), primer set: SEQ ID NO: 14 and 15) was performed, and the PCR product was purified using AMPure XP (Beckman Coulter) to give an about 150 bp amplification fragment added with an adapter for NGS analysis. The band of the samples after purification using AMPure XP was confirmed by Multina (SHIMADZU Corporation). The samples were pooled by referring to the bands (concentrations) obtained by Multina and the concentration of the samples was measured using Qubit (Thermo Fisher Scientific). The samples were diluted to 10 nM and confirmed by Qubit to be at 10 nM. 10 nM samples were diluted to 1 nM and 1 nM samples were altered. Thereafter, the samples were diluted to 1.5 μM. 4 nM PhiX (Illumina) was altered and diluted to 1.5 μM. 500 μl of the sample (1.5 μM) and 100 μl of PhiX (1.5 μM) were mixed and applied to a cartridge. Miniseq (Illumina) was started to perform sequencing. The results are shown in Table 2. In the Table, indel shows insertion deletion (indel was not detected in Table 2) and number shows substitution rate (%) of nucleotide. When HEK293 cells made to express a complex of UGI, nCas9 and dVif were cultured in the presence of interferon, base substitution from cytosine to thymine occurred. Similarly, when cells made to express a complex of nCas9 and TopBv2 or IQGAP2 and ZNF335 were cultured in the presence of interferon, base substitution from cytosine to thymine occurred. In addition, when HepG2 cells made to express a complex of UGI, nCas9 and dVif were cultured in the presence of interferon, base substitution from cytosine to thymine occurred. When HepG2 cells were used, the rate of base substitution was of the same level as the conventional method using exogenous deaminase (Target-AID).

TABLE 2

Hek293 cell HPRT site1
1923-2: UGI-nCas9-Vif

|    |       |      | 21 | 20 | 19 | 18 | 17 | 16 | 15 | 14 | 13 | 12 | 11 | 10 | 9 | 8 | 7 | 6 | 5 | 4 | 3 | 2 | 1 | PAM |
|----|-------|------|----|----|----|----|----|----|----|----|----|----|----|----|---|---|---|---|---|---|---|---|---|-----|
| 24 |       |      |    | C  | T  | C  | G  | A  | G  | A  | T  | G  | T  | G  | A | T | G | A | A | G | G | A | G | A | TGG |
| 1923-2 | C > T | 0.99 |  |    |    |    |    |    |    |    |    |    |    |    |   |   |   |   |   |   |   |   |   |     |
| IFNα | C > G |     |    |    |    |    |    |    |    |    |    |    |    |    |   |   |   |   |   |   |   |   |   |     |
|    | Indel |     |    |    |    |    |    |    |    |    |    |    |    |    |   |   |   |   |   |   |   |   |   |     |

1924-2: Vif-nCas9-UGI

|    |       |      | 21 | 20 | 19 | 18 | 17 | 16 | 15 | 14 | 13 | 12 | 11 | 10 | 9 | 8 | 7 | 6 | 5 | 4 | 3 | 2 | 1 | PAM |
|----|-------|------|----|----|----|----|----|----|----|----|----|----|----|----|---|---|---|---|---|---|---|---|---|-----|
| 18 |       |      |    | C  | T  | C  | G  | A  | G  | A  | T  | G  | T  | G  | A | T | G | A | A | G | G | A | G | A | TGG |
| 1924-2 | C > T | 0.76 |  |    |    |    |    |    |    |    |    |    |    |    |   |   |   |   |   |   |   |   |   |     |
| IFNα | C > G |     |    |    |    |    |    |    |    |    |    |    |    |    |   |   |   |   |   |   |   |   |   |     |
|    | Indel |     |    |    |    |    |    |    |    |    |    |    |    |    |   |   |   |   |   |   |   |   |   |     |

1931: TopBv2-nCas9

|    |       |      | 21 | 20 | 19 | 18 | 17 | 16 | 15 | 14 | 13 | 12 | 11 | 10 | 9 | 8 | 7 | 6 | 5 | 4 | 3 | 2 | 1 | PAM |
|----|-------|------|----|----|----|----|----|----|----|----|----|----|----|----|---|---|---|---|---|---|---|---|---|-----|
| 31 |       |      |    | C  | T  | C  | G  | A  | G  | A  | T  | G  | T  | G  | A | T | G | A | A | G | G | A | G | A | TGG |
| 1931 | C > T | 0.8 |   |    |    |    |    |    |    |    |    |    |    |    |   |   |   |   |   |   |   |   |   |     |
| IFNα | C > G |     |    |    |    |    |    |    |    |    |    |    |    |    |   |   |   |   |   |   |   |   |   |     |
|    | Indel |     |    |    |    |    |    |    |    |    |    |    |    |    |   |   |   |   |   |   |   |   |   |     |

1932: nCas9-ZF

|    |       |      | 21 | 20 | 19 | 18 | 17 | 16 | 15 | 14 | 13 | 12 | 11 | 10 | 9 | 8 | 7 | 6 | 5 | 4 | 3 | 2 | 1 | PAM |
|----|-------|------|----|----|----|----|----|----|----|----|----|----|----|----|---|---|---|---|---|---|---|---|---|-----|
| 27 |       |      |    | C  | T  | C  | G  | A  | G  | A  | T  | G  | T  | G  | A | T | G | A | A | G | G | A | G | A | TGG |
| 1932 | C > T | 0.71 |  |    |    |    |    |    |    |    |    |    |    |    |   |   |   |   |   |   |   |   |   |     |
| IFNα | C > G |     |    |    |    |    |    |    |    |    |    |    |    |    |   |   |   |   |   |   |   |   |   |     |
|    | Indel |     |    |    |    |    |    |    |    |    |    |    |    |    |   |   |   |   |   |   |   |   |   |     |

HepG2 cell HPRT site1
1924-2: Vif-nCas9-UGI

|    |       |      | 21 | 20 | 19 | 18 | 17 | 16 | 15 | 14 | 13 | 12 | 11 | 10 | 9 | 8 | 7 | 6 | 5 | 4 | 3 | 2 | 1 | PAM |
|----|-------|------|----|----|----|----|----|----|----|----|----|----|----|----|---|---|---|---|---|---|---|---|---|-----|
| 40 |       |      |    | C  | T  | C  | G  | A  | G  | A  | T  | G  | T  | G  | A | T | G | A | A | G | G | A | G | A | TGG |
| 1924-2 | C > T | 2.22 |  |    |    |    |    |    |    |    |    |    |    |    |   |   |   |   |   |   |   |   |   |     |
| IFNα | C > G |     |    |    |    |    |    |    |    |    |    |    |    |    |   |   |   |   |   |   |   |   |   |     |
|    | Indel |     |    |    |    |    |    |    |    |    |    |    |    |    |   |   |   |   |   |   |   |   |   |     |

TABLE 2-continued

1907: nCas9-CDA-ugi (reference data)

| 37 | | 21 | 20 | 19 | 18 | 17 | 16 | 15 | 14 | 13 | 12 | 11 | 10 | 9 | 8 | 7 | 6 | 5 | 4 | 3 | 2 | 1 | PAM |
|---|---|---|---|---|---|---|---|---|---|---|---|---|---|---|---|---|---|---|---|---|---|---|---|
| | | C | T | C | G | A | G | A | T | G | T | G | A | T | G | A | A | G | G | A | G | A | TGG |
| 1907 | C > T | 2.14 | | 3.17 | | | | | | | | | | | | | | | | | | | |
| IFNα | C > G Indel | | | 0.5 | | | | | | | | | | | | | | | | | | | |

This application is based on a patent application No. 2017-056727 filed in Japan (filing date: Mar. 22, 2017), the contents of which are incorporated in full herein.

INDUSTRIAL APPLICABILITY

According to the present invention, DNA editing which is safe due to the non-use of an exogenous enzyme in an alteration reaction of DNA and improved in the delivery efficiency by miniaturization of a construct used for the DNA editing has become possible, and the present invention is extremely useful.

---

The invention claimed is:

1. A method for altering a DNA in a cell, comprising
stimulating the cell with a cytokine that activates or increases the expression or activity of an apolipoprotein B mRNA-editing enzyme catalytic (APOBEC) cytidine deaminase that is endogenous to the cell and that is natively present in the cell,
contacting a complex of a Cas9, a guide RNA, and an APOBEC cytidine deaminase binding module with the DNA of the cell, wherein at least one DNA cleavage ability of the Cas9 is inactivated, wherein the Cas9 and the APOBEC cytidine deaminase binding module are linked to each other in the complex, wherein said APOBEC cytidine deaminase binding module has the ability to bind to APOBEC cytidine deaminase, and wherein the APOBEC cytidine deaminase binding module is selected from the group consisting of Virion infectivity factor (Vif), Topoisomerase 2-beta (Topo11β), IQ motif-containing GTPase activating protein 2 (IQGAP2) and Zinc finger protein 335 (ZNF335), and fragments thereof that bind to APOBEC cytidine deaminase, and
binding the APOBEC cytidine deaminase to the APOBEC cytidine deaminase binding module of the complex and converting a nucleotide of the DNA to a different nucleotide, deleting a nucleotide of the DNA, or inserting a nucleotide into the DNA, thereby altering the DNA in the cell.

2. The method according to claim 1, wherein said DNA is altered without cleaving at least one strand of said DNA.

3. The method according to claim 1, wherein the complex of the Cas9, the guide RNA, and the APOBEC cytidine deaminase binding module further comprises a base excision repair inhibitor linked thereto.

4. The method according to claim 1, wherein said DNA and said complex are contacted by introducing nucleic acids encoding the Cas9, the guide RNA, and the APOBEC cytidine deaminase binding module into said cell and culturing the cell to cause expression of the Cas9, the guide RNA, and the APOBEC cytidine deaminase binding module in the cell.

5. The method according to claim 1, wherein the cell is stimulated with the cytokine by incubating the cell in the presence of the cytokine.

6. The method according to claim 1, wherein said cell is a vertebrate cell.

7. The method according to claim 6, wherein said vertebrate cell is a mammalian cell.

8. The method according to claim 1, wherein said DNA is a double stranded DNA.

* * * * *

UNITED STATES PATENT AND TRADEMARK OFFICE
CERTIFICATE OF CORRECTION

| | | |
|---|---|---|
| PATENT NO. | : 11,845,953 B2 | Page 1 of 1 |
| APPLICATION NO. | : 16/496311 | |
| DATED | : December 19, 2023 | |
| INVENTOR(S) | : Keiji Nishida et al. | |

It is certified that error appears in the above-identified patent and that said Letters Patent is hereby corrected as shown below:

In the Claims

At Claim 1, Column 125, Line 29: "Topoisomerase 2-beta (Topo11β)" should read "Topoisomerase 2-beta (TopoIIβ)."

Signed and Sealed this
Thirtieth Day of April, 2024

Katherine Kelly Vidal
*Director of the United States Patent and Trademark Office*

SEQUENCE LISTING

```
<160> NUMBER OF SEQ ID NOS: 37

<210> SEQ ID NO 1
<211> LENGTH: 549
<212> TYPE: DNA
<213> ORGANISM: Human immunodeficiency virus
<220> FEATURE:
<221> NAME/KEY: CDS
<222> LOCATION: (1)..(549)
<220> FEATURE:
<221> NAME/KEY: misc_difference
<222> LOCATION: (406)..(408)
<223> OTHER INFORMATION: artificial mutation

<400> SEQUENCE: 1 gtg tgg caa gta gac agg atg agg att aga aca tgg aac agt tta gta        48
Val Trp Gln Val Asp Arg Met Arg Ile Arg Thr Trp Asn Ser Leu Val
 1               5                  10                  15 aaa cat cac atg tat atc tca aag aaa gca aaa aat tgg ttt tat aga        96
Lys His His Met Tyr Ile Ser Lys Lys Ala Lys Asn Trp Phe Tyr Arg
             20                  25                  30 cat cac ttt gaa agc agt cat cca aga gta agt tca gaa gta cac atc       144
His His Phe Glu Ser Ser His Pro Arg Val Ser Ser Glu Val His Ile
         35                  40                  45 cca cta ggg gat gct aga tta gta gta aga aca tat tgg ggt ctg cat       192
Pro Leu Gly Asp Ala Arg Leu Val Val Arg Thr Tyr Trp Gly Leu His
     50                  55                  60 aca gga gaa aaa gat tgg cac ttg ggt aat ggg gtg tcc ata gaa tgg       240
Thr Gly Glu Lys Asp Trp His Leu Gly Asn Gly Val Ser Ile Glu Trp
 65                  70                  75                  80 aga cta aga aga tat agc aca caa ata gat cct gac ctg gca gac caa       288
Arg Leu Arg Arg Tyr Ser Thr Gln Ile Asp Pro Asp Leu Ala Asp Gln
                 85                  90                  95 cta att cat ctg cat tat ttt aat tgt ttt tca gac tct gcc ata agg       336
Leu Ile His Leu His Tyr Phe Asn Cys Phe Ser Asp Ser Ala Ile Arg
            100                 105                 110 aaa gcc ata tta gga caa gta gtt aga cct aga tgt gac tat caa gca       384
Lys Ala Ile Leu Gly Gln Val Val Arg Pro Arg Cys Asp Tyr Gln Ala
        115                 120                 125 gga cat aac aag gta gga tct gct caa tat ttg gca ctg aaa gca tta       432
Gly His Asn Lys Val Gly Ser Ala Gln Tyr Leu Ala Leu Lys Ala Leu
    130                 135                 140
```

```
gta aca cca gta agg aca agg cca cct ttg cct agt gtt agg aaa tta      480
Val Thr Pro Val Arg Thr Arg Pro Pro Leu Pro Ser Val Arg Lys Leu
145                 150                 155                 160 gca gag gac aga tgg aac aag ccc cag aaa acc agg ggt ccc aga ggg      528
Ala Glu Asp Arg Trp Asn Lys Pro Gln Lys Thr Arg Gly Pro Arg Gly
                165                 170                 175 agc cat aca atg aat gga cat                                          549
Ser His Thr Met Asn Gly His
            180
```

<210> SEQ ID NO 2
<211> LENGTH: 183
<212> TYPE: PRT
<213> ORGANISM: Human immunodeficiency virus

<400> SEQUENCE: 2

```
Val Trp Gln Val Asp Arg Met Arg Ile Arg Thr Trp Asn Ser Leu Val
1               5                   10                  15

Lys His His Met Tyr Ile Ser Lys Lys Ala Lys Asn Trp Phe Tyr Arg
                20                  25                  30

His His Phe Glu Ser Ser His Pro Arg Val Ser Ser Glu Val His Ile
            35                  40                  45

Pro Leu Gly Asp Ala Arg Leu Val Val Arg Thr Tyr Trp Gly Leu His
        50                  55                  60

Thr Gly Glu Lys Asp Trp His Leu Gly Asn Gly Val Ser Ile Glu Trp
65                  70                  75                  80

Arg Leu Arg Arg Tyr Ser Thr Gln Ile Asp Pro Asp Leu Ala Asp Gln
                85                  90                  95

Leu Ile His Leu His Tyr Phe Asn Cys Phe Ser Asp Ser Ala Ile Arg
            100                 105                 110

Lys Ala Ile Leu Gly Gln Val Val Arg Pro Arg Cys Asp Tyr Gln Ala
        115                 120                 125

Gly His Asn Lys Val Gly Ser Ala Gln Tyr Leu Ala Leu Lys Ala Leu
    130                 135                 140

Val Thr Pro Val Arg Thr Arg Pro Pro Leu Pro Ser Val Arg Lys Leu
145                 150                 155                 160

Ala Glu Asp Arg Trp Asn Lys Pro Gln Lys Thr Arg Gly Pro Arg Gly
                165                 170                 175

Ser His Thr Met Asn Gly His
            180
```

<210> SEQ ID NO 3
<211> LENGTH: 573
<212> TYPE: DNA
<213> ORGANISM: Artificial Sequence
<220> FEATURE:
<223> OTHER INFORMATION: Synthetic Sequence Vif variant construct

<400> SEQUENCE: 3

```
cctaggggta ccgaaatggt gtggcaagta gacaggatga ggattagaac atggaacagt     60
ttagtaaaac atcacatgta tatctcaaag aaagcaaaaa attggtttta tagacatcac    120
tttgaaagca gtcatccaag agtaagttca gaagtacaca tcccactagg ggatgctaga    180
ttagtagtaa gaacatattg gggtctgcat acaggagaaa aagattggca cttgggtaat    240
ggggtgtcca tagaatggag actaagaaga tatagcacac aaatagatcc tgacctggca    300
gaccaactaa ttcatctgca ttattttaat tgttttttcag actctgccat aaggaaagcc    360
```

-continued

```
atattaggac aagtagttag acctagatgt gactatcaag caggacataa caaggtagga      420
tctgctcaat atttggcact gaaagcatta gtaacaccag taaggacaag gccacctttg      480
cctagtgtta ggaaattagc agaggacaga tggaacaagc cccagaaaac cagggtccc       540 agagggagcc atacaatgaa tggacatgct agc                                   573
```

```
<210> SEQ ID NO 4
<211> LENGTH: 4116
<212> TYPE: DNA
<213> ORGANISM: Artificial Sequence
<220> FEATURE:
<223> OTHER INFORMATION: Synthetic Sequence Cas9 codon-optimized for
      human.
<220> FEATURE:
<221> NAME/KEY: CDS
<222> LOCATION: (1)..(4116)

<400> SEQUENCE: 4
```

```
atg gac aag aag tac tcc att ggg ctc gmt atc ggc aca aac agc gtc       48
Met Asp Lys Lys Tyr Ser Ile Gly Leu Xaa Ile Gly Thr Asn Ser Val
1               5                   10                  15 ggt tgg gcc gtc att acg gac gag tac aag gtg ccg agc aaa aaa ttc       96
Gly Trp Ala Val Ile Thr Asp Glu Tyr Lys Val Pro Ser Lys Lys Phe
            20                  25                  30 aaa gtt ctg ggc aat acc gat cgc cac agc ata aag aag aac ctc att       144
Lys Val Leu Gly Asn Thr Asp Arg His Ser Ile Lys Lys Asn Leu Ile
        35                  40                  45 ggc gcc ctc ctg ttc gac tcc ggg gag acg gcc gaa gcc acg cgg ctc       192
Gly Ala Leu Leu Phe Asp Ser Gly Glu Thr Ala Glu Ala Thr Arg Leu
    50                  55                  60 aaa aga aca gca cgg cgc aga tat acc cgc aga aag aat cgg atc tgc       240
Lys Arg Thr Ala Arg Arg Arg Tyr Thr Arg Arg Lys Asn Arg Ile Cys
65                  70                  75                  80 tac ctg cag gag atc ttt agt aat gag atg gct aag gtg gat gac tct       288
Tyr Leu Gln Glu Ile Phe Ser Asn Glu Met Ala Lys Val Asp Asp Ser
                85                  90                  95 ttc ttc cat agg ctg gag gag tcc ttt ttg gtg gag gag gat aaa aag       336
Phe Phe His Arg Leu Glu Glu Ser Phe Leu Val Glu Glu Asp Lys Lys
            100                 105                 110 cac gag cgc cac cca atc ttt ggc aat atc gtg gac gag gtg gcg tac       384
His Glu Arg His Pro Ile Phe Gly Asn Ile Val Asp Glu Val Ala Tyr
        115                 120                 125 cat gaa aag tac cca acc ata tat cat ctg agg aag aag ctt gta gac       432
His Glu Lys Tyr Pro Thr Ile Tyr His Leu Arg Lys Lys Leu Val Asp
    130                 135                 140 agt act gat aag gct gac ttg cgg ttg atc tat ctc gcg ctg gcg cat       480
Ser Thr Asp Lys Ala Asp Leu Arg Leu Ile Tyr Leu Ala Leu Ala His
145                 150                 155                 160 atg atc aaa ttt cgg gga cac ttc ctc atc gag ggg gac ctg aac cca       528
Met Ile Lys Phe Arg Gly His Phe Leu Ile Glu Gly Asp Leu Asn Pro
                165                 170                 175 gac aac agc gat gtc gac aaa ctc ttt atc caa ctg gtt cag act tac       576
Asp Asn Ser Asp Val Asp Lys Leu Phe Ile Gln Leu Val Gln Thr Tyr
            180                 185                 190 aat cag ctt ttc gaa gag aac ccg atc aac gca tcc gga gtt gac gcc       624
Asn Gln Leu Phe Glu Glu Asn Pro Ile Asn Ala Ser Gly Val Asp Ala
        195                 200                 205 aaa gca atc ctg agc gct agg ctg tcc aaa tcc cgg cgg ctc gaa aac       672
Lys Ala Ile Leu Ser Ala Arg Leu Ser Lys Ser Arg Arg Leu Glu Asn
    210                 215                 220 ctc atc gca cag ctc cct ggg gag aag aag aac ggc ctg ttt ggt aat       720
```

```
            Leu Ile Ala Gln Leu Pro Gly Glu Lys Lys Asn Gly Leu Phe Gly Asn
            225                 230                 235                 240 ctt atc gcc ctg tca ctc ggg ctg acc ccc aac ttt aaa tct aac ttc          768
Leu Ile Ala Leu Ser Leu Gly Leu Thr Pro Asn Phe Lys Ser Asn Phe
                        245                 250                 255 gac ctg gcc gaa gat gcc aag ctt caa ctg agc aaa gac acc tac gat          816
Asp Leu Ala Glu Asp Ala Lys Leu Gln Leu Ser Lys Asp Thr Tyr Asp
                260                 265                 270 gat gat ctc gac aat ctg ctg gcc cag atc ggc gac cag tac gca gac          864
Asp Asp Leu Asp Asn Leu Leu Ala Gln Ile Gly Asp Gln Tyr Ala Asp
        275                 280                 285 ctt ttt ttg gcg gca aag aac ctg tca gac gcc att ctg ctg agt gat          912
Leu Phe Leu Ala Ala Lys Asn Leu Ser Asp Ala Ile Leu Leu Ser Asp
290                 295                 300 att ctg cga gtg aac acg gag atc acc aaa gct ccg ctg agc gct agt          960
Ile Leu Arg Val Asn Thr Glu Ile Thr Lys Ala Pro Leu Ser Ala Ser
305                 310                 315                 320 atg atc aag cgc tat gat gag cac cac caa gac ttg act ttg ctg aag         1008
Met Ile Lys Arg Tyr Asp Glu His His Gln Asp Leu Thr Leu Leu Lys
                325                 330                 335 gcc ctt gtc aga cag caa ctg cct gag aag tac aag gaa att ttc ttc         1056
Ala Leu Val Arg Gln Gln Leu Pro Glu Lys Tyr Lys Glu Ile Phe Phe
                340                 345                 350 gat cag tct aaa aat ggc tac gcc gga tac att gac ggc gga gca agc         1104
Asp Gln Ser Lys Asn Gly Tyr Ala Gly Tyr Ile Asp Gly Gly Ala Ser
                355                 360                 365 cag gag gaa ttt tac aaa ttt att aag ccc atc ttg gaa aaa atg gac         1152
Gln Glu Glu Phe Tyr Lys Phe Ile Lys Pro Ile Leu Glu Lys Met Asp
370                 375                 380 ggc acc gag gag ctg ctg gta aag ctt aac aga gaa gat ctg ttg cgc         1200
Gly Thr Glu Glu Leu Leu Val Lys Leu Asn Arg Glu Asp Leu Leu Arg
385                 390                 395                 400 aaa cag cgc act ttc gac aat gga agc atc ccc cac cag att cac ctg         1248
Lys Gln Arg Thr Phe Asp Asn Gly Ser Ile Pro His Gln Ile His Leu
                405                 410                 415 ggc gaa ctg cac gct atc ctc agg cgg caa gag gat ttc tac ccc ttt         1296
Gly Glu Leu His Ala Ile Leu Arg Arg Gln Glu Asp Phe Tyr Pro Phe
                420                 425                 430 ttg aaa gat aac agg gaa aag att gag aaa atc ctc aca ttt cgg ata         1344
Leu Lys Asp Asn Arg Glu Lys Ile Glu Lys Ile Leu Thr Phe Arg Ile
                435                 440                 445 ccc tac tat gta ggc ccc ctc gcc cgg gga aat tcc aga ttc gcg tgg         1392
Pro Tyr Tyr Val Gly Pro Leu Ala Arg Gly Asn Ser Arg Phe Ala Trp
450                 455                 460 atg act cgc aaa tca gaa gag acc atc act ccc tgg aac ttc gag gaa         1440
Met Thr Arg Lys Ser Glu Glu Thr Ile Thr Pro Trp Asn Phe Glu Glu
465                 470                 475                 480 gtc gtg gat aag ggg gcc tct gcc cag tcc ttc atc gaa agg atg act         1488
Val Val Asp Lys Gly Ala Ser Ala Gln Ser Phe Ile Glu Arg Met Thr
                485                 490                 495 aac ttt gat aaa aat ctg cct aac gaa aag gtg ctt cct aaa cac tct         1536
Asn Phe Asp Lys Asn Leu Pro Asn Glu Lys Val Leu Pro Lys His Ser
                500                 505                 510 ctg ctg tac gag tac ttc aca gtt tat aac gag ctc acc aag gtc aaa         1584
Leu Leu Tyr Glu Tyr Phe Thr Val Tyr Asn Glu Leu Thr Lys Val Lys
                515                 520                 525 tac gtc aca gaa ggg atg aga aag cca gca ttc ctg tct gga gag cag         1632
Tyr Val Thr Glu Gly Met Arg Lys Pro Ala Phe Leu Ser Gly Glu Gln
530                 535                 540
```

-continued

| | | |
|---|---|---|
| aag aaa gct atc gtg gac ctc ctc ttc aag acg aac cgg aaa gtt acc<br>Lys Lys Ala Ile Val Asp Leu Leu Phe Lys Thr Asn Arg Lys Val Thr<br>545                     550                     555                     560 | 1680 | |
| gtg aaa cag ctc aaa gaa gac tat ttc aaa aag att gaa tgt ttc gac<br>Val Lys Gln Leu Lys Glu Asp Tyr Phe Lys Lys Ile Glu Cys Phe Asp<br>                     565                     570                     575 | 1728 | |
| tct gtt gaa atc agc gga gtg gag gat cgc ttc aac gca tcc ctg gga<br>Ser Val Glu Ile Ser Gly Val Glu Asp Arg Phe Asn Ala Ser Leu Gly<br>                     580                     585                     590 | 1776 | |
| acg tat cac gat ctc ctg aaa atc att aaa gac aag gac ttc ctg gac<br>Thr Tyr His Asp Leu Leu Lys Ile Ile Lys Asp Lys Asp Phe Leu Asp<br>               595                     600                     605 | 1824 | |
| aat gag gag aac gag gac att ctt gag gac att gtc ctc acc ctt acg<br>Asn Glu Glu Asn Glu Asp Ile Leu Glu Asp Ile Val Leu Thr Leu Thr<br>610                     615                     620 | 1872 | |
| ttg ttt gaa gat agg gag atg att gaa gaa cgc ttg aaa act tac gct<br>Leu Phe Glu Asp Arg Glu Met Ile Glu Glu Arg Leu Lys Thr Tyr Ala<br>625                     630                     635                     640 | 1920 | |
| cat ctc ttc gac gac aaa gtc atg aaa cag ctc aag agg cgc cga tat<br>His Leu Phe Asp Asp Lys Val Met Lys Gln Leu Lys Arg Arg Arg Tyr<br>                     645                     650                     655 | 1968 | |
| aca gga tgg ggg cgg ctg tca aga aaa ctg atc aat ggg atc cga gac<br>Thr Gly Trp Gly Arg Leu Ser Arg Lys Leu Ile Asn Gly Ile Arg Asp<br>               660                     665                     670 | 2016 | |
| aag cag agt gga aag aca atc ctg gat ttt ctt aag tcc gat gga ttt<br>Lys Gln Ser Gly Lys Thr Ile Leu Asp Phe Leu Lys Ser Asp Gly Phe<br>             675                     680                     685 | 2064 | |
| gcc aac cgg aac ttc atg cag ttg atc cat gat gac tct ctc acc ttt<br>Ala Asn Arg Asn Phe Met Gln Leu Ile His Asp Asp Ser Leu Thr Phe<br>690                     695                     700 | 2112 | |
| aag gag gac atc cag aaa gca caa gtt tct ggc cag ggg gac agt ctt<br>Lys Glu Asp Ile Gln Lys Ala Gln Val Ser Gly Gln Gly Asp Ser Leu<br>705                     710                     715                     720 | 2160 | |
| cac gag cac atc gct aat ctt gca ggt agc cca gct atc aaa aag gga<br>His Glu His Ile Ala Asn Leu Ala Gly Ser Pro Ala Ile Lys Lys Gly<br>                     725                     730                     735 | 2208 | |
| ata ctg cag acc gtt aag gtc gtg gat gaa ctc gtc aaa gta atg gga<br>Ile Leu Gln Thr Val Lys Val Val Asp Glu Leu Val Lys Val Met Gly<br>               740                     745                     750 | 2256 | |
| agg cat aag ccc gag aat atc gtt atc gag atg gcc cga gag aac caa<br>Arg His Lys Pro Glu Asn Ile Val Ile Glu Met Ala Arg Glu Asn Gln<br>755                     760                     765 | 2304 | |
| act acc cag aag gga cag aag aac agt agg gaa agg atg aag agg att<br>Thr Thr Gln Lys Gly Gln Lys Asn Ser Arg Glu Arg Met Lys Arg Ile<br>770                     775                     780 | 2352 | |
| gaa gag ggt ata aaa gaa ctg ggg tcc caa atc ctt aag gaa cac cca<br>Glu Glu Gly Ile Lys Glu Leu Gly Ser Gln Ile Leu Lys Glu His Pro<br>785                     790                     795                     800 | 2400 | |
| gtt gaa aac acc cag ctt cag aat gag aag ctc tac ctg tac tac ctg<br>Val Glu Asn Thr Gln Leu Gln Asn Glu Lys Leu Tyr Leu Tyr Tyr Leu<br>                     805                     810                     815 | 2448 | |
| cag aac ggc agg gac atg tac gtg gat cag gaa ctg gac atc aat cgg<br>Gln Asn Gly Arg Asp Met Tyr Val Asp Gln Glu Leu Asp Ile Asn Arg<br>               820                     825                     830 | 2496 | |
| ctc tcc gac tac gac gtg gat smt atc gtg ccc cag tct ttt ctc aaa<br>Leu Ser Asp Tyr Asp Val Asp Xaa Ile Val Pro Gln Ser Phe Leu Lys<br>             835                     840                     845 | 2544 | |
| gat gat tct att gat aat aaa gtg ttg aca aga tcc gat aaa aat aga<br>Asp Asp Ser Ile Asp Asn Lys Val Leu Thr Arg Ser Asp Lys Asn Arg<br>850                     855                     860 | 2592 | |

-continued

| | |
|---|---|
| ggg aag agt gat aac gtc ccc tca gaa gaa gtt gtc aag aaa atg aaa<br>Gly Lys Ser Asp Asn Val Pro Ser Glu Glu Val Val Lys Lys Met Lys<br>865          870              875              880 | 2640 |
| aat tat tgg cgg cag ctg ctg aac gcc aaa ctg atc aca caa cgg aag<br>Asn Tyr Trp Arg Gln Leu Leu Asn Ala Lys Leu Ile Thr Gln Arg Lys<br>                    885              890              895 | 2688 |
| ttc gat aat ctg act aag gct gaa cga ggt ggc ctg tct gag ttg gat<br>Phe Asp Asn Leu Thr Lys Ala Glu Arg Gly Gly Leu Ser Glu Leu Asp<br>900                  905                  910 | 2736 |
| aaa gcc ggc ttc atc aaa agg cag ctt gtt gag aca cgc cag atc acc<br>Lys Ala Gly Phe Ile Lys Arg Gln Leu Val Glu Thr Arg Gln Ile Thr<br>                    915              920              925 | 2784 |
| aag cac gtg gcc caa att ctc gat tca cgc atg aac acc aag tac gat<br>Lys His Val Ala Gln Ile Leu Asp Ser Arg Met Asn Thr Lys Tyr Asp<br>930                  935                  940 | 2832 |
| gaa aat gac aaa ctg att cga gag gtg aaa gtt att act ctg aag tct<br>Glu Asn Asp Lys Leu Ile Arg Glu Val Lys Val Ile Thr Leu Lys Ser<br>945          950              955              960 | 2880 |
| aag ctg gtc tca gat ttc aga aag gac ttt cag ttt tat aag gtg aga<br>Lys Leu Val Ser Asp Phe Arg Lys Asp Phe Gln Phe Tyr Lys Val Arg<br>                    965              970              975 | 2928 |
| gag atc aac aat tac cac cat gcg cat gat gcc tac ctg aat gca gtg<br>Glu Ile Asn Asn Tyr His His Ala His Asp Ala Tyr Leu Asn Ala Val<br>980                  985                  990 | 2976 |
| gta ggc act gca ctt atc aaa aaa tat ccc aag ctt gaa tct gaa ttt<br>Val Gly Thr Ala Leu Ile Lys Lys Tyr Pro Lys Leu Glu Ser Glu Phe<br>                    995           1000            1005 | 3024 |
| gtt tac gga gac tat aaa gtg tac gat gtt agg aaa atg atc gca<br>Val Tyr Gly Asp Tyr Lys Val Tyr Asp Val Arg Lys Met Ile Ala<br>1010                   1015              1020 | 3069 |
| aag tct gag cag gaa ata ggc aag gcc acc gct aag tac ttc ttt<br>Lys Ser Glu Gln Glu Ile Gly Lys Ala Thr Ala Lys Tyr Phe Phe<br>1025                   1030              1035 | 3114 |
| tac agc aat att atg aat ttt ttc aag acc gag att aca ctg gcc<br>Tyr Ser Asn Ile Met Asn Phe Phe Lys Thr Glu Ile Thr Leu Ala<br>1040                   1045              1050 | 3159 |
| aat gga gag att cgg aag cga cca ctt atc gaa aca aac gga gaa<br>Asn Gly Glu Ile Arg Lys Arg Pro Leu Ile Glu Thr Asn Gly Glu<br>1055                   1060              1065 | 3204 |
| aca gga gaa atc gtg tgg gac aag ggt agg gat ttc gcg aca gtc<br>Thr Gly Glu Ile Val Trp Asp Lys Gly Arg Asp Phe Ala Thr Val<br>1070                   1075              1080 | 3249 |
| cgg aag gtc ctg tcc atg ccg cag gtg aac atc gtt aaa aag acc<br>Arg Lys Val Leu Ser Met Pro Gln Val Asn Ile Val Lys Lys Thr<br>1085                   1090              1095 | 3294 |
| gaa gta cag acc gga ggc ttc tcc aag gaa agt atc ctc ccg aaa<br>Glu Val Gln Thr Gly Gly Phe Ser Lys Glu Ser Ile Leu Pro Lys<br>1100                   1105              1110 | 3339 |
| agg aac agc gac aag ctg atc gca cgc aaa aaa gat tgg gac ccc<br>Arg Asn Ser Asp Lys Leu Ile Ala Arg Lys Lys Asp Trp Asp Pro<br>1115                   1120              1125 | 3384 |
| aag aaa tac ggc gga ttc gat tct cct aca gtc gct tac agt gta<br>Lys Lys Tyr Gly Gly Phe Asp Ser Pro Thr Val Ala Tyr Ser Val<br>1130                   1135              1140 | 3429 |
| ctg gtt gtg gcc aaa gtg gag aaa ggg aag tct aaa aaa ctc aaa<br>Leu Val Val Ala Lys Val Glu Lys Gly Lys Ser Lys Lys Leu Lys<br>1145                   1150              1155 | 3474 |
| agc gtc aag gaa ctg ctg ggc atc aca atc atg gag cga tca agc<br>Ser Val Lys Glu Leu Leu Gly Ile Thr Ile Met Glu Arg Ser Ser | 3519 |

```
ttc gaa aaa aac ccc atc gac ttt ctc gag gcg aaa gga tat aaa    3564
Phe Glu Lys Asn Pro Ile Asp Phe Leu Glu Ala Lys Gly Tyr Lys
    1175                1180                1185 gag gtc aaa aaa gac ctc atc att aag ctt ccc aag tac tct ctc    3609
Glu Val Lys Lys Asp Leu Ile Ile Lys Leu Pro Lys Tyr Ser Leu
1190                1195                1200 ttt gag ctt gaa aac ggc cgg aaa cga atg ctc gct agt gcg ggc    3654
Phe Glu Leu Glu Asn Gly Arg Lys Arg Met Leu Ala Ser Ala Gly
    1205                1210                1215 gag ctg cag aaa ggt aac gag ctg gca ctg ccc tct aaa tac gtt    3699
Glu Leu Gln Lys Gly Asn Glu Leu Ala Leu Pro Ser Lys Tyr Val
1220                1225                1230 aat ttc ttg tat ctg gcc agc cac tat gaa aag ctc aaa ggg tct    3744
Asn Phe Leu Tyr Leu Ala Ser His Tyr Glu Lys Leu Lys Gly Ser
    1235                1240                1245 ccc gaa gat aat gag cag aag cag ctg ttc gtg gaa caa cac aaa    3789
Pro Glu Asp Asn Glu Gln Lys Gln Leu Phe Val Glu Gln His Lys
1250                1255                1260 cac tac ctt gat gag atc atc gag caa ata agc gaa ttc tcc aaa    3834
His Tyr Leu Asp Glu Ile Ile Glu Gln Ile Ser Glu Phe Ser Lys
    1265                1270                1275 aga gtg atc ctc gcc gac gct aac ctc gat aag gtg ctt tct gct    3879
Arg Val Ile Leu Ala Asp Ala Asn Leu Asp Lys Val Leu Ser Ala
1280                1285                1290 tac aat aag cac agg gat aag ccc atc agg gag cag gca gaa aac    3924
Tyr Asn Lys His Arg Asp Lys Pro Ile Arg Glu Gln Ala Glu Asn
    1295                1300                1305 att atc cac ttg ttt act ctg acc aac ttg ggc gcg cct gca gcc    3969
Ile Ile His Leu Phe Thr Leu Thr Asn Leu Gly Ala Pro Ala Ala
1310                1315                1320 ttc aag tac ttc gac acc acc ata gac aga aag cgg tac acc tct    4014
Phe Lys Tyr Phe Asp Thr Thr Ile Asp Arg Lys Arg Tyr Thr Ser
    1325                1330                1335 aca aag gag gtc ctg gac gcc aca ctg att cat cag tca att acg    4059
Thr Lys Glu Val Leu Asp Ala Thr Leu Ile His Gln Ser Ile Thr
1340                1345                1350 ggg ctc tat gaa aca aga atc gac ctc tct cag ctc ggt gga gac    4104
Gly Leu Tyr Glu Thr Arg Ile Asp Leu Ser Gln Leu Gly Gly Asp
    1355                1360                1365 agc agg gct gac                                                 4116
Ser Arg Ala Asp
1370

<210> SEQ ID NO 5
<211> LENGTH: 1372
<212> TYPE: PRT
<213> ORGANISM: Artificial Sequence
<220> FEATURE:
<221> NAME/KEY: misc_feature
<222> LOCATION: (10)..(10)
<223> OTHER INFORMATION: The 'Xaa' at location 10 stands for Asp, or
      Ala.
<220> FEATURE:
<221> NAME/KEY: misc_feature
<222> LOCATION: (840)..(840)
<223> OTHER INFORMATION: The 'Xaa' at location 840 stands for Asp, Ala,
      His, or Pro.
<220> FEATURE:
<223> OTHER INFORMATION: Synthetic Construct

<400> SEQUENCE: 5

Met Asp Lys Lys Tyr Ser Ile Gly Leu Xaa Ile Gly Thr Asn Ser Val
```

```
  1               5                   10                  15
Gly Trp Ala Val Ile Thr Asp Glu Tyr Lys Val Pro Ser Lys Lys Phe
            20                  25              30
Lys Val Leu Gly Asn Thr Asp Arg His Ser Ile Lys Lys Asn Leu Ile
            35                  40              45
Gly Ala Leu Leu Phe Asp Ser Gly Glu Thr Ala Glu Ala Thr Arg Leu
            50                  55              60
Lys Arg Thr Ala Arg Arg Tyr Thr Arg Arg Lys Asn Arg Ile Cys
65                  70                  75              80
Tyr Leu Gln Glu Ile Phe Ser Asn Glu Met Ala Lys Val Asp Asp Ser
                85                  90              95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
                115                 120                 125
His Glu Lys Tyr Pro Thr Ile Tyr His Leu Arg Lys Lys Leu Val Asp
                130                 135             140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
                180                 185                 190
Asn Gln Leu Phe Glu Glu Asn Pro Ile Asn Ala Ser Gly Val Asp Ala
                195                 200                 205
Lys Ala Ile Leu Ser Ala Arg Leu Ser Lys Ser Arg Arg Leu Glu Asn
                210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
                275                 280                 285
Leu Phe Leu Ala Ala Lys Asn Leu Ser Asp Ala Ile Leu Leu Ser Asp
                290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
                370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
```

-continued

```
Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Xaa Ile Val Pro Gln Ser Phe Leu Lys
            835                 840                 845
```

```
Asp Asp Ser Ile Asp Asn Lys Val Leu Thr Arg Ser Asp Lys Asn Arg
    850                 855                 860

Gly Lys Ser Asp Asn Val Pro Ser Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
```

-continued

```
             1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Ser Arg Ala Asp
    1370

<210> SEQ ID NO 6
<211> LENGTH: 21
<212> TYPE: DNA
<213> ORGANISM: Artificial Sequence
<220> FEATURE:
<223> OTHER INFORMATION: Synthetic Sequence SV40-derived nuclear
      localization signal
<220> FEATURE:
<221> NAME/KEY: CDS
<222> LOCATION: (1)..(21)

<400> SEQUENCE: 6 cct aag aag aar mgk aar gtw                                           21
Pro Lys Lys Lys Xaa Lys Xaa
1               5

<210> SEQ ID NO 7
<211> LENGTH: 7
<212> TYPE: PRT
<213> ORGANISM: Artificial Sequence
<220> FEATURE:
<221> NAME/KEY: misc_feature
<222> LOCATION: (5)..(5)
<223> OTHER INFORMATION: The 'Xaa' at location 5 stands for Arg, or
      Ser.
<220> FEATURE:
<221> NAME/KEY: misc_feature
<222> LOCATION: (7)..(7)
<223> OTHER INFORMATION: The 'Xaa' at location 7 stands for Val.
<220> FEATURE:
<223> OTHER INFORMATION: Synthetic Construct

<400> SEQUENCE: 7

Pro Lys Lys Lys Xaa Lys Xaa
1               5

<210> SEQ ID NO 8
<211> LENGTH: 51
<212> TYPE: DNA
<213> ORGANISM: Artificial Sequence
<220> FEATURE:
<223> OTHER INFORMATION: Synthetic Sequence SV40-derived nuclear
      localization signal
<220> FEATURE:
<221> NAME/KEY: CDS
<222> LOCATION: (1)..(51)
<220> FEATURE:
<221> NAME/KEY: misc_feature
```

```
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 8 atg gcn ccn aar aar aar agr aar gtn ggn ath cay ggn gtn ccn gcn      48
Met Ala Pro Lys Lys Lys Arg Lys Val Gly Ile His Gly Val Pro Ala
1               5                   10                  15 gcn                                                                  51
Ala

<210> SEQ ID NO 9
<211> LENGTH: 17
<212> TYPE: PRT
<213> ORGANISM: Artificial Sequence
<220> FEATURE:
<223> OTHER INFORMATION: Synthetic Construct

<400> SEQUENCE: 9

Met Ala Pro Lys Lys Lys Arg Lys Val Gly Ile His Gly Val Pro Ala
1               5                   10                  15

Ala

<210> SEQ ID NO 10
<211> LENGTH: 19
<212> TYPE: RNA
<213> ORGANISM: Francisella novicida
<220> FEATURE:
<221> NAME/KEY: misc_structure
<222> LOCATION: (1)..(19)
<223> OTHER INFORMATION: crRNA direct repeat sequence.

<400> SEQUENCE: 10
aauuucuacu guguagau                                                  19

<210> SEQ ID NO 11
<211> LENGTH: 76
<212> TYPE: DNA
<213> ORGANISM: Streptococcus pyogenes
<220> FEATURE:
<221> NAME/KEY: misc_structure
```

```
<222> LOCATION: (1)..(76)
<223> OTHER INFORMATION: tracrRNA

<400> SEQUENCE: 11
gttttagagc tagaaatagc aagttaaaat aaggctagtc cgttatcaac ttgaaaaagt    60
ggcaccgagt cggtgc                                                    76

<210> SEQ ID NO 12
<211> LENGTH: 20
<212> TYPE: DNA
<213> ORGANISM: Homo sapiens

<400> SEQUENCE: 12
aatgcagact ttgctttcct                                                20

<210> SEQ ID NO 13
<211> LENGTH: 8604
<212> TYPE: DNA
<213> ORGANISM: Artificial Sequence
<220> FEATURE:
<223> OTHER INFORMATION: Synthetic Sequence Complete nucleotide
      sequence of vector 1922
<220> FEATURE:
<221> NAME/KEY: promoter
<222> LOCATION: (2233)..(2461)
<223> OTHER INFORMATION: H1 promoter
<220> FEATURE:
<221> NAME/KEY: misc_feature
<222> LOCATION: (2462)..(2481)
<223> OTHER INFORMATION: Target(HPRT site 3)
<220> FEATURE:
<221> NAME/KEY: misc_structure
<222> LOCATION: (2482)..(2557)
<223> OTHER INFORMATION: tracrRNA
<220> FEATURE:
<221> NAME/KEY: promoter
<222> LOCATION: (2572)..(2826)
<223> OTHER INFORMATION: CMV promoter
<220> FEATURE:
<221> NAME/KEY: misc_feature
<222> LOCATION: (3232)..(3237)
<223> OTHER INFORMATION: NheI recognition site
<220> FEATURE:
<221> NAME/KEY: misc_feature
<222> LOCATION: (3241)..(3291)
<223> OTHER INFORMATION: NLS
<220> FEATURE:
<221> NAME/KEY: gene
<222> LOCATION: (3292)..(7407)
<223> OTHER INFORMATION: nCas9
<220> FEATURE:
<221> NAME/KEY: misc_feature
<222> LOCATION: (7408)..(7428)
<223> OTHER INFORMATION: NLS
<220> FEATURE:
<221> NAME/KEY: misc_feature
<222> LOCATION: (7444)..(7449)
<223> OTHER INFORMATION: AvrII recognition site
<220> FEATURE:
<221> NAME/KEY: misc_feature
<222> LOCATION: (7453)..(7506)
<223> OTHER INFORMATION: T2A
<220> FEATURE:
<221> NAME/KEY: gene
<222> LOCATION: (7513)..(7767)
<223> OTHER INFORMATION: NeoR

<400> SEQUENCE: 13
ggccgccacc gcggtggagc tccagctttt gttcccttta gtgagggtta attgcgcgct    60
tggcgtaatc atggtcatag ctgtttcctg tgtgaaattg ttatccgctc acaattccac   120
acaacatacg agccggaagc ataaagtgta aagcctgggg tgcctaatga gtgagctaac   180
```

```
tcacattaat tgcgttgcgc tcactgcccg ctttccagtc gggaaacctg tcgtgccagc      240
tgcattaatg aatcggccaa cgcgcgggga gaggcggttt gcgtattggg cgctcttccg      300
cttcctcgct cactgactcg ctgcgctcgg tcgttcggct gcggcgagcg gtatcagctc      360
actcaaaggc ggtaatacgg ttatccacag aatcagggga taacgcagga agaacatgt      420 gagcaaaagg ccagcaaaag gccaggaacc gtaaaaaggc cgcgttgctg gcgttttcc      480 ataggctccg cccccctgac gagcatcaca aaaatcgacg ctcaagtcag aggtggcgaa      540
acccgacagg actataaaga taccaggcgt ttccccctgg aagctccctc gtgcgctctc      600
ctgttccgac cctgccgctt accggatacc tgtccgcctt tctcccttcg ggaagcgtgg      660
cgctttctca tagctcacgc tgtaggtatc tcagttcggt gtaggtcgtt cgctccaagc      720
tgggctgtgt gcacgaaccc cccgttcagc ccgaccgctg cgccttatcc ggtaactatc      780
gtcttgagtc caacccggta agacacgact tatcgccact ggcagcagcc actggtaaca      840
ggattagcag agcgaggtat gtaggcggtg ctacagagtt cttgaagtgg tggcctaact      900
acggctacac tagaaggaca gtatttggta tctgcgctct gctgaagcca gttaccttcg      960
gaaaaagagt tggtagctct tgatccggca aacaaaccac cgctggtagc ggtggttttt     1020
ttgtttgcaa gcagcagatt acgcgcagaa aaaaggatc tcaagaagat cctttgatct     1080
tttctacggg gtctgacgct cagtggaacg aaaactcacg ttaagggatt ttggtcatga     1140
gattatcaaa aaggatcttc acctagatcc ttttaaatta aaaatgaagt tttaaatcaa     1200
tctaaagtat atatgagtaa acttggtctg acagttacca atgcttaatc agtgaggcac     1260
ctatctcagc gatctgtcta tttcgttcat ccatagttgc ctgactcccc gtcgtgtaga     1320
taactacgat acgggagggc ttaccatctg gccccagtgc tgcaatgata ccgcgagacc     1380
cacgctcacc ggctccagat ttatcagcaa taaaccagcc agccggaagg gccgagcgca     1440
gaagtggtcc tgcaacttta tccgcctcca tccagtctat taattgttgc cgggaagcta     1500
gagtaagtag ttcgccagtt aatagtttgc gcaacgttgt tgccattgct acaggcatcg     1560
tggtgtcacg ctcgtcgttt ggtatggctt cattcagctc cggttcccaa cgatcaaggc     1620
gagttacatg atcccccatg ttgtgcaaaa aagcggttag ctccttcggt cctccgatcg     1680
ttgtcagaag taagttggcc gcagtgttat cactcatggt tatggcagca ctgcataatt     1740
ctcttactgt catgccatcc gtaagatgct tttctgtgac tggtgagtac tcaaccaagt     1800
cattctgaga atagtgtatg cggcgaccga gttgctcttg cccggcgtca atacgggata     1860
ataccgcgcc acatagcaga actttaaaag tgctcatcat tggaaaacgt tcttcggggc     1920
gaaaactctc aaggatctta ccgctgttga tccagttc gatgtaaccc actcgtgcac     1980
ccaactgatc ttcagcatct tttactttca ccagcgtttc tgggtgagca aaaacaggaa     2040
ggcaaaatgc cgcaaaaaag ggaataaggg cgacacggaa atgttgaata ctcatactct     2100
tcctttttca atattattga agcatttatc agggttattg tctcatgagc ggatacatat     2160
ttgaatgtat ttagaaaaat aaacaaatag gggttccgcg cacatttccc cgaaaagtgc     2220
caccggtgta ccaattcgaa cgctgacgtc atcaacccgc tccaaggaat cgcgggccca     2280
gtgtcactag gcgggaacac ccagcgcgcg tgcgccctgg caggaagatg gctgtgaggg     2340
acaggggagt ggcgccctgc aatatttgca tgtcgctatg tgttctggga aatcaccata     2400
aacgtgaaat gtctttggat ttgggaatct tataagttct gtatgaggac cacagatccc     2460
caatgcagac tttgctttcc tgtttttagag ctagaaatag caagttaaaa taaggctagt     2520
```

```
ccgttatcaa cttgaaaaag tggcaccgag tcggtgcttt ttttacgcgt tgacattgat      2580
tattgactag ttattaatag taatcaatta cggggtcatt agttcatagc ccatatatgg      2640
agttccgcgt tacataactt acggtaaatg gcccgcctgg ctgaccgccc aacgacccc       2700 gcccattgac gtcaataatg acgtatgttc ccatagtaac gccaataggg actttccatt      2760
gacgtcaatg ggtggagtat ttacggtaaa ctgcccactt ggcagtacat caagtgtatc      2820
atatgccaag tacgccccct attgacgtca atgacggtaa atggcccgcc tggcattatg      2880
cccagtacat gaccttatgg gactttccta cttggcagta catctacgta ttagtcatcg      2940
ctattaccat ggtgatgcgg ttttggcagt acatcaatgg gcgtggatag cggtttgact      3000
cacggggatt tccaagtctc cacccccattg acgtcaatgg gagtttgttt tggcaccaaa     3060
atcaacggga ctttccaaaa tgtcgtaaca actccgcccc attgacgcaa atgggcggta     3120
ggcgtgtacg gtgggaggtc tatataagca gagctctctg gctaactaga acccactg       3180 cttactggct tatcgaaatt aatacgactc actataggga gacccaagct ggctagcgaa     3240
atggcaccga agaagaagcg taaagtcgga atccacggag ttcctgcggc aatggacaag     3300
aagtactcca ttgggctcgc tatcggcaca acagcgtcg gttgggccgt cattacggac      3360
gagtacaagg tgccgagcaa aaaattcaaa gttctgggca ataccgatcg ccacagcata     3420
aagaagaacc tcattggcgc cctcctgttc gactccgggg agacggccga agccacgcgg     3480
ctcaaaagaa cagcacggcg cagatatacc cgcagaaaga tcggatctg ctacctgcag      3540 gagatcttta gtaatgagat ggctaaggtg gatgactctt tcttccatag gctggaggag     3600 tccttttttgg tggaggagga taaaaagcac gagcgccacc caatctttgg caatatcgtg    3660
gacgaggtgg cgtaccatga aaagtaccca accatatatc atctgaggaa gaagcttgta    3720
gacagtactg ataaggctga cttgcggttg atctatctcg cgctggcgca tatgatcaaa    3780
tttcggggac acttcctcat cgagggggac ctgaacccag acaacagcga tgtcgacaaa    3840
ctctttatcc aactggttca gacttacaat cagcttttcg aagagaaccc gatcaacgca    3900
tccggagttg acgccaaagc aatcctgagc gctaggctgt ccaaatcccg gcggctcgaa    3960
aacctcatcg cacagctccc tggggagaag aagaacggcc tgtttggtaa tcttatcgcc    4020
ctgtcactcg ggctgacccc caactttaaa tctaacttcg acctggccga agatgccaag    4080
cttcaactga gcaaagacac ctacgatgat gatctcgaca atctgctggc ccagatcggc    4140
gaccagtacg cagaccttt tttggcggca aagaacctgt cagacgccat tctgctgagt    4200
gatattctgc gagtgaacac ggagatcacc aaagctccgc tgagcgctag tatgatcaag    4260
cgctatgatg agcaccacca agacttgact ttgctgaagg cccttgtcag acagcaactg    4320
cctgagaagt acaaggaaat tttcttcgat cagtctaaaa atggctacgc cggatacatt    4380
gacggcggag caagccagga ggaattttac aaatttatta gcccatcttt ggaaaaaatg    4440
gacggcaccg aggagctgct ggtaaagctt aacagagaag atctgttgcg caaacagcgc    4500
actttcgaca atggaagcat ccccaccag attcacctgg cgaactgca cgctatcctc     4560 aggcggcaag aggatttcta ccccttttg aaagataaca gggaaaagat tgagaaaatc    4620
ctcacatttc ggataccta ctatgtaggc ccctcgccc ggggaaattc cagattcgcg     4680
tggatgactc gcaaatcaga agagaccatc actccctgga acttcgagga agtcgtggat   4740 aaggggggcct ctgcccagtc cttcatcgaa aggatgacta actttgataa aaatctgcct   4800
aacgaaaagg tgcttcctaa acactctctg ctgtacgagt acttcacagt ttataacgag   4860
ctcaccaagg tcaaatacgt cacagaaggg atgagaaagc cagcattcct gtctggagag   4920
```

```
cagaagaaag ctatcgtgga cctcctcttc aagacgaacc ggaaagttac cgtgaaacag   4980
ctcaaagaag actatttcaa aaagattgaa tgtttcgact ctgttgaaat cagcggagtg   5040
gaggatcgct tcaacgcatc cctgggaacg tatcacgatc tcctgaaaat cattaaagac   5100
aaggacttcc tggacaatga ggagaacgag gacattcttg aggacattgt cctcaccctt   5160
acgttgtttg aagataggga gatgattgaa gaacgcttga aaacttacgc tcatctcttc   5220
gacgacaaag tcatgaaaca gctcaagagg cgccgatata caggatgggg gcggctgtca   5280
agaaaactga tcaatgggat ccgagacaag cagagtggaa agacaatcct ggattttctt   5340
aagtccgatg gatttgccaa ccggaacttc atgcagttga tccatgatga ctctctcacc   5400
tttaaggagg acatccagaa agcacaagtt tctggccagg gggacagtct tcacgagcac   5460
atcgctaatc ttgcaggtag cccagctatc aaaaagggaa tactgcagac cgttaaggtc   5520
gtggatgaac tcgtcaaagt aatgggaagg cataagcccg agaatatcgt tatcgagatg   5580
gcccgagaga accaaactac ccagaaggga cagaagaaca gtagggaaag gatgaagagg   5640
attgaagagg gtataaaaga actggggtcc caaatcctta aggaacaccc agttgaaaac   5700
acccagcttc agaatgagaa gctctacctg tactacctgc agaacggcag ggacatgtac   5760
gtggatcagg aactggacat caatcggctc tccgactacg acgtggatca tatcgtgccc   5820
cagtcttttc tcaaagatga ttctattgat aataaagtgt tgacaagatc cgataaaaat   5880
agagggaaga gtgataacgt cccctcagaa gaagttgtca gaaaatgaaa aaattattgg   5940
cggcagctgc tgaacgccaa actgatcaca caacggaagt tcgataatct gactaaggct   6000
gaacgaggtg gcctgtctga gttggataaa gccggcttca tcaaaaggca gcttgttgag   6060
acacgccaga tcaccaagca cgtggcccaa attctcgatt cacgcatgaa caccaagtac   6120
gatgaaaatg acaaactgat tcgagaggtg aaagttatta ctctgaagtc taagctggtc   6180
tcagatttca gaaaggactt tcagttttat aaggtgagag agatcaacaa ttaccaccat   6240
gcgcatgatg cctacctgaa tgcagtggta ggcactgcac ttatcaaaaa atatcccaag   6300
cttgaatctg aatttgttta cggagactat aaagtgtacg atgttaggaa atgatcgca   6360 aagtctgagc aggaaatagg caaggccacc gctaagtact tcttttacag caatattatg   6420
aattttttca gaccgagat tacactggcc aatggagaga ttcggaagcg accacttatc   6480
gaaacaaacg gagaaacagg agaaatcgtg tgggacaagg gtagggattt cgcgacagtc   6540
cggaaggtcc tgtccatgcc gcaggtgaac atcgttaaaa agaccgaagt acagaccgga   6600
ggcttctcca aggaaagtat cctcccgaaa aggaacagcg acaagctgat cgcacgcaaa   6660
aaagattggg accccaagaa atacggcgga ttcgattctc ctacagtcgc ttacagtgta   6720
ctggttgtgg ccaaagtgga gaagggaag tctaaaaaac tcaaaagcgt caaggaactg   6780
ctgggcatca caatcatgga gcgatcaagc ttcgaaaaaa accccatcga ctttctcgag   6840
gcgaaaggat ataagaggt caaaaaagac ctcatcatta agcttcccaa gtactctctc   6900
tttgagcttg aaaacggccg gaaacgaatg ctcgctagtg cgggcgagct gcagaaaggt   6960
aacgagctgg cactgccctc taaatacgtt aatttcttgt atctggccag ccactatgaa   7020
aagctcaaag ggtctcccga agataatgag cagaagcagt gttcgtgga acaacacaaa   7080 cactaccttg atgagatcat cgagcaaata agcgaattct ccaaaagagt gatcctcgcc   7140
gacgctaacc tcgataaggt gctttctgct tacaataagc acaggataa gcccatcagg   7200 gagcaggcag aaaacattat ccacttgtt actctgacca cttgggcgc gcctgcagcc   7260
```

-continued

```
ttcaagtact tcgacaccac catagacaga aagcggtaca cctctacaaa ggaggtcctg    7320
gacgccacac tgattcatca gtcaattacg gggctctatg aaacaagaat cgacctctct    7380
cagctcggtg gagacagcag ggctgacccc aagaagaaga ggaaggtggg tggaggaggt    7440 accccctagga ccgaaggcag gggaagcctt ctgacttgtg gggatgtgga agaaaaccct    7500
ggtccatcta gaatgattga acaagatgga ttgcacgcag gttctccggc cgcttgggtg    7560
gagaggctat tcggctatga ctgggcacaa cagacaatcg gctgctctga tgccgccgtg    7620
ttccggctgt cagcgcaggg gcgcccggtt cttttgtca agaccgacct gtccggtgcc    7680
ctgaatgaac tgcaggacga ggcagcgcgg ctatcgtggc tggccacgac gggcgttcct    7740
tgcgcagctg tgctcgacgt tgtcactgaa gcgggaaggg actggctgct attgggcgaa    7800
gtgccggggc aggatctcct gtcatctcac cttgctcctg ccgagaaagt atccatcatg    7860
gctgatgcaa tgcggcggct gcatacgctt gatccggcta cctgcccatt cgaccaccaa    7920
gcgaaacatc gcatcgagcg agcacgtact cggatggaag ccggtcttgt cgatcaggat    7980
gatctggacg aagagcatca ggggctcgcg ccagccgaac tgttcgccag gctcaaggcg    8040
cgcatgcccg acggcgagga tctcgtcgtg acccatggcg atgcctgctt gccgaatatc    8100
atggtggaaa atggccgctt ttctggattc atcgactgtg gccggctggg tgtggcggac    8160
cgctatcagg acatagcgtt ggctacccgt gatattgctg aagagcttgg cggcgaatgg    8220
gctgaccgct tcctcgtgct ttacggtatc gccgctcccg attcgcagcg catcgccttc    8280
tatcgccttc ttgacgagtt cttctgagcg ggactctggg gttcgaaatg accgaccaag    8340
cgacgcccaa cctgccatca cgagatttcg attccaccgc cgccttctat gaaaggttgg    8400
gcttcggaat cgttttccgg gacgccggct ggatgatcct ccagcgcggg gatctcatgc    8460
tggagttctt cgcccacccc aacttgttta ttgcagctta taatggttac aaataaagca    8520
atagcatcac aaatttcaca aataaagcat ttttttcact gcattctagt tgtggtttgt    8580
ccaaactcat caatgtatct tagc                                          8604
```

```
<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
attccagaat atctccatgt agattttggt                                      30

<210> SEQ ID NO 15
<211> LENGTH: 30
<212> TYPE: DNA
<213> ORGANISM: Artificial Sequence
<220> FEATURE:
<223> OTHER INFORMATION: Primer

<400> SEQUENCE: 15
aattccagga ggtccagatc ttcagggccc                                      30

<210> SEQ ID NO 16
<211> LENGTH: 59
<212> TYPE: DNA
<213> ORGANISM: Artificial Sequence
<220> FEATURE:
<223> OTHER INFORMATION: Primer

<400> SEQUENCE: 16
```

```
tctttcccta cacgacgctc ttccgatcta ttccagaata tctccatgta gattttggt      59
```

<210> SEQ ID NO 17
<211> LENGTH: 64
<212> TYPE: DNA
<213> ORGANISM: Artificial Sequence
<220> FEATURE:
<223> OTHER INFORMATION: Primer

<400> SEQUENCE: 17

```
gtgactggag ttcagacgtg tgctcttccg atctttaggc aaggaagtga ctgtaattat      60
gagc                                                                  64
```

<210> SEQ ID NO 18
<211> LENGTH: 26
<212> TYPE: DNA
<213> ORGANISM: Homo sapiens

<400> SEQUENCE: 18

```
acaatgcaga ctttgctttc cttggt                                          26
```

<210> SEQ ID NO 19
<211> LENGTH: 252
<212> TYPE: DNA
<213> ORGANISM: Artificial Sequence
<220> FEATURE:
<223> OTHER INFORMATION: Synthetic Sequence PBS2-derived Ugi CDS
      optimized for eucaryotic cell expression
<220> FEATURE:
<221> NAME/KEY: CDS
<222> LOCATION: (1)..(252)

<400> SEQUENCE: 19

```
atg acc aac ctt tcc gac atc ata gag aag gaa aca ggc aaa cag ttg       48
Met Thr Asn Leu Ser Asp Ile Ile Glu Lys Glu Thr Gly Lys Gln Leu
1               5                   10                  15 gtc atc caa gag tcg ata ctc atg ctt cct gaa gaa gtt gag gag gtc       96
Val Ile Gln Glu Ser Ile Leu Met Leu Pro Glu Glu Val Glu Glu Val
                20                  25                  30 att ggg aat aag ccg gaa agt gac att ctc gta cac act gcg tat gat      144
Ile Gly Asn Lys Pro Glu Ser Asp Ile Leu Val His Thr Ala Tyr Asp
            35                  40                  45 gag agc acc gat gag aac gtg atg ctg ctc acg tca gat gcc cca gag      192
Glu Ser Thr Asp Glu Asn Val Met Leu Leu Thr Ser Asp Ala Pro Glu
        50                  55                  60 tac aaa ccc tgg gct ctg gtg att cag gac tct aat gga gag aac aag      240
Tyr Lys Pro Trp Ala Leu Val Ile Gln Asp Ser Asn Gly Glu Asn Lys
65                  70                  75                  80 atc aag atg cta                                                      252
Ile Lys Met Leu
```

<210> SEQ ID NO 20
<211> LENGTH: 84
<212> TYPE: PRT
<213> ORGANISM: Artificial Sequence
<220> FEATURE:
<223> OTHER INFORMATION: Synthetic Construct

<400> SEQUENCE: 20

```
Met Thr Asn Leu Ser Asp Ile Ile Glu Lys Glu Thr Gly Lys Gln Leu
1               5                   10                  15

Val Ile Gln Glu Ser Ile Leu Met Leu Pro Glu Glu Val Glu Glu Val
                20                  25                  30
```

```
Ile Gly Asn Lys Pro Glu Ser Asp Ile Leu Val His Thr Ala Tyr Asp
             35                  40                  45

Glu Ser Thr Asp Glu Asn Val Met Leu Leu Thr Ser Asp Ala Pro Glu
 50                  55                  60

Tyr Lys Pro Trp Ala Leu Val Ile Gln Asp Ser Asn Gly Glu Asn Lys
 65                  70                  75                  80

Ile Lys Met Leu
```

```
<210> SEQ ID NO 21
<211> LENGTH: 420
<212> TYPE: DNA
<213> ORGANISM: Homo sapiens
<220> FEATURE:
<221> NAME/KEY: CDS
<222> LOCATION: (1)..(420)
<223> OTHER INFORMATION: fragment of TopBv2 (452-591)

<400> SEQUENCE: 21
```

```
aaa ggt att ccc aaa ctg gat gat gct aat gat gct ggt ggt aaa cat      48
Lys Gly Ile Pro Lys Leu Asp Asp Ala Asn Asp Ala Gly Gly Lys His
 1               5                  10                  15 tcc ctg gag tgt aca ctg ata tta aca gag gga gac tct gcc aaa tca      96
Ser Leu Glu Cys Thr Leu Ile Leu Thr Glu Gly Asp Ser Ala Lys Ser
             20                  25                  30 ctg gct gtg tct gga tta ggt gtg att gga cga gac aga tac gga gtt     144
Leu Ala Val Ser Gly Leu Gly Val Ile Gly Arg Asp Arg Tyr Gly Val
         35                  40                  45 ttt cca ctc agg ggc aaa att ctt aat gta cgg gaa gct tct cat aaa     192
Phe Pro Leu Arg Gly Lys Ile Leu Asn Val Arg Glu Ala Ser His Lys
     50                  55                  60 cag atc atg gaa aat gct gaa ata aat aat att att aaa ata gtt ggt     240
Gln Ile Met Glu Asn Ala Glu Ile Asn Asn Ile Ile Lys Ile Val Gly
 65                  70                  75                  80 cta caa tat aag aaa agt tac gat gat gca gaa tct ctg aaa acc tta     288
Leu Gln Tyr Lys Lys Ser Tyr Asp Asp Ala Glu Ser Leu Lys Thr Leu
                 85                  90                  95 cgc tat gga aag att atg att atg acc gat cag gat caa gat ggt tct     336
Arg Tyr Gly Lys Ile Met Ile Met Thr Asp Gln Asp Gln Asp Gly Ser
            100                 105                 110 cac ata aaa ggc ctg ctt att aat ttc atc cat cac aat tgg cca tca     384
His Ile Lys Gly Leu Leu Ile Asn Phe Ile His His Asn Trp Pro Ser
        115                 120                 125 ctt ttg aag cat ggt ttt ctt gaa gag ttc att act                     420
Leu Leu Lys His Gly Phe Leu Glu Glu Phe Ile Thr
    130                 135                 140
```

```
<210> SEQ ID NO 22
<211> LENGTH: 140
<212> TYPE: PRT
<213> ORGANISM: Homo sapiens

<400> SEQUENCE: 22
```

```
Lys Gly Ile Pro Lys Leu Asp Asp Ala Asn Asp Ala Gly Gly Lys His
 1               5                  10                  15

Ser Leu Glu Cys Thr Leu Ile Leu Thr Glu Gly Asp Ser Ala Lys Ser
             20                  25                  30

Leu Ala Val Ser Gly Leu Gly Val Ile Gly Arg Asp Arg Tyr Gly Val
         35                  40                  45

Phe Pro Leu Arg Gly Lys Ile Leu Asn Val Arg Glu Ala Ser His Lys
     50                  55                  60
```

```
Gln Ile Met Glu Asn Ala Glu Ile Asn Asn Ile Ile Lys Ile Val Gly
 65                  70                  75                  80

Leu Gln Tyr Lys Lys Ser Tyr Asp Asp Ala Glu Ser Leu Lys Thr Leu
             85                  90                  95

Arg Tyr Gly Lys Ile Met Ile Met Thr Asp Gln Asp Gln Asp Gly Ser
            100                 105                 110

His Ile Lys Gly Leu Leu Ile Asn Phe Ile His His Asn Trp Pro Ser
        115                 120                 125

Leu Leu Lys His Gly Phe Leu Glu Glu Phe Ile Thr
        130                 135                 140
```

<210> SEQ ID NO 23  
<211> LENGTH: 246  
<212> TYPE: DNA  
<213> ORGANISM: Homo sapiens  
<220> FEATURE:  
<221> NAME/KEY: CDS  
<222> LOCATION: (1)..(246)  
<223> OTHER INFORMATION: fragment of IQGAP2 (466-547)

<400> SEQUENCE: 23

```
gaa ggg aat cct ttg agg act tta gaa act ttg ctc cta cct act gcg    48
Glu Gly Asn Pro Leu Arg Thr Leu Glu Thr Leu Leu Leu Pro Thr Ala
 1               5                  10                  15 aat att agt gat gtg gac cca gcc cat gcc cag cac tac cag gat gtt    96
Asn Ile Ser Asp Val Asp Pro Ala His Ala Gln His Tyr Gln Asp Val
             20                  25                  30 tta tac cat gct aaa tca cag aaa ctc gga gac tct gag agt gtt tcc   144
Leu Tyr His Ala Lys Ser Gln Lys Leu Gly Asp Ser Glu Ser Val Ser
         35                  40                  45 aaa gtg ctt tgg ctg gat gag ata cag caa gcc gtc gat gat gcc aac   192
Lys Val Leu Trp Leu Asp Glu Ile Gln Gln Ala Val Asp Asp Ala Asn
 50                  55                  60 gtg gac aag gac aga gca aaa caa tgg gtt act ctg gtg gtt gat gtt   240
Val Asp Lys Asp Arg Ala Lys Gln Trp Val Thr Leu Val Val Asp Val
 65                  70                  75                  80 aat cag                                                            246
Asn Gln
```

<210> SEQ ID NO 24  
<211> LENGTH: 82  
<212> TYPE: PRT  
<213> ORGANISM: Homo sapiens

<400> SEQUENCE: 24

```
Glu Gly Asn Pro Leu Arg Thr Leu Glu Thr Leu Leu Leu Pro Thr Ala
 1               5                  10                  15

Asn Ile Ser Asp Val Asp Pro Ala His Ala Gln His Tyr Gln Asp Val
             20                  25                  30

Leu Tyr His Ala Lys Ser Gln Lys Leu Gly Asp Ser Glu Ser Val Ser
         35                  40                  45

Lys Val Leu Trp Leu Asp Glu Ile Gln Gln Ala Val Asp Asp Ala Asn
 50                  55                  60

Val Asp Lys Asp Arg Ala Lys Gln Trp Val Thr Leu Val Val Asp Val
 65                  70                  75                  80

Asn Gln
```

<210> SEQ ID NO 25  
<211> LENGTH: 447  
<212> TYPE: DNA  
<213> ORGANISM: Homo sapiens

```
<220> FEATURE:
<221> NAME/KEY: CDS
<222> LOCATION: (1)..(447)
<223> OTHER INFORMATION: fragment of NIF-ZFN335_745-893 (466-547)

<400> SEQUENCE: 25 agt tcc cca gga cct cct gag ata ccc cca gag gcg aca act ttc cag      48
Ser Ser Pro Gly Pro Pro Glu Ile Pro Pro Glu Ala Thr Thr Phe Gln
1               5                   10                  15 tca tct gag gct ccc tca ttg ctc tgt tct gac acc ctg ggc ggc gcc      96
Ser Ser Glu Ala Pro Ser Leu Leu Cys Ser Asp Thr Leu Gly Gly Ala
            20                  25                  30 acc atc atc tac cag caa gga gct gag gag tcg aca gcg atg gcc acg     144
Thr Ile Ile Tyr Gln Gln Gly Ala Glu Glu Ser Thr Ala Met Ala Thr
        35                  40                  45 cag aca gcc ttg gat ctt ctg ctg aac atg agt gct cag cgg gaa ctg     192
Gln Thr Ala Leu Asp Leu Leu Leu Asn Met Ser Ala Gln Arg Glu Leu
    50                  55                  60 ggg ggc aca gcc ctg cag gtg gct gtg gtg aag tcg gaa gat gtg gaa     240
Gly Gly Thr Ala Leu Gln Val Ala Val Val Lys Ser Glu Asp Val Glu
65                  70                  75                  80 gca ggg tta gca tcc cct ggt ggg cag ccc tcc cct gaa ggt gcc act     288
Ala Gly Leu Ala Ser Pro Gly Gly Gln Pro Ser Pro Glu Gly Ala Thr
                85                  90                  95 cca cag gtc gtc acc ctc cac gtg gca gag cca ggg ggc ggt gca gca     336
Pro Gln Val Val Thr Leu His Val Ala Glu Pro Gly Gly Gly Ala Ala
            100                 105                 110 gcc gag agc cag cta ggc cct cct gac cta ccg cag atc acc ctg gca     384
Ala Glu Ser Gln Leu Gly Pro Pro Asp Leu Pro Gln Ile Thr Leu Ala
        115                 120                 125 cct ggt cca ttt ggt ggg act ggc tac agt gtc atc aca gca ccc cct     432
Pro Gly Pro Phe Gly Gly Thr Gly Tyr Ser Val Ile Thr Ala Pro Pro
    130                 135                 140 atg gag gag gga aca                                                  447
Met Glu Glu Gly Thr
145

<210> SEQ ID NO 26
<211> LENGTH: 149
<212> TYPE: PRT
<213> ORGANISM: Homo sapiens

<400> SEQUENCE: 26

Ser Ser Pro Gly Pro Pro Glu Ile Pro Pro Glu Ala Thr Thr Phe Gln
1               5                   10                  15

Ser Ser Glu Ala Pro Ser Leu Leu Cys Ser Asp Thr Leu Gly Gly Ala
            20                  25                  30

Thr Ile Ile Tyr Gln Gln Gly Ala Glu Glu Ser Thr Ala Met Ala Thr
        35                  40                  45

Gln Thr Ala Leu Asp Leu Leu Leu Asn Met Ser Ala Gln Arg Glu Leu
    50                  55                  60

Gly Gly Thr Ala Leu Gln Val Ala Val Val Lys Ser Glu Asp Val Glu
65                  70                  75                  80

Ala Gly Leu Ala Ser Pro Gly Gly Gln Pro Ser Pro Glu Gly Ala Thr
                85                  90                  95

Pro Gln Val Val Thr Leu His Val Ala Glu Pro Gly Gly Gly Ala Ala
            100                 105                 110

Ala Glu Ser Gln Leu Gly Pro Pro Asp Leu Pro Gln Ile Thr Leu Ala
        115                 120                 125
```

```
Pro Gly Pro Phe Gly Gly Thr Gly Tyr Ser Val Ile Thr Ala Pro Pro
    130                 135                 140

Met Glu Glu Gly Thr
145

<210> SEQ ID NO 27
<211> LENGTH: 20
<212> TYPE: DNA
<213> ORGANISM: Homo sapiens

<400> SEQUENCE: 27
tcgagatgtg atgaaggaga                                              20

<210> SEQ ID NO 28
<211> LENGTH: 9228
<212> TYPE: DNA
<213> ORGANISM: Artificial Sequence
<220> FEATURE:
<223> OTHER INFORMATION: Synthetic Sequence Complete nucleotide
      sequence of vector 1923-2
<220> FEATURE:
<221> NAME/KEY: misc_feature
<222> LOCATION: (167)..(188)
<223> OTHER INFORMATION: CAP binding site
<220> FEATURE:
<221> NAME/KEY: rep_origin
<222> LOCATION: (476)..(1064)
<223> OTHER INFORMATION: ori
<220> FEATURE:
<221> NAME/KEY: gene
<222> LOCATION: (1235)..(2095)
<223> OTHER INFORMATION: AmpR
<220> FEATURE:
<221> NAME/KEY: promoter
<222> LOCATION: (2096)..(2200)
<223> OTHER INFORMATION: AmpR promoter
<220> FEATURE:
<221> NAME/KEY: promoter
<222> LOCATION: (2233)..(2461)
<223> OTHER INFORMATION: H1 promoter
<220> FEATURE:
<221> NAME/KEY: misc_feature
<222> LOCATION: (2462)..(2481)
<223> OTHER INFORMATION: Target (HPRT site 1)
<220> FEATURE:
<221> NAME/KEY: misc_structure
<222> LOCATION: (2482)..(2557)
<223> OTHER INFORMATION: tracrRNA
<220> FEATURE:
<221> NAME/KEY: enhancer
<222> LOCATION: (2572)..(2951)
<223> OTHER INFORMATION: CMV enhancer
<220> FEATURE:
<221> NAME/KEY: promoter
<222> LOCATION: (2952)..(3155)
<223> OTHER INFORMATION: CMV promoter
<220> FEATURE:
<221> NAME/KEY: promoter
<222> LOCATION: (3200)..(3218)
<223> OTHER INFORMATION: T7 promoter
<220> FEATURE:
<221> NAME/KEY: gene
<222> LOCATION: (3247)..(3498)
<223> OTHER INFORMATION: UGI
<220> FEATURE:
<221> NAME/KEY: misc_feature
<222> LOCATION: (3502)..(3504)
<223> OTHER INFORMATION: kozac
<220> FEATURE:
<221> NAME/KEY: misc_feature
<222> LOCATION: (3505)..(3555)
<223> OTHER INFORMATION: NLS unit
<220> FEATURE:
<221> NAME/KEY: misc_feature
<222> LOCATION: (3511)..(3531)
```

```
<223> OTHER INFORMATION: SV40 NLS
<220> FEATURE:
<221> NAME/KEY: gene
<222> LOCATION: (3556)..(7692)
<223> OTHER INFORMATION: nCas9 (D10A)
<220> FEATURE:
<221> NAME/KEY: misc_feature
<222> LOCATION: (7672)..(7692)
<223> OTHER INFORMATION: SV40 NLS
<220> FEATURE:
<221> NAME/KEY: gene
<222> LOCATION: (7714)..(8262)
<223> OTHER INFORMATION: dVif
<220> FEATURE:
<221> NAME/KEY: misc_feature
<222> LOCATION: (7714)..(7722)
<223> OTHER INFORMATION: CBF beta binding
<220> FEATURE:
<221> NAME/KEY: misc_feature
<222> LOCATION: (8272)..(8325)
<223> OTHER INFORMATION: T2A
<220> FEATURE:
<221> NAME/KEY: gene
<222> LOCATION: (8332)..(8931)
<223> OTHER INFORMATION: PuroR
<220> FEATURE:
<221> NAME/KEY: polyA_signal
<222> LOCATION: (9105)..(9226)
<223> OTHER INFORMATION: SV40 poly(A) signal

<400> SEQUENCE: 28
ggccgccacc gcggtggagc tccagctttt gttcccttta gtgagggtta attgcgcgct      60
tggcgtaatc atggtcatag ctgtttcctg tgtgaaattg ttatccgctc acaattccac     120
acaacatacg agccggaagc ataaagtgta aagcctgggg tgcctaatga gtgagctaac     180
tcacattaat tgcgttgcgc tcactgcccg ctttccagtc gggaaacctg tcgtgccagc     240
tgcattaatg aatcggccaa cgcgcgggga gaggcggttt gcgtattggg cgctcttccg     300
cttcctcgct cactgactcg ctgcgctcgg tcgttcggct gcggcgagcg gtatcagctc     360
actcaaaggc ggtaatacgg ttatccacag aatcagggga taacgcagga aagaacatgt     420
gagcaaaagg ccagcaaaag gccaggaacc gtaaaaaggc cgcgttgctg gcgtttttcc     480
ataggctccg ccccccctgac gagcatcaca aaaatcgacg ctcaagtcag aggtggcgaa     540
acccgacagg actataaaga taccaggcgt ttccccctgg aagctccctc gtgcgctctc     600
ctgttccgac cctgccgctt accggatacc tgtccgcctt ctcccttcg ggaagcgtgg      660 cgctttctca tagctcacgc tgtaggtatc tcagttcggt gtaggtcgtt cgctccaagc     720
tgggctgtgt gcacgaaccc cccgttcagc ccgaccgctg cgccttatcc ggtaactatc     780
gtcttgagtc aacccggta agacacgact tatcgccact ggcagcagcc actggtaaca     840
ggattagcag agcgaggtat gtaggcggtg ctacagagtt cttgaagtgg tggcctaact     900
acggctacac tagaaggaca gtatttggta tctgcgctct gctgaagcca gttaccttcg     960
gaaaaagagt tggtagctct tgatccggca aacaaaccac cgctggtagc ggtggttttt    1020
ttgtttgcaa gcagcagatt acgcgcagaa aaaaaggatc tcaagaagat cctttgatct    1080
tttctacggg gtctgacgct cagtggaacg aaaactcacg ttaagggatt ttggtcatga    1140
gattatcaaa aaggatcttc acctagatcc ttttaaatta aaaatgaagt tttaaatcaa    1200
tctaaagtat atatgagtaa acttggtctg acagttacca atgcttaatc agtgaggcac    1260
ctatctcagc gatctgtcta tttcgttcat ccatagttgc ctgactcccc gtcgtgtaga    1320
taactacgat acgggagggc ttaccatctg gccccagtgc tgcaatgata ccgcgagacc    1380
cacgctcacc ggctccagat ttatcagcaa taaaccagcc agccggaagg gccgagcgca    1440
```

```
gaagtggtcc tgcaacttta tccgcctcca tccagtctat taattgttgc cgggaagcta   1500
gagtaagtag ttcgccagtt aatagtttgc gcaacgttgt tgccattgct acaggcatcg   1560
tggtgtcacg ctcgtcgttt ggtatggctt cattcagctc cggttcccaa cgatcaaggc   1620
gagttacatg atccccatg ttgtgcaaaa agcggttag ctccttcggt cctccgatcg    1680
ttgtcagaag taagttggcc gcagtgttat cactcatggt tatggcagca ctgcataatt   1740
ctcttactgt catgccatcc gtaagatgct tttctgtgac tggtgagtac tcaaccaagt   1800
cattctgaga atagtgtatg cggcgaccga gttgctcttg cccggcgtca atacgggata   1860
ataccgcgcc acatagcaga actttaaaag tgctcatcat tggaaaacgt tcttcggggc   1920
gaaaactctc aaggatctta ccgctgttga gatccagttc gatgtaaccc actcgtgcac   1980
ccaactgatc ttcagcatct tttactttca ccagcgtttc tgggtgagca aaaacaggaa   2040
ggcaaaatgc cgcaaaaaag gaataaggg cgacacggaa atgttgaata ctcatactct   2100
tcctttttca atattattga agcatttatc agggttattg tctcatgagc ggatacatat   2160
ttgaatgtat ttagaaaaat aaacaaatag gggttccgcg cacatttccc cgaaaagtgc   2220
caccggtgta ccaattcgaa cgctgacgtc atcaacccgc tccaaggaat cgcgggccca   2280
gtgtcactag gcgggaacac ccagcgcgcg tgcgccctgg caggaagatg gctgtgaggg   2340
acaggggagt ggcgccctgc aatatttgca tgtcgctatg tgttctggga atcaccata    2400 aacgtgaaat gtctttggat ttgggaatct tataagttct gtatgaggac cacagatccc   2460
ctcgagatgt gatgaaggag agttttagag ctagaaatag caagtttaaaa taaggctagt  2520 ccgttatcaa cttgaaaaag tggcaccgag tcggtgcttt ttttacgcgt tgacattgat   2580
tattgactag ttattaatag taatcaatta cggggtcatt agttcatagc ccatatatgg   2640
agttccgcgt tacataactt acggtaaatg gcccgcctgg ctgaccgccc aacgaccccc   2700
gcccattgac gtcaataatg acgtatgttc ccatagtaac gccaataggg actttccatt   2760
gacgtcaatg ggtggagtat ttacggtaaa ctgcccactt ggcagtacat caagtgtatc   2820
atatgccaag tacgcccccct attgacgtca atgacggtaa atggcccgcc tggcattatg   2880
cccagtacat gaccttatgg gactttccta cttggcagta catctacgta ttagtcatcg   2940
ctattaccat ggtgatgcgg ttttggcagt acatcaatgg gcgtggatag cggtttgact   3000
cacggggatt tccaagtctc cacccccattg acgtcaatgg gagtttgttt tggcaccaaa   3060
atcaacggga ctttccaaaa tgtcgtaaca actccgcccc attgacgcaa atgggcggta   3120
ggcgtgtacg gtgggaggtc tatataagca gagctctctg gctaactaga gaacccactg   3180
cttactggct tatcgaaatt aatacgactc actataggga gacccaagct ggctaggggt   3240
accgaaatga ccaacctttc cgacatcata gagaaggaaa caggcaaaca gttggtcatc   3300
caagagtcga tactcatgct tcctgaagaa gttgaggagg tcattgggaa taagccggaa   3360
agtgacattc tcgtacacac tgcgtatgat gagagcaccg atgagaacgt gatgctgctc   3420
acgtcagatg ccccagagta caaaccctgg gctctggtga ttcaggactc taatggagag   3480
aacaagatca agatgctagc cgaaatggca ccgaagaaga agcgtaaagt cggaatccac   3540
ggagttcctg cggcaatgga caagaagtac tccattgggc tcgctatcgg cacaaacagc   3600
gtcggttggg ccgtcattac ggacgagtac aaggtgccga gcaaaaaatt caaagttctg   3660
ggcaataccg atcgccacag cataaagaag aacctcattg cgccctcct gttcgactcc   3720 ggggagacgg ccgaagccac gcggctcaaa agaacagcac ggcgcagata tacccgcaga   3780
```

```
aagaatcgga tctgctacct gcaggagatc tttagtaatg agatggctaa ggtggatgac    3840
tctttcttcc ataggctgga ggagtccttt ttggtggagg aggataaaaa gcacgagcgc    3900
cacccaatct ttggcaatat cgtggacgag gtggcgtacc atgaaaagta cccaaccata    3960
tatcatctga ggaagaagct tgtagacagt actgataagg ctgacttgcg gttgatctat    4020
ctcgcgctgg cgcatatgat caaatttcgg ggacacttcc tcatcgaggg ggacctgaac    4080
ccagacaaca gcgatgtcga caaactcttt atccaactgg ttcagactta caatcagctt    4140
ttcgaagaga acccgatcaa cgcatccgga gttgacgcca aagcaatcct gagcgctagg    4200
ctgtccaaat cccggcggct cgaaaacctc atcgcacagc tccctgggga agaagaac     4260 ggcctgtttg gtaatcttat cgccctgtca ctcgggctga cccccaactt taaatctaac    4320
ttcgacctgg ccgaagatgc caagcttcaa ctgagcaaag acacctacga tgatgatctc    4380
gacaatctgc tggcccagat cggcgaccag tacgcagacc ttttttttggc ggcaaagaac    4440 ctgtcagacg ccattctgct gagtgatatt ctgcgagtga acacggagat caccaaagct    4500
ccgctgagcg ctagtatgat caagcgctat gatgagcacc accaagactt gactttgctg    4560
aaggcccttg tcagacagca actgcctgag aagtacaagg aaattttctt cgatcagtct    4620
aaaaatggct acgccggata cattgacggc ggagcaagcc aggaggaatt ttacaaattt    4680
attaagccca tcttggaaaa aatggacggc accgaggagc tgctggtaaa gcttaacaga    4740
gaagatctgt tgcgcaaaca gcgcactttc gacaatggaa gcatccccca ccagattcac    4800
ctgggcgaac tgcacgctat cctcaggcgg caagaggatt tctacccctt tttgaaagat    4860
aacagggaaa agattgagaa aatcctcaca tttcggatac cctactatgt aggcccctc    4920 gcccggggaa attccagatt cgcgtggatg actcgcaaat cagaagagac catcactccc    4980
tggaacttcg aggaagtcgt ggataagggg gcctctgccc agtccttcat cgaaaggatg    5040
actaactttg ataaaaatct gcctaacgaa aaggtgcttc ctaaacactc tctgctgtac    5100
gagtacttca cagtttataa cgagctcacc aaggtcaaat acgtcacaga agggatgaga    5160
aagccagcat tcctgtctgg agagcagaag aaagctatcg tggacctcct cttcaagacg    5220
aaccggaaag ttaccgtgaa acagctcaaa gaagactatt tcaaaaagat tgaatgtttc    5280
gactctgttg aaatcagcgg agtggaggat cgcttcaacg catccctggg aacgtatcac    5340
gatctcctga aaatcattaa agacaaggac ttcctggaca atgaggagaa cgaggacatt    5400
cttgaggaca ttgtcctcac ccttacgttg tttgaagata gggagatgat tgaagaacgc    5460
ttgaaaactt acgctcatct cttcgacgac aaagtcatga acagctcaa gaggcgccga   5520 tatacaggat gggggcggct gtcaagaaaa ctgatcaatg ggatccgaga caagcagagt    5580
ggaaagacaa tcctggattt tcttaagtcc gatggatttg ccaaccggaa cttcatgcag    5640
ttgatccatg atgactctct cacctttaag gaggacatcc agaaagcaca gtttctggc    5700 caggggggaca gtcttcacga gcacatcgct aatcttgcag gtagcccagc tatcaaaaag    5760
ggaatactgc agaccgttaa ggtcgtggat gaactcgtca agtaatggg aaggcataag    5820 cccgagaata tcgttatcga gatggcccga gagaaccaaa ctacccagaa gggacagaag    5880
aacagtaggg aaaggatgaa gaggattgaa gagggtataa agaactggg gtcccaaatc    5940 cttaaggaac acccagttga aaacacccag cttcagaatg agaagctcta cctgtactac    6000
ctgcagaacg gcagggacat gtacgtggat caggaactgg acatcaatcg gctctccgac    6060
tacgacgtgg atcatatcgt gccccagtct tttctcaaag atgattctat tgataataaa    6120
gtgttgacaa gatccgataa aaatagaggg aagagtgata acgtcccctc agaagaagtt    6180
```

```
gtcaagaaaa tgaaaaatta ttggcggcag ctgctgaacg ccaaactgat cacacaacgg    6240
aagttcgata atctgactaa ggctgaacga ggtggcctgt ctgagttgga taaagccggc    6300
ttcatcaaaa ggcagcttgt tgagacacgc cagatcacca agcacgtggc ccaaattctc    6360
gattcacgca tgaacaccaa gtacgatgaa atgacaaac tgattcgaga ggtgaaagtt     6420
attactctga agtctaagct ggtctcagat ttcagaaagg actttcagtt ttataaggtg    6480
agagagatca acaattacca ccatgcgcat gatgcctacc tgaatgcagt ggtaggcact    6540
gcacttatca aaaatatcc caagcttgaa tctgaatttg tttacggaga ctataaagtg     6600
tacgatgtta ggaaaatgat cgcaaagtct gagcaggaaa taggcaaggc caccgctaag    6660
tacttctttt acagcaatat tatgaatttt ttcaagaccg agattacact ggccaatgga    6720
gagattcgga agcgaccact tatcgaaaca acggagaaaa caggagaaat cgtgtgggac    6780
aagggtaggg atttcgcgac agtccggaag gtcctgtcca tgccgcaggt gaacatcgtt    6840
aaaaagaccg aagtacagac cggaggcttc tccaaggaaa gtatcctccc gaaaaggaac    6900
agcgacaagc tgatcgcacg caaaaaagat tgggaccca agaaatacgg cggattcgat     6960
tctcctacag tcgcttacag tgtactggtt gtggccaaag tggagaaagg gaagtctaaa    7020
aaactcaaaa gcgtcaagga actgctgggc atcacaatca tggagcgatc aagcttcgaa    7080
aaaaccccca tcgactttct cgaggcgaaa ggatataaag aggtcaaaaa agacctcatc    7140
attaagcttc ccaagtactc tctctttgag cttgaaaacg gccggaaacg aatgctcgct    7200
agtgcgggcg agctgcagaa aggtaacgag ctggcactgc cctctaaata cgttaatttc    7260
ttgtatctgg ccagccacta tgaaaagctc aaagggtctc ccgaagataa tgagcagaag    7320
cagctgttcg tggaacaaca caaacactac cttgatgaga tcatcgagca aataagcgaa    7380
ttctccaaaa gagtgatcct cgccgacgct aacctcgata aggtgctttc tgcttacaat    7440
aagcacaggg ataagcccat cagggagcag gcagaaaaca ttatccactt gtttactctg    7500
accaacttgg gcgcgcctgc agccttcaag tacttcgaca ccaccataga cagaaagcgg    7560
tacacctcta caaaggaggt cctggacgcc acactgattc atcagtcaat tacgggctc     7620 tatgaaacaa gaatcgacct ctctcagctc ggtggagaca gcagggctga ccccaagaag    7680
aagaggaagg tgggtggagg aggtaccgaa atggtgtggc aagtagacag gatgaggatt    7740
agaacatgga acagtttagt aaaacatcac atgtatatct caaagaaagc aaaaaattgg    7800
ttttatagac atcactttga aagcagtcat ccaagagtaa gttcagaagt acacatccca    7860
ctaggggatg ctagattagt agtaagaaca tattggggtc tgcatacagg agaaaaagat    7920
tggcacttgg gtaatggggt gtccatagaa tggagactaa aagatatag cacacaaata     7980 gatcctgacc tggcagacca actaattcat ctgcattatt ttaattgttt ttcagactct    8040
gccataagga aagccatatt aggacaagta gttagaccta gatgtgacta tcaagcagga    8100
cataacaagg taggatctgc tcaatatttg gcactgaaag cattagtaac accagtaagg    8160
acaaggccac ctttgcctag tgttaggaaa ttagcagagg acagatggaa caagccccag    8220
aaaaccaggg gtcccagagg gagccataca atgaatggac atgctaggac cgaaggcagg    8280
ggaagccttc tgacttgtgg ggatgtgaa gaaaaccctg gtccatctag aatgaccgag      8340
tacaagccca cggtgcgcct cgccacccgc gacgacgtcc ccgggccgt acgcaccctc      8400 gccgccgcgt tcgccgacta ccccgccacg gccacaccg tcgacccgga ccgccacatc      8460
gagcgggtca ccgagctgca agaactcttc ctcacgcgcg tcgggctcga catcggcaag    8520
```

-continued

```
gtgtgggtcg cggacgacgg cgccgcggtg gcggtctgga ccacgccgga gagcgtcgaa    8580 gcggggggcgg tgttcgccga gatcggcccg cgcatggccg agttgagcgg ttcccggctg   8640
gccgcgcagc aacagatgga aggcctcctg gcgccgcacc ggcccaagga gcccgcgtgg   8700
ttcctggcca ccgtcggcgt ctcgcccgac caccagggca agggtctggg cagcgccgtc   8760
gtgctccccg gagtggaggc ggccgagcgc gccggggtgc ccgccttcct ggagacctcc   8820
gcgccccgca acctcccctt ctacgagcgg ctcggcttca ccgtcaccgc cgacgtcgag   8880
gtgcccgaag gaccgcgcac ctggtgcatg acccgcaagc ccggtgcctg agcgggactc   8940
tggggttcga aatgaccgac caagcgacgc ccaacctgcc atcacgagat ttcgattcca   9000
ccgccgcctt ctatgaaagg ttgggcttcg gaatcgtttt ccgggacgcc ggctggatga   9060
tcctccagcg cggggatctc atgctggagt tcttcgccca ccccaacttg tttattgcag   9120
cttataatgg ttacaaataa agcaatagca tcacaaattt cacaaataaa gcatttttt    9180 cactgcattc tagttgtggt ttgtccaaac tcatcaatgt atcttagc                9228
```

<210> SEQ ID NO 29
<211> LENGTH: 9198
<212> TYPE: DNA
<213> ORGANISM: Artificial Sequence
<220> FEATURE:
<223> OTHER INFORMATION: Synthetic Sequence Complete nucleotide
      sequence of vector 1924-2
<220> FEATURE:
<221> NAME/KEY: rep_origin
<222> LOCATION: (476)..(1064)
<223> OTHER INFORMATION: ori
<220> FEATURE:
<221> NAME/KEY: gene
<222> LOCATION: (1235)..(2095)
<223> OTHER INFORMATION: AmpR
<220> FEATURE:
<221> NAME/KEY: promoter
<222> LOCATION: (2096)..(2200)
<223> OTHER INFORMATION: AmpR promoter
<220> FEATURE:
<221> NAME/KEY: promoter
<222> LOCATION: (2233)..(2461)
<223> OTHER INFORMATION: H1 promoter
<220> FEATURE:
<221> NAME/KEY: gene
<222> LOCATION: (2462)..(2481)
<223> OTHER INFORMATION: HPRT exon
<220> FEATURE:
<221> NAME/KEY: misc_feature
<222> LOCATION: (2462)..(2481)
<223> OTHER INFORMATION: Target (HPRT site 1)
<220> FEATURE:
<221> NAME/KEY: misc_structure
<222> LOCATION: (2482)..(2557)
<223> OTHER INFORMATION: tracrRNA
<220> FEATURE:
<221> NAME/KEY: enhancer
<222> LOCATION: (2572)..(2951)
<223> OTHER INFORMATION: CMV enhancer
<220> FEATURE:
<221> NAME/KEY: promoter
<222> LOCATION: (2952)..(3155)
<223> OTHER INFORMATION: CMV promoter
<220> FEATURE:
<221> NAME/KEY: promoter
<222> LOCATION: (3200)..(3218)
<223> OTHER INFORMATION: T7 promoter
<220> FEATURE:
<221> NAME/KEY: gene
<222> LOCATION: (3250)..(3798)
<223> OTHER INFORMATION: dVif
<220> FEATURE:
<221> NAME/KEY: misc_feature
<222> LOCATION: (3250)..(3258)

```
<223> OTHER INFORMATION: CBF beta binding
<220> FEATURE:
<221> NAME/KEY: misc_feature
<222> LOCATION: (3805)..(3807)
<223> OTHER INFORMATION: kozac
<220> FEATURE:
<221> NAME/KEY: misc_feature
<222> LOCATION: (3808)..(3858)
<223> OTHER INFORMATION: NLS unit
<220> FEATURE:
<221> NAME/KEY: misc_feature
<222> LOCATION: (3814)..(3834)
<223> OTHER INFORMATION: SV40 NLS
<220> FEATURE:
<221> NAME/KEY: gene
<222> LOCATION: (3859)..(7962)
<223> OTHER INFORMATION: nCas9 (D10A)
<220> FEATURE:
<221> NAME/KEY: misc_feature
<222> LOCATION: (7963)..(7983)
<223> OTHER INFORMATION: SV40 NLS
<220> FEATURE:
<221> NAME/KEY: gene
<222> LOCATION: (7990)..(8241)
<223> OTHER INFORMATION: UGI
<220> FEATURE:
<221> NAME/KEY: misc_feature
<222> LOCATION: (8242)..(8295)
<223> OTHER INFORMATION: T2A
<220> FEATURE:
<221> NAME/KEY: gene
<222> LOCATION: (8302)..(8901)
<223> OTHER INFORMATION: PuroR
<220> FEATURE:
<221> NAME/KEY: polyA_signal
<222> LOCATION: (9075)..(9196)
<223> OTHER INFORMATION: SV40 poly(A) signal

<400> SEQUENCE: 29
ggccgccacc gcggtggagc tccagctttt gttcccttta gtgagggtta attgcgcgct      60
tggcgtaatc atggtcatag ctgtttcctg tgtgaaattg ttatccgctc acaattccac     120
acaacatacg agccggaagc ataaagtgta aagcctgggg tgcctaatga gtgagctaac     180
tcacattaat tgcgttgcgc tcactgcccg ctttccagtc gggaaacctg tcgtgccagc     240
tgcattaatg aatcggccaa cgcgcgggga gaggcggttt gcgtattggg cgctcttccg     300
cttcctcgct cactgactcg ctgcgctcgg tcgttcggct gcggcgagcg gtatcagctc     360
actcaaaggc ggtaatacgg ttatccacag aatcagggga taacgcagga agaacatgt     420 gagcaaaagg ccagcaaaag gccaggaacc gtaaaaaggc cgcgttgctg gcgttttcc     480 ataggctccg ccccccctgac gagcatcaca aaaatcgacg ctcaagtcag aggtggcgaa     540
acccgacagg actataaaga taccaggcgt ttccccctgg aagctccctc gtgcgctctc     600
ctgttccgac cctgccgctt accggatacc tgtccgcctt tctcccttcg ggaagcgtgg     660
cgctttctca tagctcacgc tgtaggtatc tcagttcggt gtaggtcgtt cgctccaagc     720
tgggctgtgt gcacgaaccc cccgttcagc ccgaccgctg cgccttatcc ggtaactatc     780
gtcttgagtc caacccggta agacacgact tatcgccact ggcagcagcc actggtaaca     840
ggattagcag agcgaggtat gtaggcggtg ctacagagtt cttgaagtgg tggcctaact     900
acggctacac tagaaggaca gtatttggta tctgcgctct gctgaagcca gttaccttcg     960
gaaaaagagt tggtagctct tgatccggca acaaaccac cgctggtagc ggtggttttt    1020
ttgtttgcaa gcagcagatt acgcgcagaa aaaaggatc tcaagaagat cctttgatct    1080
tttctacggg gtctgacgct cagtggaacg aaaactcacg ttagggatt ttggtcatga    1140 gattatcaaa aaggatcttc acctagatcc ttttaaatta aaaatgaagt tttaaatcaa    1200
```

```
tctaaagtat atatgagtaa acttggtctg acagttacca atgcttaatc agtgaggcac    1260
ctatctcagc gatctgtcta tttcgttcat ccatagttgc ctgactcccc gtcgtgtaga    1320
taactacgat acgggagggc ttaccatctg gccccagtgc tgcaatgata ccgcgagacc    1380
cacgctcacc ggctccagat ttatcagcaa taaaccagcc agccggaagg gccgagcgca    1440
gaagtggtcc tgcaacttta tccgcctcca tccagtctat taattgttgc cgggaagcta    1500
gagtaagtag ttcgccagtt aatagtttgc gcaacgttgt tgccattgct acaggcatcg    1560
tggtgtcacg ctcgtcgttt ggtatggctt cattcagctc cggttcccaa cgatcaaggc    1620
gagttacatg atcccccatg ttgtgcaaaa aagcggttag ctccttcggt cctccgatcg    1680
ttgtcagaag taagttggcc gcagtgttat cactcatggt tatggcagca ctgcataatt    1740
ctcttactgt catgccatcc gtaagatgct tttctgtgac tggtgagtac tcaaccaagt    1800
cattctgaga atagtgtatg cggcgaccga gttgctcttg cccggcgtca atacgggata    1860
ataccgcgcc acatagcaga actttaaaag tgctcatcat tggaaaacgt tcttcggggc    1920
gaaaactctc aaggatctta ccgctgttga tccagttc gatgtaaccc actcgtgcac    1980
ccaactgatc ttcagcatct tttactttca ccagcgtttc tgggtgagca aaaacaggaa    2040
ggcaaaatgc cgcaaaaaag gaataagggg cgacacggaa atgttgaata ctcatactct    2100
tcctttttca atattattga agcatttatc agggttattg tctcatgagc ggatacatat    2160
ttgaatgtat ttagaaaaat aaacaaatag gggttccgcg cacatttccc cgaaaagtgc    2220
caccggtgta ccaattcgaa cgctgacgtc atcaacccgc tccaaggaat cgcgggccca    2280
gtgtcactag gcgggaacac ccagcgcgcg tgcgccctgg caggaagatg gctgtgaggg    2340
acaggggagt ggcgccctgc aatatttgca tgtcgctatg tgttctggga atcaccata    2400 aacgtgaaat gtctttggat ttgggaatct tataagttct gtatgaggac cacagatccc    2460
ctcgagatgt gatgaaggag agttttagag ctagaaatag caagttaaaa taaggctagt    2520
ccgttatcaa cttgaaaaag tggcaccgag tcggtgcttt ttttacgcgt tgacattgat    2580
tattgactag ttattaatag taatcaatta cggggtcatt agttcatagc ccatatatgg    2640
agttccgcgt tacataactt acggtaaatg gcccgcctgg ctgaccgccc aacgacccc    2700 gcccattgac gtcaataatg acgtatgttc ccatagtaac gccaataggg actttccatt    2760
gacgtcaatg ggtggagtat ttacggtaaa ctgcccactt ggcagtacat caagtgtatc    2820
atatgccaag tacgccccct attgacgtca atgacggtaa atggcccgcc tggcattatg    2880
cccagtacat gaccttatgg gactttccta cttggcagta catctacgta ttagtcatcg    2940
ctattaccat ggtgatgcgg ttttggcagt acatcaatgg gcgtggatag cggtttgact    3000
cacggggatt tccaagtctc cacccccattg acgtcaatgg gagtttgttt tggcaccaaa    3060
atcaacggga ctttccaaaa tgtcgtaaca actccgcccc attgacgcaa atgggcggta    3120
ggcgtgtacg gtgggaggtc tatataagca gagctctctg gctaactaga acccactg     3180 cttactggct tatcgaaatt aatacgactc actataggga gacccaagct ggctagggt    3240 accgaaatgg tgtggcaagt agacaggatg aggattagaa catggaacag tttagtaaaa    3300
catcacatgt atatctcaaa gaaagcaaaa aattggtttt atagacatca ctttgaaagc    3360
agtcatccaa gagtaagttc agaagtacac atcccactag gggatgctag attagtagta    3420
agaacatatt ggggtctgca tacaggagaa aaagattggc acttgggtaa tggggtgtcc    3480
atagaatgga gactaagaag atatagcaca caaatagatc ctgacctggc agaccaacta    3540
```

-continued

```
attcatctgc attattttaa ttgttttttca gactctgcca taaggaaagc catattagga   3600
caagtagtta gacctagatg tgactatcaa gcaggacata acaaggtagg atctgctcaa   3660
tatttggcac tgaaagcatt agtaacacca gtaaggacaa ggccacccttt gcctagtgtt   3720
aggaaattag cagaggacag atggaacaag ccccagaaaa ccaggggtcc cagagggagc   3780
catacaatga atggacatgc tagcgaaatg gcaccgaaga agaagcgtaa agtcggaatc   3840
cacggagttc ctgcggcaat ggacaagaag tactccattg gctcgctat cggcacaaac   3900
agcgtcggtt gggccgtcat tacggacgag tacaaggtgc cgagcaaaaa attcaaagtt   3960
ctgggcaata ccgatcgcca cagcataaag aagaacctca ttggcgccct cctgttcgac   4020
tccggggaga cggccgaagc cacgcggctc aaaagaacag cacggcgcag atatacccgc   4080
agaaagaatc ggatctgcta cctgcaggag atctttagta atgagatggc taaggtggat   4140
gactcttttct tccataggct ggaggagtcc ttttttggtgg aggaggataa aaagcacgag   4200
cgccacccaa tctttggcaa tatcgtggac gaggtggcgt accatgaaaa gtacccaacc   4260
atatatcatc tgaggaagaa gcttgtagac agtactgata aggctgactt gcggttgatc   4320
tatctcgcgc tggcgcatat gatcaaattt cggggacact tcctcatcga ggggacctg   4380
aacccagaca cagcgatgt cgacaaactc tttatccaac tggttcagac ttacaatcag   4440
cttttcgaag agaacccgat caacgcatcc ggagttgacg ccaaagcaat cctgagcgct   4500
aggctgtcca atcccggcg gctcgaaaac ctcatcgcac agctccctgg ggagaagaag   4560
aacggcctgt ttggtaatct tatcgccctg tcactcgggc tgaccccccaa ctttaaatct   4620
aacttcgacc tggccgaaga tgccaagctt caactgagca agacaccta cgatgatgat   4680
ctcgacaatc tgctggccca gatcggcgac cagtacgcag accttttttt ggcggcaaag   4740
aacctgtcag acgccattct gctgagtgat attctgcgag tgaacacgga gatcaccaaa   4800
gctccgctga gcgctagtat gatcaagcgc tatgatgagc accaccaaga cttgactttg   4860
ctgaaggccc ttgtcagaca gcaactgcct gagaagtaca aggaaattttt cttcgatcag   4920
tctaaaaatg gctacgccgg atacattgac ggcggagcaa gccaggagga atttttacaaa   4980
tttattaagc ccatcttgga aaaaatggac ggcaccgagg agctgctggt aaagcttaac   5040
agagaagatc tgttgcgcaa acagcgcact ttcgacaatg gaagcatccc ccaccagatt   5100
cacctgggcg aactgcacgc tatcctcagg cggcaagagg attctaccc cttttttgaaa   5160
gataacaggg aaaagattga gaaaatcctc acatttcgga tacccctacta tgtaggccc   5220
ctcgcccggg gaaattccag attgcgtgg atgactcgca aatcagaaga gaccatcact   5280
ccctggaact tcgaggaagt cgtggataag ggggcctctg cccagtcctt catcgaaagg   5340
atgactaact ttgataaaaa tctgcctaac gaaaaggtgc ttcctaaaca ctctctgctg   5400
tacgagtact tcacagttta taacgagctc accaaggtca aatacgtcac agaagggatg   5460
agaaagccag cattcctgtc tggagagcag aagaaagcta cgtggacct cctcttcaag   5520
acgaaccgga aagttaccgt gaaacagctc aaagaagact atttcaaaaa gattgaatgt   5580
ttcgactctg ttgaaatcag cggagtggag gatcgcttca acgcatccct gggaacgtat   5640
cacgatctcc tgaaaatcat taagacaag gacttcctgg acaatgagga gaacgaggac   5700
attcttgagg acattgtcct caccccttacg ttgtttgaag atagggagat gattgaagaa   5760
cgcttgaaaa cttacgctca tctcttcgac gacaaagtca tgaaacagct caaggagcgc   5820
cgatatacag gatgggggcg gctgtcaaga aaactgatca tgggatccg agacaagcag   5880
agtggaaaga caatcctgga ttttcttaag tccgatggat ttgccaaccg gaacttcatg   5940
```

```
cagttgatcc atgatgactc tctcaccttt aaggaggaca tccagaaagc acaagtttct   6000
ggccaggggg acagtcttca cgagcacatc gctaatcttg caggtagccc agctatcaaa   6060
aagggaatac tgcagaccgt taaggtcgtg gatgaactcg tcaaagtaat gggaaggcat   6120
aagcccgaga atatcgttat cgagatggcc cgagagaacc aaactaccca gaagggacag   6180
aagaacagta gggaaaggat gaagaggatt gaagagggta taaaagaact ggggtcccaa   6240
atccttaagg aacacccagt tgaaaacacc cagcttcaga atgagaagct ctacctgtac   6300
tacctgcaga acggcaggga catgtacgtg gatcaggaac tggacatcaa tcggctctcc   6360
gactacgacg tggatcatat cgtgccccag tcttttctca aagatgattc tattgataat   6420
aaagtgttga caagatccga taaaaataga gggaagagtg ataacgtccc ctcagaagaa   6480
gttgtcaaga aaatgaaaaa ttattggcgg cagctgctga cgccaaaact gatcacacaa   6540
cggaagttcg ataatctgac taaggctgaa cgaggtggcc tgtctgagtt ggataaagcc   6600
ggcttcatca aaaggcagct tgttgagaca cgccagatca ccaagcacgt ggcccaaatt   6660
ctcgattcac gcatgaacac caagtacgat gaaaatgaca aactgattcg agaggtgaaa   6720
gttattactc tgaagtctaa gctggtctca gatttcagaa aggactttca gttttataag   6780
gtgagagaga tcaacaatta ccaccatgcg catgatgcct acctgaatgc agtggtaggc   6840
actgcactta tcaaaaaata tcccaagctt gaatctgaat tgttacgg agactataaa    6900 gtgtacgatg ttaggaaaat gatcgcaaag tctgagcagg aaataggcaa ggccaccgct   6960
aagtacttct tttacagcaa tattatgaat ttttttcaaga ccgagattac actggccaat   7020
ggagagattc ggaagcgacc acttatcgaa acaaacggag aaacaggaga atcgtgtgg   7080 gacaagggta gggatttcgc gacagtccgg aaggtcctgt ccatgccgca ggtgaacatc   7140
gttaaaaaga ccgaagtaca gaccggaggc ttctccaagg aaagtatcct cccgaaaagg   7200
aacagcgaca agctgatcgc acgcaaaaaa gattgggacc ccaagaaata cggcggattc   7260
gattctccta cagtcgctta cagtgtactg gttgtggcca agtggagaa agggaagtct    7320 aaaaaactca aaagcgtcaa ggaactgctg ggcatcacaa tcatggagcg atcaagcttc   7380
gaaaaaaacc ccatcgactt tctcgaggcg aaaggatata agaggtcaa aaagacctc     7440 atcattaagc ttcccaagta ctctctcttt gagcttgaaa acggccggaa acgaatgctc   7500
gctagtgcgg gcgagctgca gaaaggtaac gagctggcac tgcccctcta aatacgttaat   7560 ttcttgtatc tggccagcca ctatgaaaag ctcaaagggt ctcccgaaga taatgagcag   7620
aagcagctgt tcgtggaaca acacaaacac taccttgatg agatcatcga gcaaataagc   7680
gaattctcca aaagagtgat cctcgccgac gctaacctcg ataaggtgct ttctgcttac   7740
aataagcaca gggataagcc catcaggag caggcagaaa acattatcca cttgtttact    7800
ctgaccaact gggcgcgcc tgcagccttc aagtacttcg acaccaccat agacagaaag   7860
cggtacacct ctacaaagga ggtcctggac gccacactga ttcatcagtc aattacgggg   7920
ctctatgaaa caagaatcga cctctctcag ctcggtggag accccaagaa gaaaagaaaa   7980
gtcggtacca tgaccaacct ttccgacatc atagagaagg aaacaggcaa acagttggtc   8040
atccaagagt cgatactcat gcttcctgaa gaagttgagg aggtcattgg gaataagccg   8100
gaaagtgaca ttctcgtaca cactgcgtat gatgagagca ccgatgagaa cgtgatgctg   8160
ctcacgtcag atgccccaga gtacaaaccc tgggctctgg tgattcagga ctctaatgga   8220
gagaacaaga tcaagatgct agaaggcagg ggaagccttc tgacttgtgg ggatgtggaa   8280
```

```
gaaaaccctg gtccatctag aatgaccgag tacaagccca cggtgcgcct cgccacccgc    8340
gacgacgtcc cccgggccgt acgcaccctc gccgccgcgt tcgccgacta ccccgccacg    8400
cgccacaccg tcgacccgga ccgccacatc gagcgggtca ccgagctgca agaactcttc    8460
ctcacgcgcg tcgggctcga catcggcaag gtgtgggtcg cggacgacgg cgccgcggtg    8520
gcggtctgga ccacgccgga gagcgtcgaa gcggggggcgg tgttcgccga gatcggcccg    8580
cgcatggccg agttgagcgg ttcccggctg gccgcgcagc aacagatgga aggcctcctg    8640
gcgccgcacc ggcccaagga gcccgcgtgg ttcctggcca ccgtcggcgt ctcgcccgac    8700
caccagggca agggtctggg cagcgccgtc gtgctccccg gagtggaggc ggccgagcgc    8760
gccggggtgc ccgccttcct ggagacctcc gcgccccgca acctcccctt ctacgagcgg    8820
ctcggcttca ccgtcaccgc cgacgtcgag gtgcccgaag accgcgcac ctggtgcatg    8880 acccgcaagc ccggtgcctg agcgggactc tggggttcga aatgaccgac caagcgacgc    8940
ccaacctgcc atcacgagat ttcgattcca ccgccgcctt ctatgaaagg ttgggcttcg    9000
gaatcgtttt ccgggacgcc ggctggatga tcctccagcg cggggatctc atgctggagt    9060
tcttcgccca ccccaacttg tttattgcag cttataatgg ttacaaataa agcaatagca    9120
tcacaaattt cacaaataaa gcatttttt cactgcattc tagttgtggt ttgtccaaac    9180
tcatcaatgt atcttagc                                                  9198
```

<210> SEQ ID NO 30
<211> LENGTH: 8859
<212> TYPE: DNA
<213> ORGANISM: Artificial Sequence
<220> FEATURE:
<223> OTHER INFORMATION: Synthetic Sequence Complete nucleotide
      sequence of vector 1931
<220> FEATURE:
<221> NAME/KEY: rep_origin
<222> LOCATION: (476)..(1064)
<223> OTHER INFORMATION: ori
<220> FEATURE:
<221> NAME/KEY: gene
<222> LOCATION: (1235)..(2095)
<223> OTHER INFORMATION: AmpR
<220> FEATURE:
<221> NAME/KEY: promoter
<222> LOCATION: (2096)..(2200)
<223> OTHER INFORMATION: AmpR promoter
<220> FEATURE:
<221> NAME/KEY: promoter
<222> LOCATION: (2233)..(2461)
<223> OTHER INFORMATION: H1 promoter
<220> FEATURE:
<221> NAME/KEY: misc_feature
<222> LOCATION: (2462)..(2481)
<223> OTHER INFORMATION: Target (HPRT site 1)
<220> FEATURE:
<221> NAME/KEY: misc_structure
<222> LOCATION: (2482)..(2557)
<223> OTHER INFORMATION: tracrRNA
<220> FEATURE:
<221> NAME/KEY: enhancer
<222> LOCATION: (2572)..(2951)
<223> OTHER INFORMATION: CMV enhancer
<220> FEATURE:
<221> NAME/KEY: promoter
<222> LOCATION: (2952)..(3155)
<223> OTHER INFORMATION: CMV promoter
<220> FEATURE:
<221> NAME/KEY: gene
<222> LOCATION: (3253)..(3672)
<223> OTHER INFORMATION: fragment of TopBv2 (452-591)
<220> FEATURE:
<221> NAME/KEY: misc_feature
<222> LOCATION: (3691)..(3741)

```
<223> OTHER INFORMATION: NLS unit
<220> FEATURE:
<221> NAME/KEY: misc_feature
<222> LOCATION: (3697)..(3717)
<223> OTHER INFORMATION: SV40 NLS
<220> FEATURE:
<221> NAME/KEY: gene
<222> LOCATION: (3742)..(7878)
<223> OTHER INFORMATION: nCas9 (D10A)
<220> FEATURE:
<221> NAME/KEY: misc_feature
<222> LOCATION: (7858)..(7878)
<223> OTHER INFORMATION: SV40 NLS
<220> FEATURE:
<221> NAME/KEY: misc_feature
<222> LOCATION: (7903)..(7956)
<223> OTHER INFORMATION: T2A
<220> FEATURE:
<221> NAME/KEY: gene
<222> LOCATION: (7963)..(8562)
<223> OTHER INFORMATION: PuroR
<220> FEATURE:
<221> NAME/KEY: polyA_signal
<222> LOCATION: (8736)..(8857)
<223> OTHER INFORMATION: SV40 poly(A) siglan

<400> SEQUENCE: 30
ggccgccacc gcggtggagc tccagctttt gttcccttta gtgagggtta attgcgcgct     60
tggcgtaatc atggtcatag ctgtttcctg tgtgaaattg ttatccgctc acaattccac    120
acaacatacg agccggaagc ataaagtgta aagcctgggg tgcctaatga gtgagctaac    180
tcacattaat tgcgttgcgc tcactgcccg ctttccagtc gggaaacctg tcgtgccagc    240
tgcattaatg aatcggccaa cgcgcgggga gaggcggttt gcgtattggg cgctcttccg    300
cttcctcgct cactgactcg ctgcgctcgg tcgttcggct gcggcgagcg gtatcagctc    360
actcaaaggc ggtaatacgg ttatccacag aatcagggga taacgcagga agaacatgt    420 gagcaaaagg ccagcaaaag gccaggaacc gtaaaaaggc cgcgttgctg gcgttttttcc    480 ataggctccg cccccctgac gagcatcaca aaaatcgacg ctcaagtcag aggtggcgaa    540
acccgacagg actataaaga taccaggcgt ttccccctgg aagctccctc gtgcgctctc    600
ctgttccgac cctgccgctt accggatacc tgtccgcctt ctcccttcg ggaagcgtgg    660 cgctttctca tagctcacgc tgtaggtatc tcagttcggt gtaggtcgtt cgctccaagc    720
tgggctgtgt gcacgaaccc cccgttcagc ccgaccgctg cgccttatcc ggtaactatc    780
gtcttgagtc caacccggta agacacgact tatcgccact ggcagcagcc actggtaaca    840
ggattagcag agcgaggtat gtaggcggtg ctacagagtt cttgaagtgg tggcctaact    900
acggctacac tagaaggaca gtatttggta tctgcgctct gctgaagcca gttaccttcg    960
gaaaaagagt tggtagctct tgatccggca acaaaccac cgctggtagc ggtggttttt   1020
ttgtttgcaa gcagcagatt acgcgcagaa aaaaaggatc tcaagaagat cctttgatct   1080
tttctacggg gtctgacgct cagtggaacg aaaactcacg ttaagggatt ttggtcatga   1140
gattatcaaa aaggatcttc acctagatcc ttttaaatta aaaatgaagt tttaaatcaa   1200
tctaaagtat atatgagtaa acttggtctg acagttacca atgcttaatc agtgaggcac   1260
ctatctcagc gatctgtcta tttcgttcat ccatagttgc ctgactcccc gtcgtgtaga   1320
taactacgat acgggagggc ttaccatctg gccccagtgc tgcaatgata ccgcgagacc   1380
cacgctcacc ggctccagat ttatcagcaa taaaccagcc agccggaagg gccgagcgca   1440
gaagtggtcc tgcaacttta tccgcctcca tccagtctat taattgttgc cgggaagcta   1500
gagtaagtag ttcgccagtt aatagtttgc gcaacgttgt tgccattgct acaggcatcg   1560
```

```
tggtgtcacg ctcgtcgttt ggtatggctt cattcagctc cggttcccaa cgatcaaggc    1620
gagttacatg atcccccatg ttgtgcaaaa aagcggttag ctccttcggt cctccgatcg    1680
ttgtcagaag taagttggcc gcagtgttat cactcatggt tatggcagca ctgcataatt    1740
ctcttactgt catgccatcc gtaagatgct tttctgtgac tggtgagtac tcaaccaagt    1800
cattctgaga atagtgtatg cggcgaccga gttgctcttg cccggcgtca atacgggata    1860
ataccgcgcc acatagcaga actttaaaag tgctcatcat tggaaaacgt tcttcggggc    1920
gaaaactctc aaggatctta ccgctgttga gatccagttc gatgtaaccc actcgtgcac    1980
ccaactgatc ttcagcatct tttactttca ccagcgtttc tgggtgagca aaaacaggaa    2040
ggcaaaatgc cgcaaaaaag ggaataaggg cgacacggaa atgttgaata ctcatactct    2100
tcctttttca atattattga agcatttatc agggttattg tctcatgagc ggatacatat    2160
ttgaatgtat ttagaaaaat aaacaaatag gggttccgcg cacatttccc cgaaaagtgc    2220
caccggtgta ccaattcgaa cgctgacgtc atcaacccgc tccaaggaat cgcgggccca    2280
gtgtcactag gcgggaacac ccagcgcgcg tgcgccctgg caggaagatg gctgtgaggg    2340
acaggggagt ggcgccctgc aatatttgca tgtcgctatg tgttctggga atcaccata    2400 aacgtgaaat gtctttggat ttgggaatct tataagttct gtatgaggac cacagatccc    2460
ctcgagatgt gatgaaggag agttttagag ctagaaatag caagttaaaa taaggctagt    2520
ccgttatcaa cttgaaaaag tggcaccgag tcggtgcttt ttttacgcgt tgacattgat    2580
tattgactag ttattaatag taatcaatta cggggtcatt agttcatagc ccatatatgg    2640
agttccgcgt tacataactt acggtaaatg gcccgcctgg ctgaccgccc aacgaccccc    2700
gcccattgac gtcaataatg acgtatgttc ccatagtaac gccaataggg actttccatt    2760
gacgtcaatg ggtggagtat ttacggtaaa ctgcccactt ggcagtacat caagtgtatc    2820
atatgccaag tacgccccct attgacgtca atgacggtaa atggcccgcc tggcattatg    2880
cccagtacat gaccttatgg gactttccta cttggcagta catctacgta ttagtcatcg    2940
ctattaccat ggtgatgcgg ttttggcagt acatcaatgg gcgtggatag cggtttgact    3000
cacggggatt tccaagtctc cacccattg acgtcaatgg gagtttgttt tggcaccaaa    3060
atcaacggga ctttccaaaa tgtcgtaaca actccgcccc attgacgcaa atgggcggta    3120
ggcgtgtacg gtgggaggtc tatataagca gagctctctg gctaactaga acccactg    3180 cttactggct tatcgaaatt aatacgactc actataggga gacccaagct ggctagcgaa    3240
atgggtaccg gaaaaggtat tcccaaactg gatgatgcta atgatgctgg tggtaaacat    3300
tccctggagt gtacactgat attaacagag ggagactctg ccaaatcact ggctgtgtct    3360
ggattaggtg tgattggacg agacagatac ggagttttc cactcagggg caaaattctt    3420
aatgtacggg aagcttctca taaacagatc atggaaaatg ctgaaataaa taatattatt    3480
aaaatagttg gtctacaata taagaaaagt tacgatgatg cagaatctct gaaaaccta    3540 cgctatggaa agattatgat tatgaccgat caggatcaag atggttctca cataaaaggc    3600
ctgcttatta atttcatcca tcacaattgg ccatcacttt tgaagcatgg ttttcttgaa    3660
gagttcatta ctgagggtga ccctagcgaa atggcaccga agaagaagcg taaagtcgga    3720
atccacggag ttcctgcggc aatggacaag aagtactcca ttgggctcgc tatcggcaca    3780
aacagcgtcg gttgggccgt cattacggac gagtacaagg tgccgagcaa aaaattcaaa    3840
gttctgggca ataccgatcg ccacagcata aagaagaacc tcattggcgc cctcctgttc    3900
```

```
gactccgggg agacggccga agccacgcgg ctcaaaagaa cagcacggcg cagatatacc    3960
cgcagaaaga atcggatctg ctacctgcag gagatcttta gtaatgagat ggctaaggtg    4020
gatgactctt tcttccatag gctggaggag tccttttgg tggaggagga taaaaagcac    4080
gagcgccacc caatctttgg caatatcgtg gacgaggtgg cgtaccatga aaagtaccca    4140
accatatatc atctgaggaa gaagcttgta gacagtactg ataaggctga cttgcggttg    4200
atctatctcg cgctggcgca tatgatcaaa tttcggggac acttcctcat cgaggggac    4260 ctgaacccag acaacagcga tgtcgacaaa ctctttatcc aactggttca gacttacaat    4320
cagcttttcg aagagaaccc gatcaacgca tccggagttg acgccaaagc aatcctgagc    4380
gctaggctgt ccaaatcccg gcggctcgaa aacctcatcg cacagctccc tggggagaag    4440
aagaacggcc tgtttggtaa tcttatcgcc ctgtcactcg gctgacccc caactttaaa    4500 tctaacttcg acctggccga agatgccaag cttcaactga gcaaagacac ctacgatgat    4560
gatctcgaca atctgctggc ccagatcggc gaccagtacg cagaccttt tttggcggca    4620 aagaacctgt cagacgccat tctgctgagt gatattctgc gagtgaacac ggagatcacc    4680
aaagctccgc tgagcgctag tatgatcaag cgctatgatg agcaccacca agacttgact    4740
ttgctgaagg cccttgtcag acagcaactg cctgagaagt acaaggaaat tttcttcgat    4800
cagtctaaaa atggctacgc cggatacatt gacggcggag caagccagga ggaattttac    4860
aaatttatta agcccatctt ggaaaaaatg gacggcaccg aggagctgct ggtaaagctt    4920
aacagagaag atctgttgcg caaacagcgc actttcgaca atggaagcat cccccaccag    4980
attcacctgg gcgaactgca cgctatcctc aggcggcaag aggatttcta cccctttttg    5040
aaagataaca gggaaaagat tgagaaaatc ctcacatttc ggatacccta ctatgtaggc    5100
cccctcgccc ggggaaattc cagattcgcg tggatgactc gcaaatcaga agagaccatc    5160
actccctgga acttcgagga agtcgtggat aagggggcct ctgcccagtc cttcatcgaa    5220
aggatgacta actttgataa aaatctgcct aacgaaaagg tgcttcctaa acactctctg    5280
ctgtacgagt acttcacagt ttataacgag ctcaccaagg tcaaatacgt cacagaaggg    5340
atgagaaagc cagcattcct gtctggagag cagaagaaag ctatcgtgga cctcctcttc    5400
aagacgaacc ggaaagttac cgtgaaacag ctcaaagaag actatttcaa aaagattgaa    5460
tgtttcgact ctgttgaaat cagcggagtg gaggatcgct tcaacgcatc cctgggaacg    5520
tatcacgatc tcctgaaaat cattaaagac aaggacttcc tggacaatga ggagaacgag    5580
gacattcttg aggacattgt cctcaccctt acgttgtttg aagatagggga gatgattgaa    5640 gaacgcttga aaacttacgc tcatctcttc gacgacaaag tcatgaaaca gctcaagagg    5700
cgccgatata caggatgggg gcggctgtca agaaaactga tcaatgggat ccagacaag    5760 cagagtggaa agacaatcct ggattttctt aagtccgatg gatttgccaa ccggaacttc    5820
atgcagttga tccatgatga ctctctcacc tttaaggagg catccagaa agcacaagtt    5880 tctggccagg gggacagtct tcacgagcac atcgctaatc ttgcaggtag cccagctatc    5940
aaaaagggaa tactgcagac cgttaaggtc gtggatgaac tcgtcaaagt aatgggaagg    6000
cataagcccg agaatatcgt tatcgagatg gcccgagaga accaaactac ccagaaggga    6060
cagaagaaca gtagggaaag gatgaagagg attgaagagg gtataaaaga actggggtcc    6120
caaatcctta aggaacaccc agttgaaaac acccagcttc agaatgagaa gctctacctg    6180
tactacctgc agaacggcag ggacatgtac gtggatcagg aactggacat caatcggctc    6240
tccgactacg acgtggatca tatcgtgccc cagtctttc tcaaagatga ttctattgat    6300
```

```
aataaagtgt tgacaagatc cgataaaaat agagggaaga gtgataacgt cccctcagaa    6360
gaagttgtca agaaaatgaa aaattattgg cggcagctgc tgaacgccaa actgatcaca    6420
caacggaagt tcgataatct gactaaggct gaacgaggtg gcctgtctga gttggataaa    6480
gccggcttca tcaaaaggca gcttgttgag acacgccaga tcaccaagca cgtggcccaa    6540
attctcgatt cacgcatgaa caccaagtac gatgaaaatg acaaactgat tcgagaggtg    6600
aaagttatta ctctgaagtc taagctggtc tcagatttca gaaaggactt tcagttttat    6660
aaggtgagag agatcaacaa ttaccaccat gcgcatgatg cctacctgaa tgcagtggta    6720
ggcactgcac ttatcaaaaa atatcccaag cttgaatctg aatttgttta cggagactat    6780
aaagtgtacg atgttaggaa aatgatcgca aagtctgagc aggaaatagg caaggccacc    6840
gctaagtact tctttttacag caatattatg aatttttttca agaccgagat tacactggcc    6900
aatggagaga ttcggaagcg accacttatc gaaacaaacg gagaaacagg agaaatcgtg    6960
tgggacaagg gtagggattt cgcgacagtc cggaaggtcc tgtccatgcc gcaggtgaac    7020
atcgttaaaa agaccgaagt acagaccgga ggcttctcca aggaaagtat cctcccgaaa    7080
aggaacagcg acaagctgat cgcacgcaaa aaagattggg accccaagaa atacggcgga    7140
ttcgattctc ctacagtcgc ttacagtgta ctggttgtgg ccaaagtgga gaagggaag    7200 tctaaaaaac tcaaaagcgt caaggaactg ctgggcatca caatcatgga gcgatcaagc    7260
ttcgaaaaaa accccatcga cttctcgag gcgaaaggat ataagaggt caaaaaagac    7320 ctcatcatta agcttcccaa gtactctctc tttgagcttg aaaacggccg gaaacgaatg    7380
ctcgctagtg cgggcgagct gcagaaaggt aacgagctgg cactgccctc taaatacgtt    7440
aatttcttgt atctgccag ccactatgaa aagctcaaag gtctcccga agataatgag    7500 cagaagcagc tgttcgtgga acaacacaaa cactaccttg atgagatcat cgagcaaata    7560
agcgaattct ccaaaagagt gatcctcgcc gacgctaacc tcgataaggt gctttctgct    7620
tacaataagc acagggataa gcccatcagg gagcaggcag aaaacattat ccacttgttt    7680
actctgacca acttgggcgc gcctgcagcc ttcaagtact tcgacaccac catagacaga    7740
aagcggtaca cctctacaaa ggaggtcctg gacgccacac tgattcatca gtcaattacg    7800
gggctctatg aaacaagaat cgacctctct cagctcggtg gagacagcag ggctgacccc    7860
aagaagaaga ggaaggtggg tgaggaggt accctagga ccgaaggcag gggaagcctt    7920
ctgacttgtg gggatgtgga agaaaaccct ggtccatcta gaatgaccga gtacaagccc    7980
acggtgcgcc tcgccacccg cgacgacgtc ccccgggccg tacgcaccct cgccgccgcg    8040
ttcgccgact accccgccac gcgccacacc gtcgacccgg accgccacat cgagcgggtc    8100
accgagctgc aagaactctt cctcacgcgc gtcgggctcg acatcggcaa ggtgtgggtc    8160
gcggacgacg gcgccgcggt ggcggtctgg accacgccgg agagcgtcga agcggggcg    8220 gtgttcgccg agatcggccc cgcatggcc gagttgagcg gttcccggct ggccgcgcag    8280
caacagatgg aaggcctcct ggcgccgcac cggcccaagg agcccgcgtg gttcctggcc    8340
accgtcggcg tctcgcccga ccaccagggc aagggtctgg cagcgccgt cgtgctcccc    8400 ggagtggagg cggccgagcg cgccggggtg cccgccttcc tggagacctc cgcgcccgc    8460 aacctccccct tctacgagcg gctcggcttc accgtcaccg ccgacgtcga ggtgcccgaa    8520
ggaccgcgca cctggtgcat gacccgcaag cccggtgcct gagcgggact ctggggttcg    8580
aaatgaccga ccaagcgacg cccaacctgc catcacgaga tttcgattcc accgccgcct    8640
```

```
tctatgaaag gttgggcttc ggaatcgttt tccgggacgc cggctggatg atcctccagc    8700
gcggggatct catgctggag ttcttcgccc accccaactt gtttattgca gcttataatg    8760
gttacaaata aagcaatagc atcacaaatt tcacaaataa agcattttt tcactgcatt     8820 ctagttgtgg tttgtccaaa ctcatcaatg tatcttagc                           8859
```

```
<210> SEQ ID NO 31
<211> LENGTH: 9141
<212> TYPE: DNA
<213> ORGANISM: Artificial Sequence
<220> FEATURE:
<223> OTHER INFORMATION: Synthetic Sequence Complete nucleotide
      sequence of vector 1932
<220> FEATURE:
<221> NAME/KEY: rep_origin
<222> LOCATION: (476)..(1064)
<223> OTHER INFORMATION: ori
<220> FEATURE:
<221> NAME/KEY: gene
<222> LOCATION: (1235)..(2095)
<223> OTHER INFORMATION: AmpR
<220> FEATURE:
<221> NAME/KEY: promoter
<222> LOCATION: (2096)..(2200)
<223> OTHER INFORMATION: AmpR promoter
<220> FEATURE:
<221> NAME/KEY: promoter
<222> LOCATION: (2233)..(2461)
<223> OTHER INFORMATION: H1 promoter
<220> FEATURE:
<221> NAME/KEY: misc_feature
<222> LOCATION: (2462)..(2481)
<223> OTHER INFORMATION: Target (HPRT site 1)
<220> FEATURE:
<221> NAME/KEY: misc_structure
<222> LOCATION: (2482)..(2557)
<223> OTHER INFORMATION: tracrRNA
<220> FEATURE:
<221> NAME/KEY: enhancer
<222> LOCATION: (2572)..(2951)
<223> OTHER INFORMATION: CMV enhancer
<220> FEATURE:
<221> NAME/KEY: promoter
<222> LOCATION: (2952)..(3155)
<223> OTHER INFORMATION: CMV promoter
<220> FEATURE:
<221> NAME/KEY: misc_feature
<222> LOCATION: (3241)..(3291)
<223> OTHER INFORMATION: NLS unit
<220> FEATURE:
<221> NAME/KEY: misc_feature
<222> LOCATION: (3247)..(3267)
<223> OTHER INFORMATION: SV40 NLS
<220> FEATURE:
<221> NAME/KEY: gene
<222> LOCATION: (3292)..(7428)
<223> OTHER INFORMATION: nCas9 (D10A)
<220> FEATURE:
<221> NAME/KEY: misc_feature
<222> LOCATION: (7408)..(7428)
<223> OTHER INFORMATION: SV40 NLS
<220> FEATURE:
<221> NAME/KEY: gene
<222> LOCATION: (7447)..(7692)
<223> OTHER INFORMATION: fragment of IQGAP2 (466-547)
<220> FEATURE:
<221> NAME/KEY: gene
<222> LOCATION: (7717)..(8163)
<223> OTHER INFORMATION: fragment of NIF-ZFN335_745-893 (466-547)
<220> FEATURE:
<221> NAME/KEY: misc_feature
<222> LOCATION: (8185)..(8238)
<223> OTHER INFORMATION: T2A
<220> FEATURE:
<221> NAME/KEY: gene
<222> LOCATION: (8245)..(8844)
```

<223> OTHER INFORMATION: PuroR
<220> FEATURE:
<221> NAME/KEY: polyA_signal
<222> LOCATION: (9018)..(9139)
<223> OTHER INFORMATION: SV40 poly(A) signal

<400> SEQUENCE: 31

| | | | | | |
|---|---|---|---|---|---|
| ggccgccacc | gcggtggagc | tccagctttt | gttcccttta | gtgagggtta | attgcgcgct | 60 |
| tggcgtaatc | atggtcatag | ctgtttcctg | tgtgaaattg | ttatccgctc | acaattccac | 120 |
| acaacatacg | agccggaagc | ataaagtgta | aagcctgggg | tgcctaatga | gtgagctaac | 180 |
| tcacattaat | tgcgttgcgc | tcactgcccg | ctttccagtc | gggaaacctg | tcgtgccagc | 240 |
| tgcattaatg | aatcggccaa | cgcgcgggga | gaggcggttt | gcgtattggg | cgctcttccg | 300 |
| cttcctcgct | cactgactcg | ctgcgctcgg | tcgttcggct | gcggcgagcg | gtatcagctc | 360 |
| actcaaaggc | ggtaatacgg | ttatccacag | aatcagggga | taacgcagga | aagaacatgt | 420 |
| gagcaaaagg | ccagcaaaag | gccaggaacc | gtaaaaaggc | cgcgttgctg | gcgtttttcc | 480 |
| ataggctccg | cccccctgac | gagcatcaca | aaaatcgacg | ctcaagtcag | aggtggcgaa | 540 |
| acccgacagg | actataaaga | taccaggcgt | ttccccctgg | aagctccctc | gtgcgctctc | 600 |
| ctgttccgac | cctgccgctt | accggatacc | tgtccgcctt | tctcccttcg | ggaagcgtgg | 660 |
| cgctttctca | tagctcacgc | tgtaggtatc | tcagttcggt | gtaggtcgtt | cgctccaagc | 720 |
| tgggctgtgt | gcacgaaccc | cccgttcagc | ccgaccgctg | cgccttatcc | ggtaactatc | 780 |
| gtcttgagtc | caacccggta | agacacgact | tatcgccact | ggcagcagcc | actggtaaca | 840 |
| ggattagcag | agcgaggtat | gtaggcggtg | ctacagagtt | cttgaagtgg | tggcctaact | 900 |
| acggctacac | tagaaggaca | gtatttggta | tctgcgctct | gctgaagcca | gttaccttcg | 960 |
| gaaaaagagt | tggtagctct | tgatccggca | aacaaaccac | cgctggtagc | ggtggttttt | 1020 |
| ttgtttgcaa | gcagcagatt | acgcgcagaa | aaaaggatc | tcaagaagat | cctttgatct | 1080 |
| tttctacggg | gtctgacgct | cagtggaacg | aaaactcacg | ttaagggatt | ttggtcatga | 1140 |
| gattatcaaa | aaggatcttc | acctagatcc | ttttaaatta | aaaatgaagt | tttaaatcaa | 1200 |
| tctaaagtat | atatgagtaa | acttggtctg | acagttacca | atgcttaatc | agtgaggcac | 1260 |
| ctatctcagc | gatctgtcta | tttcgttcat | ccatagttgc | ctgactcccc | gtcgtgtaga | 1320 |
| taactacgat | acgggagggc | ttaccatctg | gccccagtgc | tgcaatgata | ccgcgagacc | 1380 |
| cacgctcacc | ggctccagat | ttatcagcaa | taaaccagcc | agccggaagg | gccgagcgca | 1440 |
| gaagtggtcc | tgcaacttta | tccgcctcca | tccagtctat | taattgttgc | cgggaagcta | 1500 |
| gagtaagtag | ttcgccagtt | aatagtttgc | gcaacgttgt | tgccattgct | acaggcatcg | 1560 |
| tggtgtcacg | ctcgtcgttt | ggtatggctt | cattcagctc | cggttcccaa | cgatcaaggc | 1620 |
| gagttacatg | atcccccatg | ttgtgcaaaa | aagcggttag | ctccttcggt | cctccgatcg | 1680 |
| ttgtcagaag | taagttggcc | gcagtgttat | cactcatggt | tatggcagca | ctgcataatt | 1740 |
| ctcttactgt | catgccatcc | gtaagatgct | tttctgtgac | tggtgagtac | tcaaccaagt | 1800 |
| cattctgaga | atagtgtatg | cggcgaccga | gttgctcttg | cccggcgtca | atacgggata | 1860 |
| ataccgcgcc | acatagcaga | actttaaaag | tgctcatcat | tggaaaacgt | tcttcggggc | 1920 |
| gaaaactctc | aaggatctta | ccgctgttga | gatccagttc | gatgtaaccc | actcgtgcac | 1980 |
| ccaactgatc | ttcagcatct | tttactttca | ccagcgtttc | tgggtgagca | aaaacaggaa | 2040 |
| ggcaaaatgc | cgcaaaaaag | ggaataaggg | cgacacggaa | atgttgaata | ctcatactct | 2100 |
| tcctttttca | atattattga | agcatttatc | agggttattg | tctcatgagc | ggatacatat | 2160 |

```
ttgaatgtat ttagaaaaat aaacaaatag gggttccgcg cacatttccc cgaaaagtgc    2220
caccggtgta ccaattcgaa cgctgacgtc atcaacccgc tccaaggaat cgcgggccca    2280
gtgtcactag gcgggaacac ccagcgcgcg tgcgccctgg caggaagatg gctgtgaggg    2340
acaggggagt ggcgccctgc aatatttgca tgtcgctatg tgttctggga atcaccata    2400 aacgtgaaat gtctttggat ttgggaatct tataagttct gtatgaggac cacagatccc    2460
ctcgagatgt gatgaaggag agttttagag ctagaaatag caagttaaaa taaggctagt    2520
ccgttatcaa cttgaaaaag tggcaccgag tcggtgcttt ttttacgcgt tgacattgat    2580
tattgactag ttattaatag taatcaatta cggggtcatt agttcatagc ccatatatgg    2640
agttccgcgt tacataactt acggtaaatg gcccgcctgg ctgaccgccc aacgacccc    2700 gcccattgac gtcaataatg acgtatgttc ccatagtaac gccaataggg actttccatt    2760
gacgtcaatg ggtggagtat ttacggtaaa ctgcccactt ggcagtacat caagtgtatc    2820
atatgccaag tacgccccct attgacgtca atgacggtaa atggcccgcc tggcattatg    2880
cccagtacat gaccttatgg gactttccta cttggcagta catctacgta ttagtcatcg    2940
ctattaccat ggtgatgcgg ttttggcagt acatcaatgg gcgtggatag cggtttgact    3000
cacggggatt tccaagtctc cacccccattg acgtcaatgg gagtttgttt tggcaccaaa    3060
atcaacggga ctttccaaaa tgtcgtaaca actccgcccc attgacgcaa atgggcggta    3120
ggcgtgtacg gtgggaggtc tatataagca gagctctctg gctaactaga gaacccactg    3180
cttactggct tatcgaaatt aatacgactc actataggga gacccaagct ggctagcgaa    3240
atggcaccga agaagaagcg taaagtcgga atccacggag ttcctgcggc aatggacaag    3300
aagtactcca ttgggctcgc tatcggcaca acagcgtcg gttgggccgt cattacggac    3360
gagtacaagg tgccgagcaa aaaattcaaa gttctgggca ataccgatcg ccacagcata    3420
aagaagaacc tcattggcgc cctcctgttc gactccgggg agacggccga agccacgcgg    3480
ctcaaaagaa cagcacggcg cagatatacc cgcagaaaga tcggatctg ctacctgcag    3540 gagatcttta gtaatgagat ggctaaggtg gatgactctt tcttccatag gctggaggag    3600 tccttttttgg tggaggagga taaaaagcac gagcgccacc caatctttgg caatatcgtg    3660
gacgaggtgg cgtaccatga aaagtaccca accatatatc atctgaggaa gaagcttgta    3720
gacagtactg ataaggctga cttgcggttg atctatctcg cgctggcgca tatgatcaaa    3780
tttcggggac acttcctcat cgaggggac ctgaacccag acaacagcga tgtcgacaaa    3840
ctctttatcc aactggttca gacttacaat cagcttttcg aagagaaccc gatcaacgca    3900
tccggagttg acgccaaagc aatcctgagc gctaggctgt ccaaatcccg gcggctcgaa    3960
aacctcatcg cacagctccc tggggagaag aagaacggcc tgtttggtaa tcttatcgcc    4020
ctgtcactcg ggctgacccc caactttaaa tctaacttcg acctggccga agatgccaag    4080
cttcaactga gcaaagacac ctacgatgat gatctcgaca atctgctggc ccagatcggc    4140
gaccagtacg cagacctttt tttggcggca agaacctgt cagacgccat tctgctgagt    4200
gatattctgc gagtgaacac ggagatcacc aaagctccgc tgagcgctag tatgatcaag    4260
cgctatgatg agcaccacca agacttgact ttgctgaagg cccttgtcag acagcaactg    4320
cctgagaagt acaaggaaat tttcttcgat cagtctaaaa atggctacgc cggatacatt    4380
gacggcggag caagccagga ggaattttac aaatttatta agcccatctt ggaaaaaatg    4440
gacggcaccg aggagctgct ggtaaagctt aacagagaag atctgttgcg caaacagcgc    4500
```

```
actttcgaca atggaagcat cccccaccag attcacctgg gcgaactgca cgctatcctc    4560
aggcggcaag aggatttcta cccctttttg aaagataaca gggaaaagat tgagaaaatc    4620
ctcacatttc ggataccccta ctatgtaggc cccctcgccc ggggaaattc cagattcgcg    4680
tggatgactc gcaaatcaga agagaccatc actccctgga acttcgagga agtcgtggat    4740 aaggggcct ctgcccagtc cttcatcgaa aggatgacta actttgataa aaatctgcct    4800
aacgaaaagg tgcttcctaa acactctctg ctgtacgagt acttcacagt ttataacgag    4860
ctcaccaagg tcaaatacgt cacagaaggg atgagaaagc cagcattcct gtctggagag    4920
cagaagaaag ctatcgtgga cctcctcttc aagacgaacc ggaaagttac cgtgaaacag    4980
ctcaaagaag actatttcaa aaagattgaa tgtttcgact ctgttgaaat cagcggagtg    5040
gaggatcgct tcaacgcatc cctgggaacg tatcacgatc tcctgaaaat cattaaagac    5100
aaggacttcc tggacaatga ggagaacgag gacattcttg aggacattgt cctcacccctt    5160 acgttgtttg aagatagggaa gatgattgaa gaacgcttga aaacttacgc tcatctcttc    5220
gacgacaaag tcatgaaaca gctcaagagg cgccgatata caggatgggg gcggctgtca    5280
agaaaactga tcaatgggat ccgagacaag cagagtggaa agacaatcct ggattttctt    5340
aagtccgatg gatttgccaa ccggaacttc atgcagttga tccatgatga ctctctcacc    5400
tttaaggagg acatccagaa agcacaagtt tctggccagg gggacagtct tcacgagcac    5460
atcgctaatc ttgcaggtag cccagctatc aaaaagggaa tactgcagac cgttaaggtc    5520
gtggatgaac tcgtcaaagt aatgggaagg cataagcccg agaatatcgt tatcgagatg    5580
gcccgagaga accaaactac ccagaaggga cagaagaaca gtagggaaag gatgaagagg    5640
attgaagagg gtataaaaga actggggtcc caaatcctta aggaacaccc agttgaaaac    5700
acccagcttc agaatgagaa gctctacctg tactacctgc agaacggcag ggacatgtac    5760
gtggatcagg aactggacat caatcggctc tccgactacg acgtggatca tatcgtgccc    5820
cagtcttttc tcaaagatga ttctattgat aataaagtgt tgacaagatc cgataaaaat    5880
agagggaaga gtgataacgt cccctcagaa gaagttgtca gaaaatgaa aaattattgg    5940 cggcagctgc tgaacgccaa actgatcaca caacggaagt cgataatct gactaaggct    6000 gaacgaggtg gcctgtctga gttggataaa gccggcttca tcaaaaggca gcttgttgag    6060
acacgccaga tcaccaagca cgtggcccaa attctcgatt cacgcatgaa caccaagtac    6120
gatgaaaatg acaaactgat tcgagaggtg aaagttatta ctctgaagtc taagctggtc    6180
tcagatttca gaaaggactt tcagttttat aaggtgagag agatcaacaa ttaccaccat    6240
gcgcatgatg cctacctgaa tgcagtggta ggcactgcac ttatcaaaaa atatcccaag    6300
cttgaatctg aatttgttta cggagactat aaagtgtacg atgttaggaa atgatcgca    6360 aagtctgagc aggaaatagg caaggccacc gctaagtact ctttttacag caatattatg    6420
aattttttca agaccgagat tacactggcc aatggagaga ttcggaagcg accacttatc    6480
gaaacaaacg gagaaacagg agaaatcgtg tgggacaagg gtagggattt cgcgacagtc    6540
cggaaggtcc tgtccatgcc gcaggtgaac atcgttaaaa agaccgaagt acagaccgga    6600
ggcttctcca aggaaagtat cctcccgaaa ggaacagcg acaagctgat cgcacgcaaa    6660
aaagattggg accccaagaa atacggcgga ttcgattctc ctacagtcgc ttacagtgta    6720
ctggttgtgg ccaaagtgga gaagggaag tctaaaaaac tcaaaagcgt caaggaactg    6780
ctgggcatca caatcatgga gcgatcaagc ttcgaaaaaa accccatcga ctttctcgag    6840
gcgaaaggat ataagaggt caaaaaagac ctcatcatta agcttcccaa gtactctctc    6900
```

```
tttgagcttg aaaacggccg gaaacgaatg ctcgctagtg cgggcgagct gcagaaaggt    6960
aacgagctgg cactgccctc taaatacgtt aatttcttgt atctggccag ccactatgaa    7020
aagctcaaag ggtctcccga agataatgag cagaagcagc tgttcgtgga acaacacaaa    7080
cactaccttg atgagatcat cgagcaaata agcgaattct ccaaaagagt gatcctcgcc    7140
gacgctaacc tcgataaggt gctttctgct tacaataagc acagggataa gcccatcagg    7200
gagcaggcag aaaacattat ccacttgttt actctgacca acttgggcgc gcctgcagcc    7260
ttcaagtact tcgacaccac catagacaga aagcggtaca cctctacaaa ggaggtcctg    7320
gacgccacac tgattcatca gtcaattacg gggctctatg aaacaagaat cgacctctct    7380
cagctcggtg gagacagcag ggctgacccc aagaagaaga ggaaggtggg tggaggaggt    7440
accggagaag ggaatccttt gaggacttta gaaactttgc tcctacctac tgcgaatatt    7500
agtgatgtgg acccagccca tgcccagcac taccaggatg ttttatacca tgctaaatca    7560
cagaaactcg gagactctga gagtgttttcc aaagtgcttt ggctggatga gatacagcaa    7620
gccgtcgatg atgccaacgt ggacaaggac agagcaaaac aatgggttac tctggtggtt    7680
gatgttaatc agggaggccc taggggaaatg ggaggcagtt ccccaggacc tcctgagata    7740
cccccagagg cgacaacttt ccagtcatct gaggctccct cattgctctg ttctgacacc    7800
ctgggcggcg ccaccatcat ctaccagcaa ggagctgagg agtcgacagc gatggccacg    7860
cagacagcct tggatcttct gctgaacatg agtgctcagc gggaactggg gggcacagcc    7920
ctgcaggtgg ctgtggtgaa gtcggaagat gtggaagcag ggttagcatc ccctggtggg    7980
cagccctccc ctgaaggtgc cactccacag gtcgtcaccc tccacgtggc agagccaggg    8040
ggcggtgcag cagccgagag ccagctaggc cctcctgacc taccgcagat caccctggca    8100
cctggtccat ttggtgggac tggctacagt gtcatcacag cacccccctat ggaggaggga    8160 acaggagggt cacctactag gaccgaaggc aggggaagcc ttctgacttg tggggatgtg    8220
gaagaaaacc ctggtccatc tagaatgacc gagtacaagc cacggtgcg cctcgccacc    8280 cgcgacgacg tcccccgggc cgtacgcacc ctcgccgccg cgttcgccga ctaccccgcc    8340
acgcgccaca ccgtcgaccc ggaccgccac atcgagcggg tcaccgagct gcaagaactc    8400
ttcctcacgc gcgtcgggct cgacatcggc aaggtgtggg tcgcggacga cggcgccgcg    8460
gtggcggtct ggaccacgcc ggagagcgtc gaagcggggg cggtgttcgc cgagatcggc    8520
ccgcgcatgg ccgagttgag cggttcccgg ctggccgcgc agcaacagat ggaaggcctc    8580
ctggcgccgc accggcccaa ggagcccgcg tggttcctgg ccaccgtcgg cgtctcgccc    8640
gaccaccagg gcaagggtct gggcagcgcc gtcgtgctcc ccggagtgga ggcggccgag    8700
cgcgccgggg tgcccgcctt cctggagacc tccgcgcccc gcaacctccc cttctacgag    8760
cggctcggct tcaccgtcac cgccgacgtc gaggtgcccg aaggaccgcg cacctggtgc    8820
atgacccgca gcccggtgc ctgagcggga ctctggggtt cgaaatgacc gaccaagcga    8880
cgcccaacct gccatcacga gatttcgatt ccaccgccgc cttctatgaa aggttgggct    8940
tcggaatcgt tttccgggac gccggctgga tgatcctcca gcgcggggat ctcatgctgg    9000
agttcttcgc ccaccccaac ttgttttattg cagcttataa tggttacaaa taaagcaata    9060
gcatcacaaa tttcacaaat aaagcatttt tttcactgca ttctagttgt ggtttgtcca    9120
aactcatcaa tgtatcttag c                                              9141
```

<210> SEQ ID NO 32

```
<211> LENGTH: 10219
<212> TYPE: DNA
<213> ORGANISM: Artificial Sequence
<220> FEATURE:
<223> OTHER INFORMATION: Synthetic Sequence Complete nucleotide
      sequence of vector 1907
<220> FEATURE:
<221> NAME/KEY: gene
<222> LOCATION: (1238)..(2095)
<223> OTHER INFORMATION: AmpR
<220> FEATURE:
<221> NAME/KEY: promoter
<222> LOCATION: (2882)..(3110)
<223> OTHER INFORMATION: H1 promoter
<220> FEATURE:
<221> NAME/KEY: misc_feature
<222> LOCATION: (3111)..(3130)
<223> OTHER INFORMATION: Target (HPRT site 1)
<220> FEATURE:
<221> NAME/KEY: misc_structure
<222> LOCATION: (3131)..(3206)
<223> OTHER INFORMATION: tracrRNA
<220> FEATURE:
<221> NAME/KEY: enhancer
<222> LOCATION: (3221)..(3600)
<223> OTHER INFORMATION: CMV enhancer
<220> FEATURE:
<221> NAME/KEY: promoter
<222> LOCATION: (3601)..(3804)
<223> OTHER INFORMATION: CMV promoter
<220> FEATURE:
<221> NAME/KEY: misc_feature
<222> LOCATION: (3890)..(3940)
<223> OTHER INFORMATION: NLS unit
<220> FEATURE:
<221> NAME/KEY: misc_feature
<222> LOCATION: (3896)..(3916)
<223> OTHER INFORMATION: SV40 NLS
<220> FEATURE:
<221> NAME/KEY: gene
<222> LOCATION: (3941)..(8077)
<223> OTHER INFORMATION: nCas9 (D10A)
<220> FEATURE:
<221> NAME/KEY: misc_feature
<222> LOCATION: (8057)..(8077)
<223> OTHER INFORMATION: SV40 NLS
<220> FEATURE:
<221> NAME/KEY: misc_feature
<222> LOCATION: (8108)..(8278)
<223> OTHER INFORMATION: dead SH3 hs
<220> FEATURE:
<221> NAME/KEY: misc_feature
<222> LOCATION: (8285)..(8350)
<223> OTHER INFORMATION: 3xFLAG hs
<220> FEATURE:
<221> NAME/KEY: gene
<222> LOCATION: (8357)..(8980)
<223> OTHER INFORMATION: HsPmCDA1
<220> FEATURE:
<221> NAME/KEY: misc_feature
<222> LOCATION: (8984)..(9004)
<223> OTHER INFORMATION: SV40 NLS
<220> FEATURE:
<221> NAME/KEY: gene
<222> LOCATION: (9011)..(9262)
<223> OTHER INFORMATION: UGI
<220> FEATURE:
<221> NAME/KEY: misc_feature
<222> LOCATION: (9263)..(9316)
<223> OTHER INFORMATION: T2A
<220> FEATURE:
<221> NAME/KEY: gene
<222> LOCATION: (9323)..(9922)
<223> OTHER INFORMATION: PuroR
<220> FEATURE:
<221> NAME/KEY: polyA_signal
<222> LOCATION: (10096)..(10217)
<223> OTHER INFORMATION: SV40 poly(A) signal
```

<400> SEQUENCE: 32

```
ggccgccacc gcggtggagc tccagctttt gttcccttta gtgagggtta attgcgcgct      60
tggcgtaatc atggtcatag ctgtttcctg tgtgaaattg ttatccgctc acaattccac     120
acaacatacg agccggaagc ataaagtgta aagcctgggg tgcctaatga gtgagctaac     180
tcacattaat tgcgttgcgc tcactgcccg ctttccagtc gggaaacctg tcgtgccagc     240
tgcattaatg aatcggccaa cgcgcgggga gaggcggttt gcgtattggg cgctcttccg     300
cttcctcgct cactgactcg ctgcgctcgg tcgttcggct gcggcgagcg gtatcagctc     360
actcaaaggc ggtaatacgg ttatccacag aatcagggga taacgcagga agaacatgt     420
gagcaaaagg ccagcaaaag gccaggaacc gtaaaaaggc cgcgttgctg gcgttttttcc    480
ataggctccg cccccctgac gagcatcaca aaaatcgacg ctcaagtcag aggtggcgaa     540
acccgacagg actataaaga taccaggcgt ttccccctgg aagctccctc gtgcgctctc     600
ctgttccgac cctgccgctt accggatacc tgtccgcctt ctcccttcg ggaagcgtgg      660
cgctttctca tagctcacgc tgtaggtatc tcagttcggt gtaggtcgtt cgctccaagc     720
tgggctgtgt gcacgaaccc cccgttcagc ccgaccgctg cgccttatcc ggtaactatc     780
gtcttgagtc caacccggta agacacgact tatcgccact ggcagcagcc actggtaaca     840
ggattagcag agcgaggtat gtaggcggtg ctacagagtt cttgaagtgg tggcctaact     900
acggctacac tagaaggaca gtatttggta tctgcgctct gctgaagcca gttaccttcg     960
gaaaaagagt tggtagctct tgatccggca acaaaccac cgctggtagc ggtggttttt    1020
ttgtttgcaa gcagcagatt acgcgcagaa aaaaggatc tcaagaagat cctttgatct    1080
tttctacggg gtctgacgct cagtggaacg aaaactcacg ttaagggatt ttggtcatga    1140
gattatcaaa aaggatcttc acctagatcc ttttaaatta aaaatgaagt tttaaatcaa    1200
tctaaagtat atatgagtaa acttggtctg acagttacca atgcttaatc agtgaggcac    1260
ctatctcagc gatctgtcta tttcgttcat ccatagttgc ctgactcccc gtcgtgtaga    1320
taactacgat acgggagggc ttaccatctg gccccagtgc tgcaatgata ccgcgagacc    1380
cacgctcacc ggctccagat ttatcagcaa taaaccagcc agccggaagg gccgagcgca    1440
gaagtggtcc tgcaacttta tccgcctcca tccagtctat taattgttgc cgggaagcta    1500
gagtaagtag ttcgccagtt aatagtttgc gcaacgttgt tgccattgct acaggcatcg    1560
tggtgtcacg ctcgtcgttt ggtatggctt cattcagctc cggttcccaa cgatcaaggc    1620
gagttacatg atccccccatg ttgtgcaaaa aagcggttag ctccttcggt cctccgatcg    1680
ttgtcagaag taagttggcc gcagtgttat cactcatggt tatggcagca ctgcataatt    1740
ctcttactgt catgccatcc gtaagatgct tttctgtgac tggtgagtac tcaaccaagt    1800
cattctgaga atagtgtatg cggcgaccga gttgctcttg cccggcgtca atacgggata    1860
ataccgcgcc acatagcaga actttaaaag tgctcatcat tggaaaacgt tcttcggggc    1920
gaaaactctc aaggatctta ccgctgttga tccagttc gatgtaaccc actcgtgcac    1980
ccaactgatc ttcagcatct tttactttca ccagcgtttc tgggtgagca aaaacaggaa    2040
ggcaaaatgc cgcaaaaaag gaataaggg cgacacggaa atgttgaata ctcatactct    2100
tcctttttca atattattga agcatttatc agggttattg tctcatgagc ggatacatat    2160
ttgaatgtat ttagaaaaat aaacaaatag gggttccgcg cacatttccc cgaaaagtgc    2220
cacctaaatt gtaagcgtta atattttgtt aaaattcgcg ttaaattttt gttaaatcag    2280
ctcattttt aaccaatagg ccgaaatcgg caaaatccct tataaatcaa agaatagac      2340
```

```
cgagatagggttgagtgttgttccagtttggaacaagagtccactattaaagaacgtgga      2400 ctccaacgtcaaagggcgaaaaaccgtctatcagggcgatggcccactacgtgaaccatc     2460 accctaatcaagttttttggggtcgaggtgccgtaaagcactaaatcggaaccctaaagg     2520 gagcccccgatttagagcttgacggggaaagccggcgaacgtggcgagaaaggaagggaa     2580 gaaagcgaaaggagcgggcgctagggcgctggcaagtgtagcggtcacgctgcgcgtaac     2640 caccacacccgccgcgcttaatgcgccgctacagggcgcgtcccattcgccattcaggct     2700 gcgcaactgttgggaagggcgatcggtgcgggcctcttcgctattacgccagctggcgaa     2760 agggggatgtgctgcaaggcgattaagttggtaacgccagggttttcccagtcacgacg     2820 ttgtaaaacgacggccagtgagcgcgcgtaatacgactcactatagggcgaattgggtac     2880 caattcgaacgctgacgtcatcaacccgctccaaggaatcgcgggcccagtgtcactagg     2940 cgggaacaccagcgcgcgtgcgccctggcaggaagatggctgtgagggacaggggagtg      3000 gcgccctgcaatatttgcatgtcgctatgtgttctgggaatcaccataaacgtgaaatg     3060 tctttggatttgggaatcttataagttctgtatgaggaccacagatccccccgagatgtc     3120 atgaaagagagttttagagctagaaatagcaagttaaaataaggctagtccgttatcaac     3180 ttgaaaagtggcaccgagtcggtgcttttttacgcgttgacattgattattgactagt     3240 tattaatagtaatcaattacggggtcattagttcatagcccatatatggagttccgcgtt     3300 acataacttacggtaaatgggcccgcctggctgaccgcccaacgacccccgcccattgacg     3360 tcaataatgacgtatgttcccatagtaacgccaatagggactttccattgacgtcaatgg     3420 gtggagtatttacggtaaactgcccacttggcagtacatcaagtgtatcatatgccaagt     3480 acgcccctattgacgtcaatgacggtaaatggcccgcctggcattatgcccagtacatg     3540 accttatgggactttcctacttggcagtacatctacgtattgtcatcgctattaccatg     3600 gtgatgcggttttggcagtacatcaatgggcgtggatagcggtttgactcacggggattt     3660 ccaagtctccaccccattgacgtcaatgggagtttgttttggcaccaaaatcaacgggac     3720 tttccaaaatgtcgtaacaactccgccccattgacgcaaatgggcggtaggcgtgtacgg     3780 tgggaggtctatataagcagagctctctggctaactagagaacccactgcttactggctt     3840 atcgaaattaatacgactcactatagggagacccaagctggctagcgaaatggcaccgaa     3900 gaagaagcgtaaagtcggaatccacggagtcctgcggcaatggacaagaagtactccat     3960 tgggctcgctatcggcacaaacagcgtcggttgggccgtcattacggacgagtacaaggt     4020 gccgagcaaaaaattcaaagttctgggcaataccgatcgccacagcataaagaagaacct     4080 cattggcgccctcctgttcgactccggggagacggccgaagccacgcggctcaaaagaac     4140 agcacggcgcagatataccccgcagaaagaatcggatctgctacctgcaggatctttag     4200 taatgagatggctaaggtggatgactcttcttccataggctggaggagtccttttttggt     4260 ggaggaggataaaaagcacgagcgccaccaatctttggcaatatcgtggacgaggtggc     4320 gtaccatgaaaagtacccaaccatatatcatctgaggaagaagcttgtagacagtactga     4380 taaggctgacttgcgttgactatctcgcgctggcgcatatgatcaaattcgggggaca     4440 cttcctcatcgaggggacctgaacccagacaacagcgatgtcgacaaactctttatcca     4500 actggttcagacttacaatcagcttttcgaagagaacccgatcaacgcatccggagttga     4560 cgccaaagcaatcctgagcgctaggctgtccaaatcccggcggctcgaaaacctcatcgc     4620 acagctccctggggagaagaagaacggcctgtttggtaatcttatcgccctgtcactcgg     4680
```

```
gctgacccccc aactttaaat ctaacttcga cctggccgaa gatgccaagc ttcaactgag    4740
caaagacacc tacgatgatg atctcgacaa tctgctggcc cagatcggcg accagtacgc    4800 agacctttt ttggcggcaa agaacctgtc agacgccatt ctgctgagtg atattctgcg    4860
agtgaacacg gagatcacca aagctccgct gagcgctagt atgatcaagc gctatgatga    4920
gcaccaccaa gacttgactt tgctgaaggc ccttgtcaga cagcaactgc ctgagaagta    4980
caaggaaatt ttcttcgatc agtctaaaaa tggctacgcc ggatacattg acggcggagc    5040
aagccaggag gaattttaca aatttattaa gcccatcttg gaaaaaatgg acggcaccga    5100
ggagctgctg gtaaagctta acagagaaga tctgttgcgc aaacagcgca ctttcgacaa    5160
tggaagcatc ccccaccaga ttcacctggg cgaactgcac gctatcctca ggcggcaaga    5220
ggatttctac ccctttttga aagataacag ggaaaagatt gagaaaatcc tcacatttcg    5280 gatacctac tatgtaggcc ccctcgcccg gggaaattcc agattcgcgt ggatgactcg    5340
caaatcagaa gagaccatca ctccctggaa cttcgaggaa gtcgtggata agggggcctc    5400
tgcccagtcc ttcatcgaaa ggatgactaa ctttgataaa atctgcctta cgaaaaggt    5460 gcttcctaaa cactctctgc tgtacgagta cttcacagtt tataacgagc tcaccaaggt    5520
caaatacgtc acagaaggga tgagaaagcc agcattcctg tctggagagc agaagaaagc    5580
tatcgtggac ctcctcttca agacgaaccg gaaagttacc gtgaaacagc tcaagaaga    5640 ctatttcaaa aagattgaat gtttcgactc tgttgaaatc agcggagtgg aggatcgctt    5700
caacgcatcc ctgggaacgt atcacgatct cctgaaaatc attaaagaca aggacttcct    5760
ggacaatgag gagaacgagg acattcttga ggacattgtc ctcaccctta cgttgtttga    5820
agatagggag atgattgaag aacgcttgaa aacttacgct catctcttcg acgacaaagt    5880
catgaaacag ctcaagaggc gccgatatac aggatggggg cggctgtcaa gaaaactgat    5940
caatgggatc cgagacaagc agagtggaaa gacaatcctg gatttctta agtccgatgg    6000 atttgccaac cggaacttca tgcagttgat ccatgatgac tctctcacct ttaaggagga    6060
catccagaaa gcacaagttt ctggccaggg ggacagtctt cacgagcaca tcgctaatct    6120
tgcaggtagc ccagctatca aaagggaat actgcagacc gttaaggtcg tggatgaact    6180
cgtcaaagta atgggaaggc ataagcccga gaatatcgtt atcgagatgg cccgagagaa    6240
ccaaactacc cagaagggac agaagaacag tagggaaagg atgaagagga ttgaagaggg    6300
tataaaagaa ctggggtccc aaatccttaa ggaacaccca gttgaaaaca cccagcttca    6360
gaatgagaag ctctacctgt actacctgca aacggcagg gacatgtacg tggatcagga    6420
actggacatc aatcggctct ccgactacga cgtggatcat atcgtgcccc agtctttctct    6480 caaagatgat tctattgata taaagtgtt gacaagatcc gataaaaata gagggaagag    6540
tgataacgtc ccctcagaag aagttgtcaa gaaaatgaaa aattattggc ggcagctgct    6600
gaacgccaaa ctgatcacac aacggaagtt cgataatctg actaaggctg aacgaggtgg    6660
cctgtctgag ttggataaag ccggcttcat caaaaggcag cttgttgaga cacgccagat    6720
caccaagcac gtggcccaaa ttctcgattc acgcatgaac accaagtacg atgaaaatga    6780
caaactgatt cgagaggtga aagttattac tctgaagtct aagctggtct cagatttcag    6840
aaaggacttt cagttttata aggtgagaga gatcaacaat taccaccatg cgcatgatgc    6900
ctacctgaat gcagtggtag gcactgcact tatcaaaaaa tatcccaagc ttgaatctga    6960
atttgtttac ggagactata agtgtacga tgttaggaaa atgatcgcaa agtctgcagca    7020 ggaaataggc aaggccaccg ctaagtactt ctttttacagc aatattatga attttttcaa    7080
```

```
gaccgagatt acactggcca atggagagat tcggaagcga ccacttatcg aaacaaacgg   7140
agaaacagga gaaatcgtgt gggacaaggg tagggatttc gcgacagtcc ggaaggtcct   7200
gtccatgccg caggtgaaca tcgttaaaaa gaccgaagta cagaccggag gcttctccaa   7260
ggaaagtatc ctcccgaaaa ggaacagcga caagctgatc gcacgcaaaa aagattggga   7320
ccccaagaaa tacggcggat tcgattctcc tacagtcgct tacagtgtac tggttgtggc   7380
caaagtggag aaagggaagt ctaaaaaact caaaagcgtc aaggaactgc tgggcatcac   7440
aatcatggag cgatcaagct tcgaaaaaaa ccccatcgac tttctcgagg cgaaaggata   7500
taaagaggtc aaaaaagacc tcatcattaa gcttcccaag tactctctct ttgagcttga   7560
aaacggccgg aaacgaatgc tcgctagtgc gggcgagctg cagaaaggta cgagctggc   7620 actgccctct aaatacgtta atttcttgta tctggccagc cactatgaaa agctcaaagg   7680
gtctcccgaa gataatgagc agaagcagct gttcgtggaa caacacaaac actaccttga   7740
tgagatcatc gagcaaataa gcgaattctc caaaagagtg atcctcgccg acgctaacct   7800
cgataaggtg cttctgctt acaataagca cagggataag cccatcaggg agcaggcaga   7860
aaacattatc cacttgttta ctctgaccaa cttgggcgcg cctgcagcct tcaagtactt   7920
cgacaccacc atagacagaa agcggtacac ctctacaaag gaggtcctgg acgccacact   7980
gattcatcag tcaattacgg ggctctatga acaagaatc gacctctctc agctcggtgg   8040
agacagcagg gctgacccca agaagaagag gaaggtgggt ggaggaggta ccggcggtgg   8100
aggctcagca gaatacgtac gagctctgtt tgacttcaat gggaatgacg aggaggatct   8160
cccctttaag aagggcgata ttctccgcat cagagataag cccgaagaac aatggtggaa   8220
tgccgaggat agcgaaggga aaggggcat gattctggtg ccatatgtgg agaaatattc   8280
cggtgactac aaagaccatg atggggatta caaagaccac gacatcgact acaaagacga   8340
cgacgataaa tcagggatga cagacgccga gtacgtgcgc attcatgaga aactggatat   8400
ttacaccttc aagaagcagt tcttcaacaa caagaaatct gtgtcacacc gctgctacgt   8460
gctgtttgag ttgaagcgaa ggggcgaaag aagggcttgc ttttgggct atgccgtcaa   8520 caagcccaa agtggcaccg agagaggaat acacgctgag atattcagta tccgaaaggt   8580
ggaagagtat cttcgggata tcctgggca gtttacgatc aactggtatt ccagctggag   8640
tccttgcgct gattgtgccg agaaaattct ggaatggtat aatcaggaac ttcggggaaa   8700
cgggcacaca ttgaaaatct gggcctgcaa gctgtactac gagaagaatg cccggaacca   8760
gataggactc tggaatctga gggacaatgg tgtaggcctg aacgtgatgg tttccgagca   8820
ctatcagtgt tgtcggaaga ttttcatcca aagctctcat aaccagctca atgaaaaccg   8880
ctggttggag aaaacactga acgtgcgga gaagcggaga tccgagctga gcatcatgat   8940
ccaggtcaag attctgcata ccactaagtc tccagccgtt ggtcccaaga gaaaagaaa   9000 agtcggtacc atgaccaacc tttccgacat catagagaag gaaacaggca acagttggt   9060 catccaagag tcgatactca tgcttcctga agaagttgag gaggtcattg gaataagcc   9120 ggaaagtgac attctcgtac acactgcgta tgatgagagc accgatgaga acgtgatgct   9180
gctcacgtca gatgccccag agtacaaacc ctgggctctg tgattcagg actctaatgg   9240 agagaacaag atcaagatgc tagaaggcag gggaagcctt ctgacttgtg gggatgtgga   9300
agaaaaccct ggtccatcta gaatgaccga gtacaagccc acggtgcgcc tcgccacccg   9360
cgacgacgtc ccccgggccg tacgcaccct cgccgccgcg ttcgccgact accccgccac   9420
```

-continued

```
gcgccacacc gtcgacccgg accgccacat cgagcgggtc accgagctgc aagaactctt    9480
cctcacgcgc gtcgggctcg acatcggcaa ggtgtgggtc gcggacgacg gcgccgcggt    9540
ggcggtctgg accacgccgg agagcgtcga agcggggggcg gtgttcgccg agatcggccc   9600
gcgcatggcc gagttgagcg gttcccggct ggccgcgcag caacagatgg aaggcctcct    9660
ggcgccgcac cggcccaagg agcccgcgtg gttcctggcc accgtcggcg tctcgcccga    9720
ccaccagggc aagggtctgg gcagcgccgt cgtgctcccc ggagtggagg cggccgagcg    9780
cgccggggtg cccgccttcc tggagacctc cgcgccccgc aacctcccct tctacgagcg    9840
gctcggcttc accgtcaccg ccgacgtcga ggtgcccgaa ggaccgcgca cctggtgcat    9900
gacccgcaag cccggtgcct gagcgggact ctggggttcg aaatgaccga ccaagcgacg    9960
cccaacctgc catcacgaga tttcgattcc accgccgcct tctatgaaag gttgggcttc   10020
ggaatcgttt tccgggacgc cggctggatg atcctccagc gcgggatct catgctggag     10080 ttcttcgccc accccaactt gtttattgca gcttataatg gttacaaata aagcaatagc   10140
atcacaaatt tcacaaataa agcatttttt tcactgcatt ctagttgtgg tttgtccaaa   10200
ctcatcaatg tatcttagc                                                10219
```

<210> SEQ ID NO 33
<211> LENGTH: 30
<212> TYPE: DNA
<213> ORGANISM: Artificial Sequence
<220> FEATURE:
<223> OTHER INFORMATION: Primer

<400> SEQUENCE: 33
tttggtactt gttcagcttt attcaagtgg                                    30

<210> SEQ ID NO 34
<211> LENGTH: 30
<212> TYPE: DNA
<213> ORGANISM: Artificial Sequence
<220> FEATURE:
<223> OTHER INFORMATION: Primer

<400> SEQUENCE: 34
acaatagctc ttcagtctga taaaatctac                                    30

<210> SEQ ID NO 35
<211> LENGTH: 49
<212> TYPE: DNA
<213> ORGANISM: Artificial Sequence
<220> FEATURE:
<223> OTHER INFORMATION: Primer

<400> SEQUENCE: 35
tctttcccta cacgacgctc ttccgatctt aggactgaac gtcttgctc               49

<210> SEQ ID NO 36
<211> LENGTH: 58
<212> TYPE: DNA
<213> ORGANISM: Artificial Sequence
<220> FEATURE:
<223> OTHER INFORMATION: Primer

<400> SEQUENCE: 36
gtgactggag ttcagacgtg tgctcttccg atctcagtca taggaatgga tctatcac     58

<210> SEQ ID NO 37
<211> LENGTH: 21

```
<212> TYPE: DNA
<213> ORGANISM: Homo sapiens

<400> SEQUENCE: 37
ctcgagatgt gatgaaggag a                                              21
```